US010961589B2

(12) United States Patent
Khalil et al.

(10) Patent No.: US 10,961,589 B2
(45) Date of Patent: Mar. 30, 2021

(54) HER2-REGULATED RNA AS A DIAGNOSTIC AND THERAPEUTIC TARGETS IN HER2+ BREAST CANCER

(71) Applicant: CASE WESTERN RESERVE UNIVERSITY, Cleveland, OH (US)

(72) Inventors: Ahmad Khalil, Cleveland, OH (US); Lyndsay Harris, Cleveland, OH (US)

(73) Assignee: CASE WESTERN RESERVE UNIVERSITY, Cleveland, OH (US)

(*) Notice: Subject to any disclaimer, the term of this patent is extended or adjusted under 35 U.S.C. 154(b) by 0 days.

(21) Appl. No.: 15/555,788

(22) PCT Filed: Mar. 7, 2016

(86) PCT No.: PCT/US2016/021165
§ 371 (c)(1),
(2) Date: Sep. 5, 2017

(87) PCT Pub. No.: WO2016/141375
PCT Pub. Date: Sep. 9, 2016

(65) Prior Publication Data

US 2018/0057887 A1 Mar. 1, 2018

Related U.S. Application Data

(60) Provisional application No. 62/128,784, filed on Mar. 5, 2015.

(51) Int. Cl.

| | |
|---|---|
| ***C12N 15/113*** | (2010.01) |
| ***C12Q 1/6886*** | (2018.01) |
| ***G01N 33/574*** | (2006.01) |

(52) U.S. Cl.
CPC ........ *C12Q 1/6886* (2013.01); *C12N 15/1138* (2013.01); *G01N 33/574* (2013.01); *C12N 2310/14* (2013.01); *C12N 2310/20* (2017.05); *C12N 2320/12* (2013.01); *C12Q 2600/106* (2013.01); *C12Q 2600/112* (2013.01); *C12Q 2600/158* (2013.01)

(58) Field of Classification Search
None
See application file for complete search history.

(56) References Cited

U.S. PATENT DOCUMENTS

| | | | |
|---|---|---|---|
| 8,518,897 | B2 | 8/2013 | Rosen et al. |
| 2005/0176024 | A1 | 8/2005 | McSwiggen et al. |
| 2013/0065778 | A1 | 3/2013 | Weidhaas |
| 2013/0136786 | A1 | 5/2013 | Perera |

FOREIGN PATENT DOCUMENTS

| | | | |
|---|---|---|---|
| WO | 2008/077165 | A1 | 7/2008 |
| WO | 2014/031859 | A2 | 2/2014 |
| WO | 2014/162008 | A2 | 10/2014 |

OTHER PUBLICATIONS

Brase, JC et al. "ERBB2 and TOP2A in Breast Cancer: A Comprehensive Analysis of Gene Amplification, RNA Levels, and Protein Expression and Their Influence on Prognosis and Prediction" Clinical Cancer Research 2010, vol. 16, No. 8, pp. 2391-2401.
Ding, X et al. "Long Intergenic Non-Coding RNAs (LincRNAs) Identified by RNA-Seq in Breast Cancer" PLoS One 2014, vol. 9, No. 8, e103270. doi:10.1371/journal.pone.0103270, pp. 1-10.
Graveel, CR et al. "Critical Analysis of the Potential for MicroRNA Biomarkers in Breast Cancer Management" Breast Cancer: Targets and Therapy Feb. 23, 2015; vol. 7, pp. 59-79.
Van Schoonveld, E et al. "Dysregulalion of MicroRNAs in Breast Cancer and Their Potential Role as Prognostic and Predictive Biomarkers in Patient Management" Breast Cancer Research 2015 (published online Feb. 18, 2015), vol. 17, No. 21, pp. 1-15.

*Primary Examiner* — Sean Mcgarry
(74) *Attorney, Agent, or Firm* — Tarolli, Sundheim, Covell & Tummino LLP

(57) ABSTRACT

A method for treating HER2 positive breast cancer in a subject in need thereof includes administering to cancer cells of the subject an agent effective to modulate the level of HER2-associated RNA in the breast cancer cells of the subject.

2 Claims, 8 Drawing Sheets

Specification includes a Sequence Listing.

A
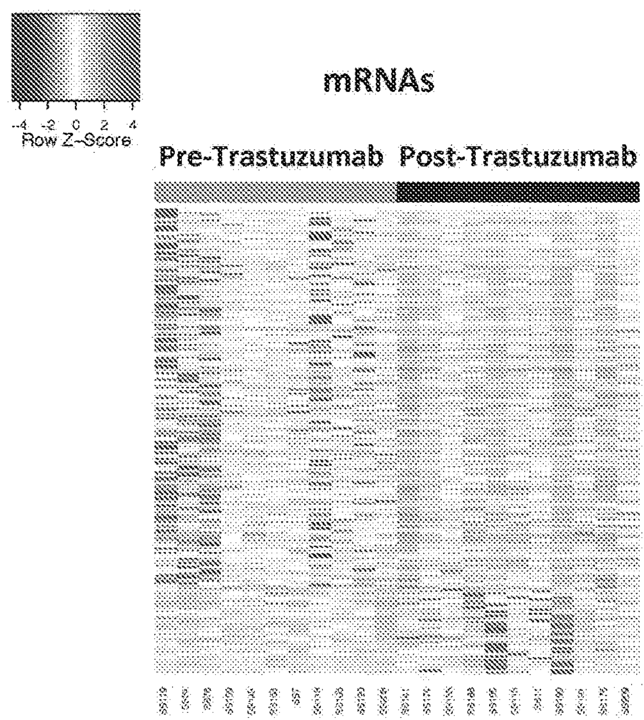
B
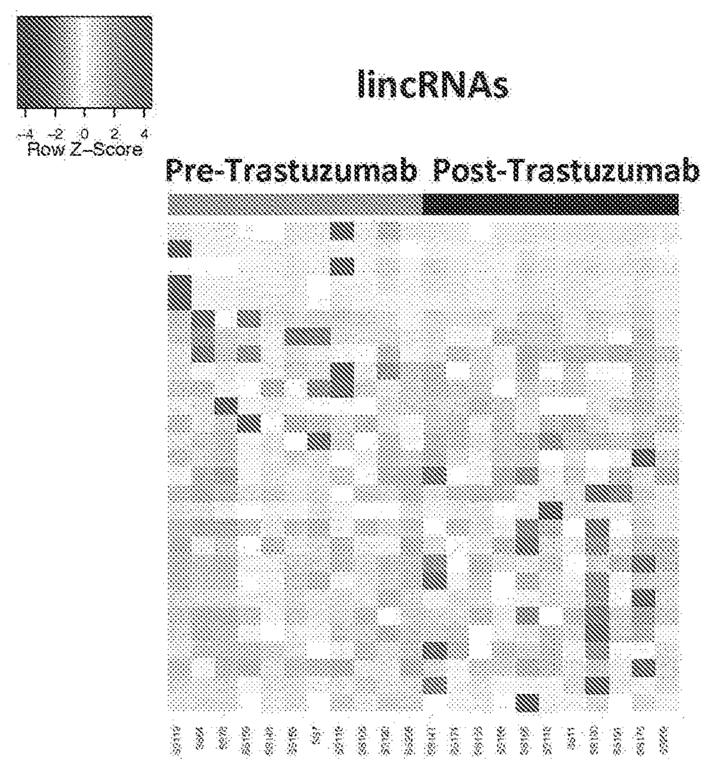
Figs. 1A-B

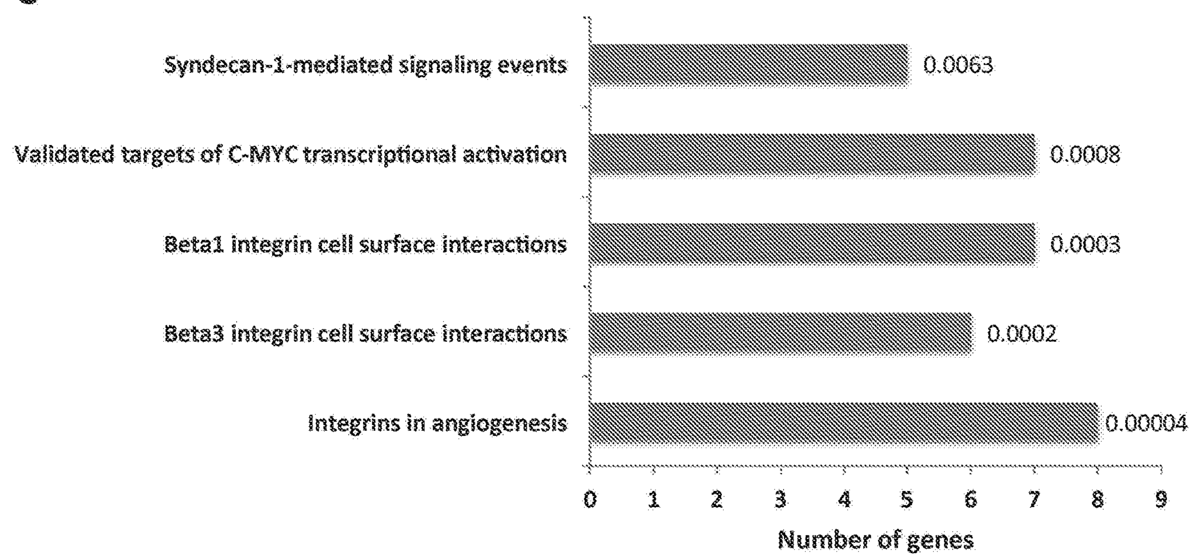
Fig. 1C
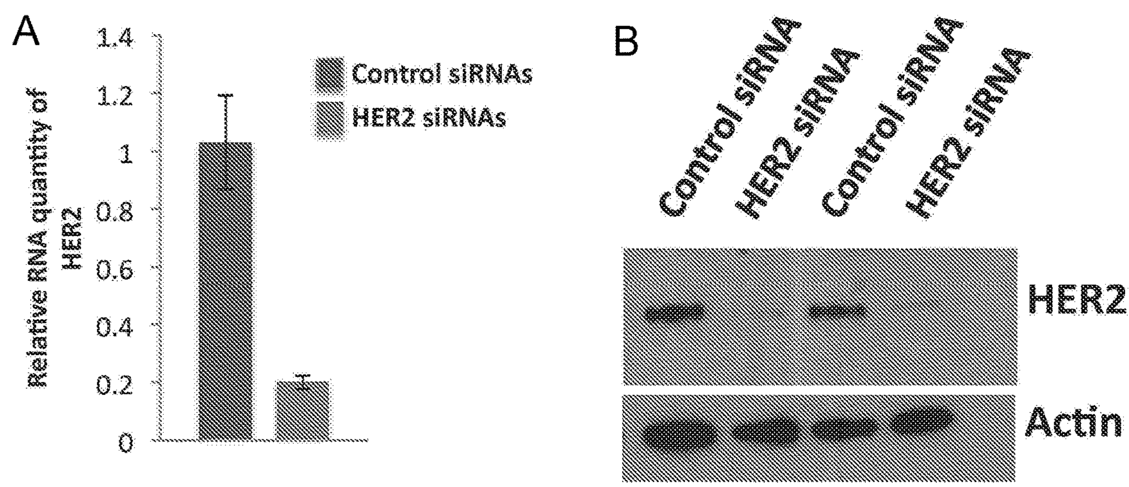
Figs. 2A-B

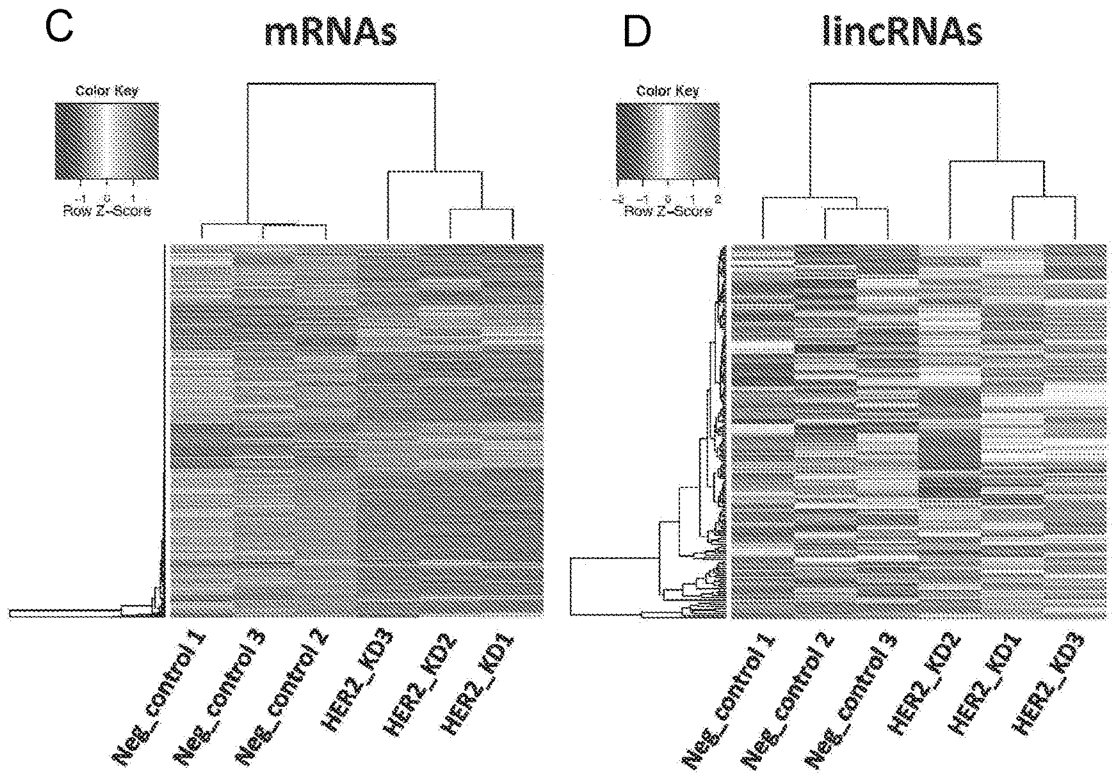
Figs. 2C-D
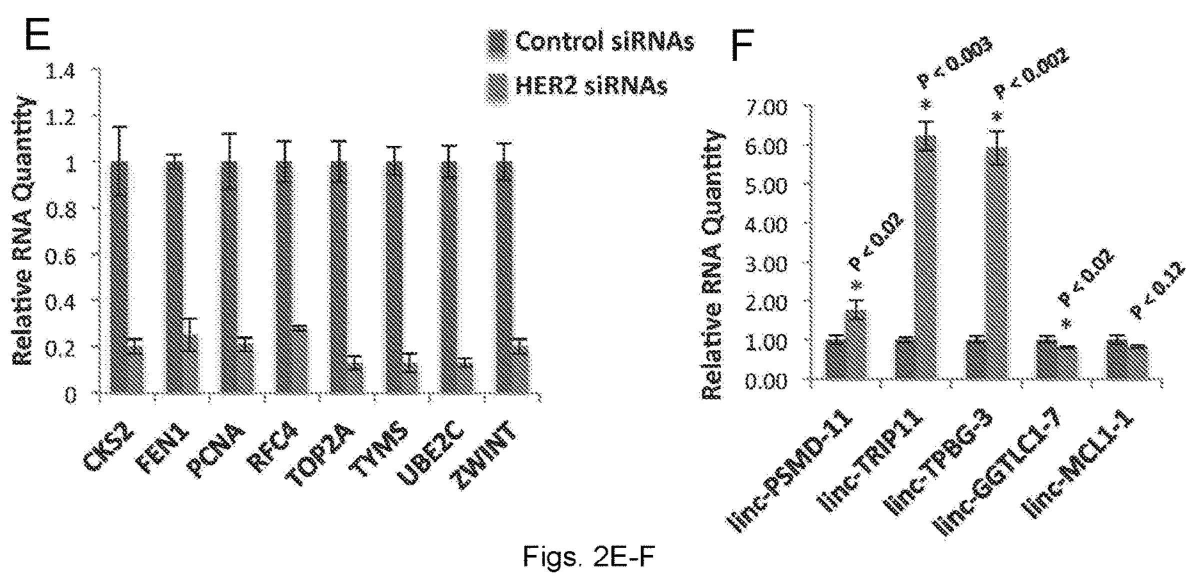
Figs. 2E-F

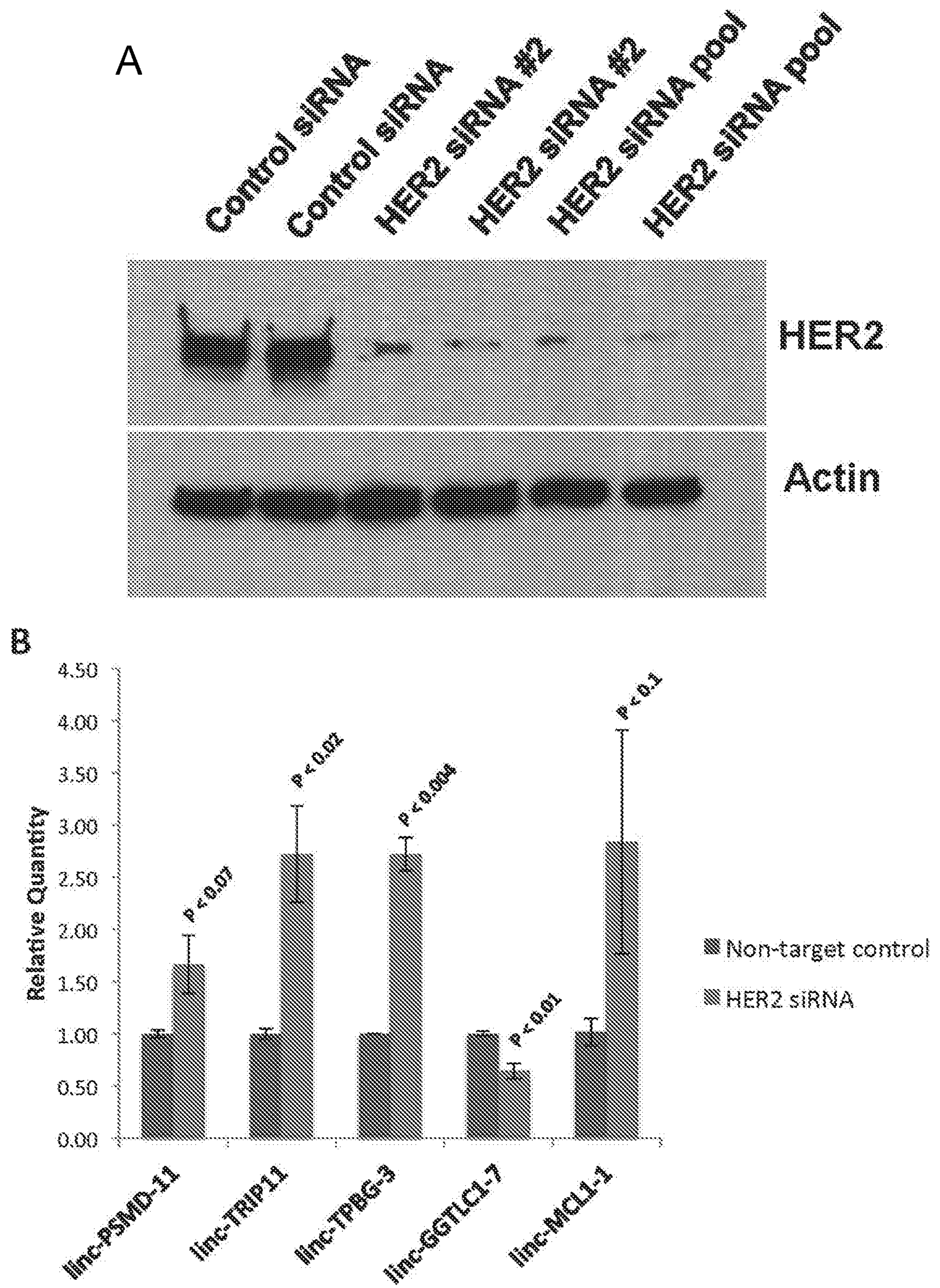
Figs. 3A-B

A
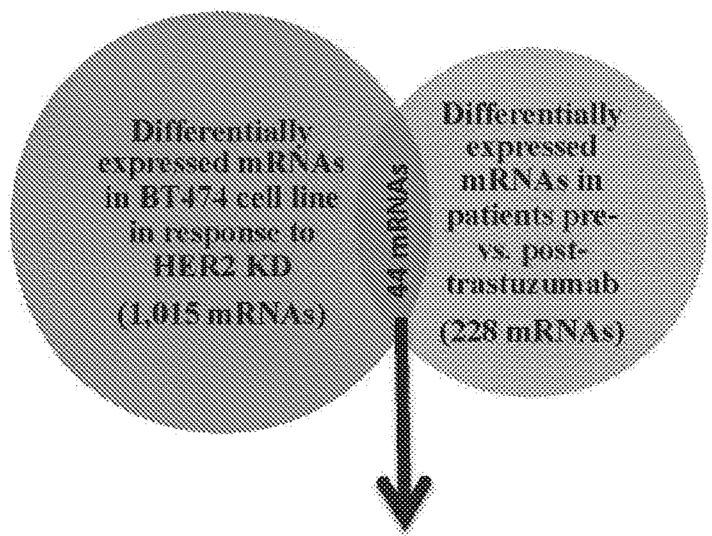
B
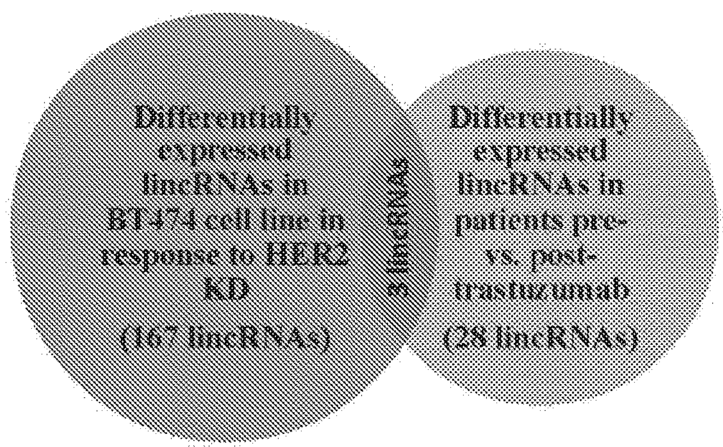
C
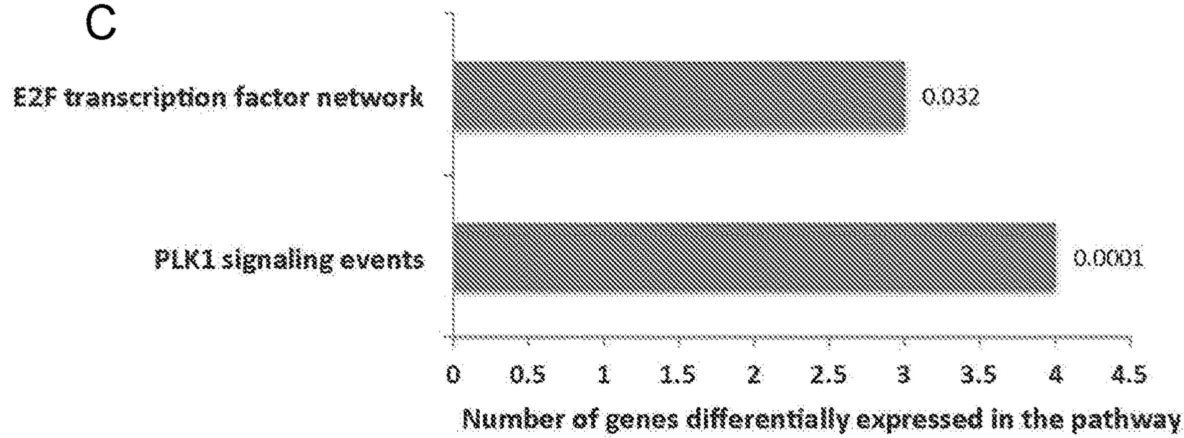
Figs. 4A-C

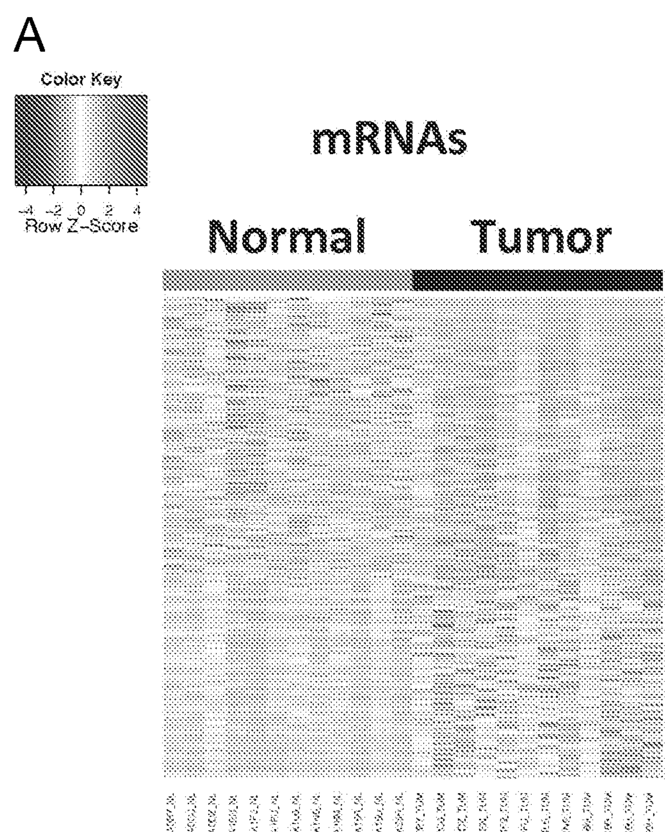
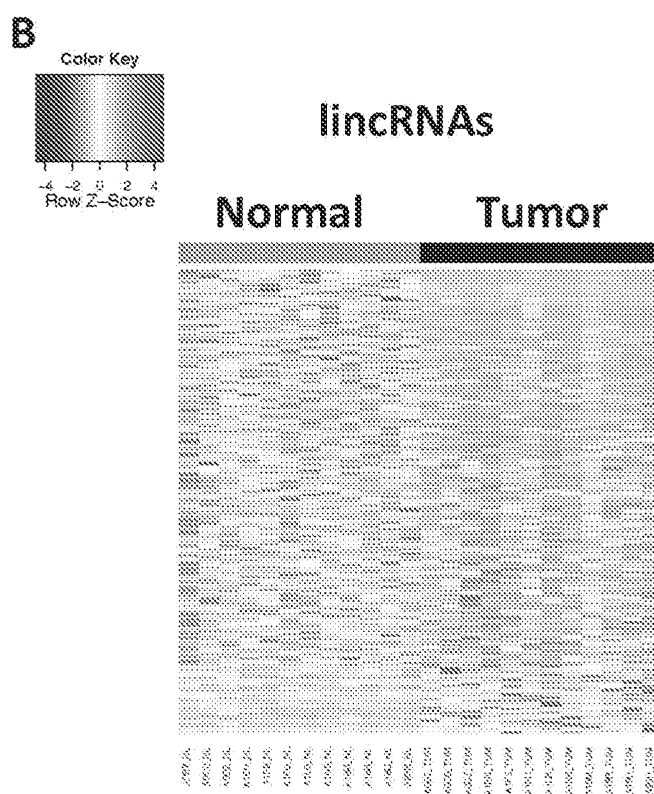
Figs. 5A-B

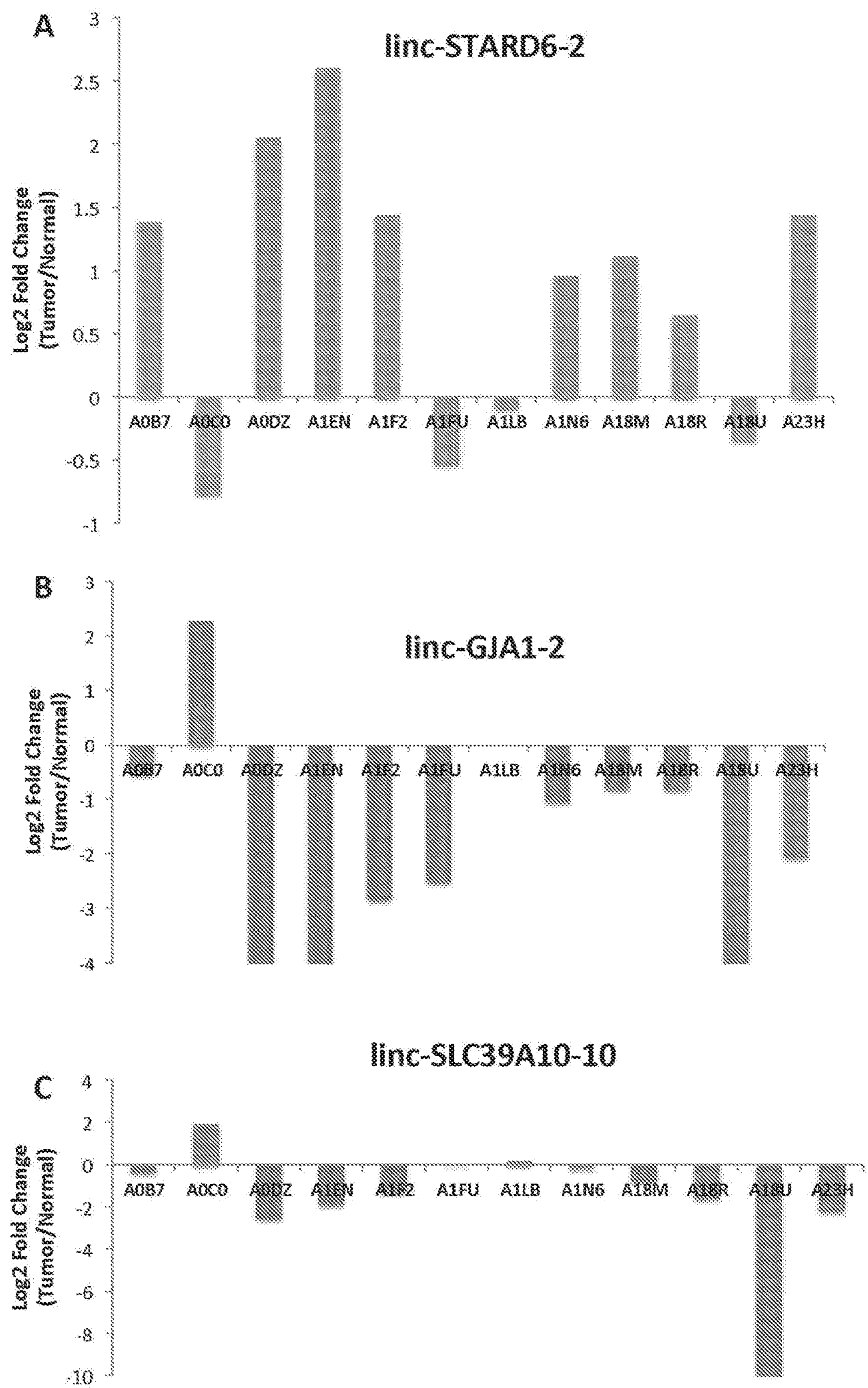
Figs. 7A-C

SEQUENCE LISTING

```
<160> NUMBER OF SEQ ID NOS: 38

<210> SEQ ID NO 1
<211> LENGTH: 2199
<212> TYPE: DNA
<213> ORGANISM: Homo sapiens

<400> SEQUENCE: 1

tttaaagggc gcgggcgctg gcagtcggcg gtgcaccgga ttccagctgt tttcgcctgc      60

tcctcgccgt ctccgccgct gccctcgttc gccatgctct ccgtccgcac cccgctcgcc     120

accatcgctg accagcagca gctgcagttg tcgccgctga agcgactcac cctggctgac     180
```

```
aaggagaaca cgcccccgac tctcagcagc acccgcgtcc tggccagcaa agctgcgagg    240
agaatcttcc aggactccgc cgagctggaa agtaaagcgc ctactaaccc cagcgttgag    300
gatgagccgt tactgagaga aaccccccgc cgcttcgttg tctttcccat cgagtaccat    360
gatatctggc agatgtacaa gaaagccgag gcctcctttt ggactgccga ggaggtggac    420
ctttccaagg atattcagca ctgggaagct ctgaaacccg atgagagaca ttttatatct    480
cacgttctgg ctttctttgc agcgagtgat ggcatagtca atgagaactt ggtggagcga    540
tttagccaag aagttcaagt tacagaggcc cgctgtttct atggcttcca aattgccatg    600
gaaaacatac actctgaaat gtacagtctc cttattgaca cttacattaa agatcccaag    660
gaaagagaat atctcttcaa tgctattgaa acaatgcctt gtgtgaagaa gaaggctgac    720
tgggccttgc gctggattgg ggacaaagag gctacgtatg gagaacgcgt tgtggccttt    780
gccgccgtag aaggaatctt cttttccggt tcttttgcat cgatattctg gctcaagaaa    840
cgggggctga tgccgggcct tacattttcc aatgagctta ttagcagaga cgagggttta    900
cactgtgact ttgcctgcct gatgttcaag cacctggtac acaagccagc agagcagagg    960
gtccgagaga taatcaccaa cgccgttagg atagagcagg agttcctcac ggaggccttg   1020
cccgtgaagc tcatcgggat gaactgcact ttgatgaagc agtacattga gtttgtggcc   1080
gacaggctta tgctggagct gggttttaac aagattttca gagtagaaaa tccgtttgac   1140
ttcatggaaa atatctcact agaaggaaag acaaacttct ttgagaagcg agtaggcgag   1200
tatcagagga tgggagtcat gtcgaattcg acagagaact cttttacctt ggatgctgac   1260
ttctaagtaa ctgatcgtgt gttcttcgct gatttttgtc cccttgccat taaaagaaac   1320
cagcaaaaac aaccaactgg ctacaccatg aattgtcatt aaatttgcta aacaggtgtc   1380
taaaaagctg tgtagctacc tcagtcctgt ttgccaggct ggtcactaga agaaagtata   1440
cttcaaacaa tgggtacttg gatccttagg gagatcctgt ccttggcttt tacaagtagt   1500
gtggtcacct ttgacctcat caaagtacta acagcactgg gccaggtttt aggagcagtg   1560
accatcaagc aagcaggttt aaacatttag atgctgttta gggctgttta aagatgtcgg   1620
actgcttcct gcaggcatgc agggtctact taacaagttt gtaaataaaa ttggcacttt   1680
gcacacacac acacatagtg ctgtcaggcg attaaactat acattttatg aggtagtacc   1740
tctatgcttt tttttttttt ttttaatgct cagtattatc ttgaagtttg caaatgctat   1800
gatggtacag taaattctga catttgccct aatagtgtca cttttttttt ttcttcgaga   1860
cagagtttct ctgtatagcc ctggctgtac ggaattcaca agtgagtttg agcccagtgg   1920
tgggtacacc cgtgggactc ttacaaacca aaacaggaaa agcaagtgtt ccctgaggta   1980
gtttactgtg atctagcttc ctcatgaact gacataaccc tgatcagttt ccttgattat   2040
tgtatagatg tttttgtaat atgaaaagcc tttgtacctt ttaaattatt gttacttaaa   2100
attaataaac tcttgaatta acagtcttga actttcatgg catacaagta ttaaatgatt   2160
taactaaaac cttaatgtca aaaaaaaaaa aaaaaaaaa                          2199
```

<210> SEQ ID NO 2
<211> LENGTH: 5217
<212> TYPE: DNA
<213> ORGANISM: Homo sapiens

<400> SEQUENCE: 2

```
tcctaaccga caagcgtctg tgaggggagc gtccaggtcc cgcgtcgcgc gtcgcgggtc     60
gcctagcgtt tcccgctggt tttgtcgctt tccggattct cgagcctctt caggaccgtc    120
```

```
accatggagt tgtcaccgct gcagcctgta aatgaaaata tgctaatgaa caaaaagaag    180
aatgaagatg gcaagaaaag attgtctatt gaaagaatct atcagaaaaa aacacaactg    240
gaacatatac tgctccgccc agatacctac attggctctg tggagttagt gacccagcaa    300
atgtgggttt acgatgaaga tgttggcatt aactacaggg aagtcacttt tgttcctggt    360
ttgtataaaa tctttgatga gattctagtt aatgctgctg ataacaaaca aagggaccca    420
aaaatgtctt gtattagagt cacaattgat ccagaaaata atgtaattag catctggaat    480
aatgggaaag gaatccctgt tgttgaacac aaagttgaga aatatatgt cccagctctc     540
atatttggac aactcctgac ctccagtaac tatgacgacg atgagaagaa agtgacaggt    600
ggtcgaaatg gctatggagc taaactgtgt aacatattca gcaccaaatt tactgtggaa    660
acagccagta gagagtacaa gaaaatgttc aaacagacgt ggatggataa catggggaga    720
gctggtgaca tggaactcaa gccctttagt ggagaagatt atacatgtat caccttccag    780
cctgacttat ctaagtttaa aatgcaaagc ctggacaaag atattgttgc actgatggtc    840
agaagagcat atgatatcgc tggctccact aaagatgtca aagtctttct taatggaaat    900
agtctgccag tgaaaggatt ccgcagttac gtggatttgt atttgaagga taaggtagat    960
gaaactggga attcactgaa ggtgatacat gaacaggtca atccccggtg ggaagtgtgc   1020
ttaacaatga gcgagagagg cttccagcag attagcttcg tcaacagcat tgcgacttct   1080
aagggcggca gacatgtcga ttatgtagct gatcagattg tgagcaaact cgttgatgtg   1140
gtgaaaaaga agaacaaggg cggggttgca gtgaaggctc atcaggtgaa aaatcacatg   1200
tggatttttg taaatgcctt aattgaaaac ccaacctttg actctcaaac aaaagaaaac   1260
atgactttac aagccaagag ctttggatca acatgtcaat taagtgaaaa gttcatcaaa   1320
gctgcaattg gttgtggtat tgtggaaagc atactaaact gggtgaagtt caaggctcaa   1380
atccaactga acaagaagtg ttcagctgta aaacatacca aaatcaaggg aatccccaaa   1440
cttgatgatg ccaacgatgc agggagccga aactctactg aatgcacact tatcctgact   1500
gagggagact cagcaaaaac tctagccgtt tcaggccttg gagtggttgg aagagacaaa   1560
tatggggtgt tccctcttag aggaaagata ctcaatgtgc gagaagcctc tcataaacag   1620
atcatggaaa atgctgaaat taacaatatc atcaagattg tgggtctcca gtacaagaaa   1680
aactatgaag atgaagattc attgaaaact cttcgttatg ggaagatcat gattatgaca   1740
gatcaggacc aagatggttc ccacatcaaa ggcttgctga tcaattttat ccatcacaat   1800
tggccatctc ttctgcgaca tcgttttcta gaagaattta tcactcccat tgtaaaggtg   1860
tccaaaaata agcaagaaat agcattctat agtcttcccg agtttgaaga atggaaaagt   1920
tcgactccga atcataaaaa gtggaaagtc aaatactaca aaggtttggg caccagcaca   1980
tcaaaggaag ctaaggaata ttttgcagat atgaaacgac atcgtattca gttcaaatac   2040
tctggccctg aagatgatgc tgcgatcagc ctggccttta gtaaaaaaca agttgatgat   2100
cgaaaggaat ggttaactaa ttttatggaa gacagaagac agcggaagtt acttggcctt   2160
cctgaggatt atttgtatgg acaaagcact tcgtacctga cctataatga cttcataaac   2220
aaggaactca tcctcttctc caactctgat aatgaaaggt ctatcccatc catggtagac   2280
ggtttgaaac caggtcagag aaaggttttg tttacttgtt tcaaacggaa tgacaagcga   2340
gaagtgaagg ttgcccagtt agctgggtca gtggcagaaa tgtcctctta tcaccatggt   2400
gagatgtcac tgatgatgac cattatcaat ttggcgcaga attttgtggg tagcaataat   2460
```

-continued

```
ttgaaccttt tacagcccat tggtcagttt ggaaccaggc tgcatggtgg caaggactca   2520
gctagtccta ggtacatctt tacaatgctc agccctttgg ctcggttgtt gtttcctcca   2580
aaagatgatc acacattacg gtttctatat gatgacaacc aacgtgttga gcctgaatgg   2640
tacattccta taatacccat ggtgctgata aatggtgctg agggaattgg tactgggtgg   2700
tcctgcaaaa tccccaactt tgatgtgcgt gaagttgtga ataatatcag acggcttctg   2760
gatggagagg agcccctacc catgctccca agttataaga atttcaaagg tactattgaa   2820
gaactggctt caaatcagta tgtgattaat ggagaagtag ctattctgga ttctacaacc   2880
attgaaatct cagagcttcc catccgaacg tggactcaga catataaaga acaggttcta   2940
gaacccatgt tgaatggaac tgagaagaca ccctctctaa taacagacta tagggaatac   3000
catacagata ccactgtgaa gtttgtcata aagatgactg aagaaaaact ggcagaggca   3060
gagagagtcg gcctacacaa agtcttcaaa ctccagagta gtctcacttg caactctatg   3120
gtgctttttg accatgtagg ttgcttaaag aaatatgaca ctgtgttgga tattctaaga   3180
gacttctttg agctcaggct taaatattat ggattaagaa aagaatggct tctaggaatg   3240
cttggtgcag aatcttctaa actgaataat caagctcgct ttatattaga gaaaatagat   3300
ggcaaaatag tcattgaaaa taaacctaaa aaagaattaa ttaaagttct gattcagaga   3360
ggctacgact ctgaccctgt gaaagcctgg aaagaagctc agcagaaggt tccagatgaa   3420
gaagaaaatg aagaaagtga cactgaaacc agcaccagtg actctgcagc cgaggctggg   3480
ccgaccttca actaccttct cgacatgccc ctgtggtatc tgaccaagga gaagaaggat   3540
gagctgtgca aacaaagaaa cgagaaggaa caagagctca acacattaaa gcaaaagagt   3600
ccatcagatc tgtggaagga agatctggct gtttttattg aagaactgga ggttgtcgag   3660
gccaaggaaa agcaggatga acaagtgggc cttcctggaa aggcggggaa agcaaagggg   3720
aagaaagcac agatgtgtgc tgacgtcttg ccttctcctc ggggcaaaag agtcatcccc   3780
caagtgactg tggagatgaa agctgaggca gagaagaaaa ttaggaagaa aattaagagt   3840
gaaaacgttg agggtacccc tgctgaggat ggtgcggaac caggaagcct ccggcaacga   3900
atagagaaga agcagaagaa agagccaggt gcaaagaagc agactacatt gccgtttaag   3960
cctgtcaaaa aagggaggaa gaaaaacccc tggtctgact ctgagtcaga cgtgagcagt   4020
aatgaaagta acgttgatgt ccctcctcga caaaaaagagc aaagaagtgc tgcagcaaaa   4080
gccaaattca cagtggattt agactcggat gaagatttct caggtttgga tgagaaggat   4140
gaggatgaag atttcctccc attagatgct actccaccta aggccaaaat ccccccaaaa   4200
aatactaaaa aagcactgaa gacccaggga agctccatgt cggtagttga tcttgaaagt   4260
gatgttaagg acagtgtgcc agcttctcca ggcgttcctg ctgctgactt cccagcggaa   4320
actgaacagt caaagccatc caaaaagacc gtgggagtga agaagacagc aaccaaaagc   4380
cagtcttcag tctccactgc tggtaccaaa aagagagctg cgccaaaggg aaccaaatca   4440
gattcagcct tgagtgctcg tgtctcggaa aaacctgctc ctgccaaagc caagaacagt   4500
cgcaaaagga agccatcttc ttctgatagc tctgactctg attttgagag agcaatttct   4560
aaaggtgcca cgagcaagaa agcaaaggga gaggaacagg acttccctgt ggacttggaa   4620
gacacgatag ctcctcgagc caaatctgac cgggcgagga agccaattaa gtacctggag   4680
gagtccgatg acgatgacga cctcttctga ggcagaagag attgttttag ggatggtttt   4740
acggagccag ttttataggt agaattcggt catatagaac tggttagttc tagtacagat   4800
acagtgctca acctctgacg tgatgcattt tgtttaagcc atgagaagtt gctcgtacct   4860
```

```
tttgaacatc ggaggctgga gaaagtcacc ttgactgtgt ctttatgact cagcacaagc   4920

agcaaggtga ggaaagttag gtcagttacg tagagtactg actctactcg ggatgccttc   4980

ccaacacgag atccctggga ggaggcagga ctgctcacgg ttacatctcc aggatcaacc   5040

aggaagtggg atccattgca gatctccata attccaactt gtgactgcca agaccttctg   5100

tgctgttgtc tcttatttaa gtgctgttat caatgtcttt tgtaaatatt taatatgtct   5160

gtctgttccg ctaattccaa ctattttgta ctttaataaa tcttctaaac aatgcaa      5217
```

<210> SEQ ID NO 3
<211> LENGTH: 3113
<212> TYPE: DNA
<213> ORGANISM: Homo sapiens

<400> SEQUENCE: 3

```
ggagacttgg ggttccccac cccagccctc ccaaggcctc tgccaaaacg cggagccgaa     60

ccgtagcctg acactccgag atctaagagc caccgtgagg gggcccggcg cgaactggaa    120

ggcgtgcggg agcctgtggt gggcaaccag catgggggag gagcctctga gccgtgcagc    180

cgcggcgcgc gcagaggttt catagtcctt gaagagaatg tcaagacgca gtagccgttt    240

acaagctaag caacatgccc agcccaacca gccagactct ccgcaagaaa cccagataat    300

tcaggccaag aagagaaaaa cagcacagga tgtcaaaaaa agaaaagagg agatcaccaa    360

gaagcatcag tatgagatta ggaattgttg gccacctgta ctgtctggag gaatcagccc    420

ttgcattatc attgaaacac cccataaaga aataggaaca agtgacttct ctagatttac    480

aaattacaga tttaaaaatc tttttattaa tccctcacct ctgccagatt taagctgggc    540

atgttcacag gaggtttggc aaaacatgtt acaaaaggaa aacagatacg tgcatgacaa    600

acattttcaa gttctgcatt ctgacctgga accacagatg aggtcaatac ttttagactg    660

gcttttagag gtttgtgaag tatacactct tcatagggag acattttacc ttgcccaaga    720

ctttttttgac agatttatgt tgacacaaaa ggatgtaaat aaaaatatgc ttcaactcat    780

tgggattacc tcattgttca ttgcttccaa acttgaggaa atctacgctc ctaaactcca    840

agagtttgct tacgtcactg atggtgcttg cagtgaagta gatatcttaa agatggaact    900

caatatatta aaggctttaa aatgggaact ttgtccagta acagtcatct cctggttgaa    960

tcttttttctt caagttgatg ctgttaaaga tgttcctaag gttcttctac ctcaatattc   1020

tcaggagacg ttcatccaga tagctcagct tttagatctg tgcattctag ccatcgactc   1080

tttagaattt caatacagaa ttctggctgc tgccgcctta tgtcatttta cctccattga   1140

agtggttaag aaagcttcag gtttggaatg ggatgacatc tcggaatgtg tagactggat   1200

ggtgcctttt gttagtgttg taaaaagtgt gagtccagtg aagctgaaga cttttaagaa   1260

gatacccatg gaagatagac acaatatcca gacacacaca aattatttgg ctttgctgaa   1320

tgaagtaaac tatgtgaaca tctacagaaa aggagggcag ctgtcaccag tgtgtaatgg   1380

aggcattatg acaccaccaa agagtactga aaaaccacca ggaaaacact gaagttaaca   1440

acctggaatt gaacaaataa tggatagttt catataaatg agttttacag aaaagtagtg   1500

ctgtaactat ccttgtctaa ggagttacac tgccattctt ttacttaaaa actatatcaa   1560

tttggcacta aatgcctagg atgcacaaaa tcctgggttc aatccccagc actacaaaag   1620

gaaacaaaac aaaaacttca aaaaattggc actaaagaag tatttcctat aaaagagaac   1680

ttgtttacaa aggtgacttc actcccaagg atagtggatg gaagccaaca atttaagcta   1740
```

```
tagcagttgt ttctgtttgt tactgtgttt ctttaaaatt cagtgttact gtatttcttt   1800
tgatgaacta ggaattttat cattggaata tggactaaac tagtgctacc ttaaaggata   1860
cattagctga cacagaactt tgaatctaga ttttatattc ttaaattcct atactcttga   1920
atggtgcaat ttgtttttga aaataaattt taagcttatt tacaaaggtt gttttgtaat   1980
aaagtgacta atttatctaa agcagtttgt aacaaacgat aaaacttgaa ttttatgaat   2040
ggtaaagttc aatctgtttt gaactagttt gtctgccttg ccatatttct taatcagtaa   2100
ggcactgaac caaatgttta aactgtgctc taaatgggag aaccaaagaa attataaaca   2160
agatataaat gctttggctt cttctactcg gggttttac ttgatagaaa ggttgcttta   2220
taatcttttt gtgtatcaca atttgggtaa aattaaacac tttttcaaac tatataagaa   2280
agtcacttta ttgcacacta agatatctct aaggcgcttt atgtttgcaa aactggtggt   2340
ccatttttaa gccccatatt atgagatgag gactgtgtca acatgaaaaa actttaacat   2400
atgacctaaa ctattttctt atggcagaaa atattaaatg tatacttact cctagaaatt   2460
tatttattta aacttgctgt atatagaata gctacttata cattaaatat tttaagttag   2520
cctttgaaaa ggaaatttgg gcctaaaaaa gttaatttca ttagaaaaaa aatggtacca   2580
ggcatgaacc ttgtctctct ttgaagaaat tataaactat tgttaagata tgaagttttt   2640
gtataatttg tttataaact aatttgtttc agtttgtttt ggtctaaaaa gaaaacacca   2700
ctaaattgta catatgtatt atataaactt aatcttttaa tactgtttac ttttagccca   2760
ctgtttaaaa aataaaattg aaaaaaaatt aactaactgc ttaaaagtaa agttttgcca   2820
ttgcttgtag aaacttcttt ttccttctct gtgctgccag ctgtaatact tcttcagggt   2880
tgcttgcatt caattctgtt tggccaatgg ctttgatctt aaaacagaaa agtgttatta   2940
gaagtttgac tgaaaaaaat tgtcacagta gtacacataa ctcaaagtta aagttaacta   3000
aatcaaatta aaaactacag aaaaaaatgg catcacattg atccactttt agtatggtta   3060
cctggaggga catttagtta cactaaataa atttctgtat gcttatgtga ttg          3113
```

<210> SEQ ID NO 4
<211> LENGTH: 5506
<212> TYPE: DNA
<213> ORGANISM: Homo sapiens

<400> SEQUENCE: 4

```
ggggcttccc gatcccgcgc aaatcgaaag gtccatggct gcgcttgcag cagccgctcg     60
ccgccgttct gaaccccagg tttgaggagc cacggcgcct ggaatggact tgtgtgctat    120
gcctgttcgt tcgggagacg ggactaagtt aacttggcac gatggggatt caagggttac    180
ttcagttcat ccaagaagct tctgaacctg tcaacgtgaa gaagtacaaa ggacaggcag    240
tggctgtgga tacctactgt tggcttcaca aaggggctat tgcttgtgct gaaaagctag    300
ccaaagggga acctacagat aggtatgtag gattttgtat gaagtttgtt aatatgctgc    360
tgtcttatgg ggtcaagccg attctcatat ttgacggatg tactctacct tctaaaaagg    420
aagtggagcg gtctcgaaga gagagacgac aaagcaacct tcttaaaggg aagcagcttc    480
ttcgagaggg caaagtgtca gaagcccgag actgcttcgc tcgctctatc aacatcacgc    540
acgccatggc ccacaaagta ataaaagctg ctcgggccct aggagtggat tgcctcgtgg    600
ctccgtatga agctgatgct cagttggcct accttaacaa ggctggcatc gtgcaggctg    660
tcatcacaga ggactctgac ctcctcgcat ttggctgtaa gaaggtgatt ttaaaaatgg    720
atcagtttgg aaatggactg gaagtggacc aggcacggct aggcatgtgc aagcagcttg    780
```

```
gggatgtatt cacggaggag aagttccggt acatgtgcat tctgtccggc tgtgactacc    840
tcgcctccct tcgtgggatc ggcttagcca aggcctgcaa agtgctgaga ctggccaata    900
accccgatat cgtgaaggtt atcaagaaaa ttgggcatta tctcaggatg aatataacgg    960
tgcccgagga ttacatcaca ggatttattc gtgccaacaa tactttcctc taccagctcg   1020
tgttcgaccc catccaaagg aagctggtcc ctctgaatgc ctacggagat gacgttaatc   1080
ccgaaacact gacttacgct gggcagtacg tcggtgactc tgtagctctt cagatcgccc   1140
ttggaaatag agatgtaaat acttttgaac agattgatga ctacagtcca gacaccatgc   1200
cagcccactc aagaagccac agctggaatg agaaagcagg tcagaaacca cctggtacca   1260
acagcatttg gcacaagaat tattgtccta gacttgaggt gaacagtgtc tcccacgctc   1320
ctcaactgaa ggaaaagcca agcactttgg gccttaaaca agtgattagt actaaagggt   1380
taaatcttcc caggaagtct tgtgtgttga aaagaccaag aaatgaagcg ctggctgaag   1440
atgacctgtt gagccagtat tcgtcagttt caaagaagat caaggaaaat ggctgtgggg   1500
atggcacatc acctaactct tctaaaatgt ccaagtcctg ccccgattct gggactgctc   1560
acaagacaga tgcacacacc ccgtctaaga tgaggaataa atttgcaacg ttcttacaga   1620
ggaggaatga agaaagcggt gcagtcgtgg ttccagggac cagaagcagg ttttttttgca   1680
gttctcagga ttttgacaat ttcataccaa aaaaagaaag cggccagcct ctaaatgaaa   1740
ctgtggccac tggcaaagcc accaccagcc tcctcggggc actggactgt ccagacacgg   1800
aaggccacaa gccggttgat gcaaatggga cgcacaatct gagctctcag attccaggca   1860
atgcagctgt gtctcctgag gatgaggctc agtcctctga gaccagcaaa ctcttggggg   1920
ccatgtcccc acccagtctg ggacactaa gaagctgttt cagttggtct ggcactctca   1980
gggaattttc tcgaactcca agtccctcag caagcactac attgcagcag ttccggagaa   2040
agagcgaccc ccctgcctgt cttcctgagg cctctgccgt ggtcactgac aggtgcgact   2100
caaagagcga gatgctgggt gagacgtctc agcccttgca cgagctgggc tgctcctcgc   2160
ggtctcagga aagcatggac tcctcgtgcg gcctaaacac gtcgagcctg tcccagcctt   2220
ccagtaggga ttcaggttca gaggagtcgg attgtaacaa taagtcactt gataatcaag   2280
gggaacagaa ctccaagcaa cacttacctc actttcaaa gaaagacgga cttagacgga   2340
acaaggttcc tgggctctgt aggtctagtt ctatggactc tttttctaca accaagatca   2400
agcccctggt gcctgccagg gtcagtggcc tgagcaagaa gtcaggaagc atgcagacga   2460
gaaaacacca tgatgtggag aacaagccag gcctacagac gaagatcagc gagctctgga   2520
aaaactttgg gtttaaaaaa gattctgaaa agcttccttc ttgtaagaag cccctgtctc   2580
cagtcaagga caatatccaa ctcactccag agacagaaga tgagatcttt aacaagcccg   2640
agtgtgtacg cgctcagaga gcaatatttc actaagtgca gaccgttgcc tacaagaaaa   2700
tcttatcaac tggagagatg tattagtctc aatgtcattt tttaaatgga ttacattttg   2760
tatattaact ttgtgacttt cttttgctca gctttttata ttttcataga aagctaaata   2820
gaagaataaa tctgtctttg acatttctgg gaagtttaaa tgctaattgg acaaatcttc   2880
tgacatcagt agcaatctaa aggactctac catgtatgta gcatctagtc tattgtgagt   2940
agaaagccac aggtgcctac agccacttag acccaagaac agatgactcg ccagcttcca   3000
accactccag ccgcctttct gtcagccctg taagggtaaa ttgagaagag tgttgctggg   3060
atgggaaggg gcagcaggag gagctgtctg cctaagattg ttcacacgcc tcggtctcaa   3120
```

-continued

```
agctgctacc tggttttctc catgcacttc tgaagtgtgg ctcaaaagtt cctttgcatt   3180
tacttaaccc tgtgcaagat gctgaagctg cagagcctgt gatcaatata ttctgcaaag   3240
atccaggcag aggttttgga aggaatcagc catacctgga ccaatctgaa caatcagaag   3300
gaaaggcatg atgaagccat ctatgataca ggcgagagtc caagacttag aatctttaaa   3360
agggagttgg ggaggggcaa acacagattt atttggaaaa tcctaatctg aagctcagat   3420
ttgagcccgc cgtgagcagt cctgtcacca cacaggtcag acagacagac agacagacac   3480
catctacagg tattcatctc tggaatgtca ggaaaccagt aaaatgcact atacagcttt   3540
tctgggaagc atcaagcaag aaggaagagt gtcagtcaag gaagggtggg ttctctgttg   3600
gcagcagcca agcaggtctt gtggatggct tctatcagtg gtgagacagg caagctcctg   3660
ttagccaagg gtagagggca aggctggaaa caggctattt ttttctcaaa tctttaaaac   3720
aacaacaaga tctccaagtc actgcagtac acaagcccca ttaacagcta gtttccatga   3780
cagtcttcat agtttgcaaa tagaaattgc tccatagtat ctgaccacag accataggat   3840
aggccacaga taaccacgta tcacagtagt aggacttgag aactgcacca ttgacagtac   3900
agttcaaagg atggagacca gccagagtcc ctctgattgt gactccttgt agcttctttt   3960
ggaccatgtt tgtctatgtt tggttcctgc tcacaagaac aggtgtgggg attgggccac   4020
actgagcaag ggacatgagc aggttgatgg ggtattaagg ttgtcactac tttgtcttta   4080
aagtgtcatt tgtggaggga caagaaaaag gctggaaatt caggtaggtc agattttgaa   4140
agttcagaca caggagtata gacttaagat caagtcacga gagaaagcgt tgcctggcca   4200
gtatctcttc ccttctccat tctttattgt gaagtttcat tgagctacta tatgagagtg   4260
ggcagaagag cgtagacgta ggtaaggcca ggagttgctg gctggactat attccagtgt   4320
gagaatacca aaccctcacg catctttctt tatcccaggt cacacttgta gctttgcctt   4380
gagttttgtt tgggtttatt ttctccctcc ctttccccct aagaagctat aactgcttat   4440
aaaggtagag agagagtagc caaaaccaat ccgtgagatc tcacagtgct aggcacgcat   4500
gcagctccca agtctcgcaa ataactatac tgtcagggat tacaataact atctccatac   4560
ataccaagct tggtggtgca cacctttaat cccagctaac aggaggcaga agcaagatct   4620
ccgagttgaa ccagcctggt ctacagactg agttccagga tagcgagggc taaacagaaa   4680
aaccttgtct ccaaatccca ataataataa gcaataatct tcattttgcg acataaacca   4740
aacgtagagg tacacacttg taatcccagc ctgggaggga gaggcggtat tagttcaagg   4800
tctttttaca tgctgagttt aaagccagtt tttgagatcc tgcctattta ggggagaatc   4860
taccttttta aatgcatgac caaaggagag aaaggcggcc tgggggtctg gggagatatc   4920
tttgctgggg ttctctaatt aaataaggtt ctctcatcaa ctctacacat tgggtttccc   4980
aggtgtcatt tgaacaaagc ccctaggctt taccattaca aatcctcatg aactcaccag   5040
ttctgtgctc agctacaatc aacaagagct tggagcttat agatgacgga ttctgtgctg   5100
gctatggaga ggatcaaaat ggagaactga ccagagaaga ccactcacac agggtttaag   5160
ccaagagaaa gtattagcca gccagtgtct acactggatg ttcagggtga cagtgtagca   5220
cttgagcctt tcttggggca agaaaaagaa aacataatct ggggtgacat tcaattaaca   5280
agaacagtta gccagaagtg gaacaacaga agctaaaaac aaggttagta cattagaaac   5340
tttccaagaa ctttggtaga ttagggattt gttttagttt tggcaggtgg tagtgtcagt   5400
gtgctgagtt ttacagccta aatggtattt ccatcatgga gtcagctgta ctaatgggga   5460
gggaggttac taaggtctgg gacttcatta aaagcacaag gaaaga                  5506
```

<210> SEQ ID NO 5
<211> LENGTH: 5421
<212> TYPE: DNA
<213> ORGANISM: Homo sapiens

<400> SEQUENCE: 5

```
gtgtcgtccg gggcgctgaa attcaaattt tgaacggccg tggtagccta ccgactccgt     60
gggtgcggag ggcagagccg actgggtgtg agagcgcccg ccgcctcgac tgcagtcctc    120
ctccaggagc tgcgccgagc ctgcactcac ttctttcctc ttcctgagtt tgaaccgtcg    180
gacccaccgt ctagccgtcc actggtgagg cctggggcga tggacccgtt taccgagaag    240
ttgctagaac gaactcgtgc cagacgagag aatcttcaga gaaaaatggc tgagaggcct    300
acggcagtag cgagatctgc cccgcatgcg aagagaggca gagagccact ttcagaagca    360
agtaatcagc agcagcccct accagggggc gaagaaaaat cttgtacaaa accatcacca    420
tcaaaaaaac gttgttctga caaaattgaa gtgggagctc cggacttaga aaatacagaa    480
cctattgatg ttgcaaagcc ctgttctccg atgcctgcac cccggcaggc gaagccccca    540
gcaccagctg ccatcagcga gtctgtggct gccccagcag ccctgctcag cgcggacaga    600
gggctgaact caggatccga agcatctgca acctcctcag ttaaaactcg aatgcaaagg    660
cttgctgagc agcggcgcca ttgggatagt gatctcacag atgatgtatc agaaagttca    720
tactttgcac cagtgccaac tgaggacaag gctgcctcac cttctaagcc acccatttca    780
aatgcctcag ctactccagt tgggagaagg ggccgtctgg ccaaccttgc tgcaacgatt    840
tgctcctggg aagatgatgt aagccactca tctgcaaagc aaaatagtgt gcaagaacag    900
cctggtaccg cttgtttatc caaatcttcc tctgcaagtg gagcatctgc tagcatcaat    960
agcagcagtg ttcagcagga agctacatgc tgttccccaa gggacggcaa tgcctctgtc   1020
aggaaagacc catcttcaaa tgctgcccat ggacctttgc ttagcgcctc agtgtccagc   1080
tctgtgaaag cgtcttcccc tgtgacagct gctaccttca tcactgaaaa ccgtgaggca   1140
caaaatcctg agctacttca caaaactgct agtcctctga aacagaggc gcggaaacca   1200
tgtgagaagc caactttgtc ccagggagct cagcccaaag aggaggctaa cagagaagtt   1260
tgtctacagt cacaatccaa ggacaaactt gcaacaccag gaggaagagg aattaagcct   1320
ttcctggaac gctttggaga gcgttgtcaa gaacacagta aagaaagtcc gtcttataga   1380
gcatctcata aaccccaaa tatcactcca aatacaaaag ccatccagga aagattattc   1440
aaacaaaaca catgctcgtc tactacccat ttagcacagc agctcaaaca ggaacgtgaa   1500
aaagaactgg catgtcttcg tggtcgactt gacaagggca atttatggag tgcagaaaag   1560
aatgaaaagt caagaagcaa gcatctagaa accaaacagg aagttcactg tcagaacact   1620
ccactcaaga aacatcaaac tgtcgcaagc accccattga cttctgtaac agataaggtg   1680
gctgaaaatg aaccagcagt gaagctttct agcacagagc ctgcaggttc cactgaaagc   1740
gaaatgacaa agtccagccc tttgaaaatc acgttgtttt tagaagaaga aaaatcctta   1800
aaagtagcat cagacctgga ggttgagcag aacactgaag cagtgcgtga ggttgagatg   1860
agtgtggacg atgaggacat caatagctcc agagtcatta acgacatctt cagtgacgtc   1920
ctagaggaag gggagctgga tgtggaaaag agccaagagg agatggacca agtgggagca   1980
gaaaacagtg aggagcagga agatgcgctc aatatctctt caatgtcttt acttgctccg   2040
ctagctcaga cggtcggtgt ggtgagccta gagaatgtaa tttcttcacc tccgtcggaa   2100
```

```
ttgagagact ctaacctaag cgctgcaagt cctaagcccg ggaaattcca gagaacccgc   2160
gtccctcgcg ccgaatctgc cgatagcctc ggttctgagg accgggacct tctctatagc   2220
attgatgcat ataggtctca aagattcaaa gaaacagaac gcccttccat aaagcaagtg   2280
attgttcgaa aggaagatgt tacttcaaag ttgggtgaaa agaaaaacgt attttctggt   2340
caagttaata tcaaacaaaa aatgcaggag ctcaataatg acataaattt gcagcagaca   2400
gtgatctatc aggccagtca ggctctcaac tgctgtgtgg atgaagaaca cgggaaagga   2460
tccttggaag aagctgaagc agaaagactt cttctgattg caactgagaa aagagcactt   2520
ctgattgatg agctgaataa gctgaagagt gaaggacctc agaggagaaa caagaccagt   2580
gtcatatccc agagtgaatt tgctccatct aaagggtcag tcactctgtc agaaatctgc   2640
ttgcctctga aggcagattt tgtctgcagc actgcgcaaa aaacagatgc atcaaattat   2700
tactacttaa ttatgctaaa agctggggct gagcagatgg tcgccactcc attagcaagt   2760
actgcaaact ctctcagtgg tgacgctctg acatttccta ctacatttac tctgcatgat   2820
gtttccaatg actttgaaat aaacattgaa gtttacagcc tggtacaaaa gaaagattcc   2880
ttgggccccg ataagaagaa gaaagcctcc aagtccaagg ctattactcc aaagagactc   2940
ctcacatcta taacttcaaa aagcagcctt cattcttcag ttatggccag tcccggaggt   3000
ctcggtgctg tgcgtaccag caactttacc ctagttggat ctcacacact ctccttatct   3060
tctgttggag acactaagtt tgctttggac aaggtacctt ttttgtctcc gttggaaggt   3120
cacatctgtt taaaaataag ctgtcaagtg aattcagctg ttgaggaaaa gggtttcctt   3180
accatatttg aagatgttag tggctttggt gcctggcacc gaagatggtg tgttctctct   3240
ggcaactgta tctcttactg gacttaccca gatgatgaga ggcgaaagaa tcccatagga   3300
aggataaatc tggccaattg tatcagtcat cagatagaac cagccaacag agaattttgt   3360
gcaagacgca acactctgga attgattact gtccgaccac aaagagaaga cgatcgagaa   3420
actcttgtca gccaatgtag agacacactc tgtgtcacca agaactggct ctctgcagat   3480
actaaagaag agcgggatct ctggatgcag aaactcaacc aggtcattgt tgatattcgc   3540
ctctggcagc ctgatgcatg ctacaagcct gttgggaagc cttaagccga ggagcttctg   3600
caccgtgaga gactttgcta gctgtgtctt cttaagaaga cagttagaag cagcagattt   3660
gcaggttgta ttctatgctt taaatataaa agggtatgtg caaatattca ctacatattg   3720
tgcagtattt atatcttttc tatgtaaaac ttcacccagt ttgtcttgca ttcgtacatg   3780
tttgacagtc aaatactaac aatattcatg agaattgata tccatgctaa atataacatt   3840
aagagtcttg ttttatagaa acctcactag ccagttattc atgacaaaaa ctattataat   3900
caagttctga tttgtccttt ggagctgtgg gtttgaaggt attaaggtct caaacagaaa   3960
catttcagga catgtttagt aaagagatga gaaaaggcag caaacactag tttaagctgc   4020
tcagagctgc tttccgcaga gctgtgggca ggacaccgta acatttgggc ctgcatagtc   4080
tatgctgaag ggttaagagt cacacagcta gtgctcactc tgaccctacg tgtgcagtgt   4140
ggggcacctt ctcacagtgc tcaggcttta ctaaagagtt ctttccatat ggcttagagt   4200
cctcatatta acattagctt ttctcttaca ataaggacaa atgtaagttg aagagcacgt   4260
gcataagagc ctgtaccaag ctgctggggc tactcctttg cttcccagag ttcctgtctg   4320
aggtcctttc atgtttatct atgacacttt ctacaactct gttctgagat cactgaaaaa   4380
tacagtaagc tacgtgttac ctttaaaagc ccaatgcctc cttgaaattt aaagatattg   4440
aatgcatggc ttcagttttt aaatagtttg tatttcttct ctgacttaat tattgatggt   4500
```

```
ttcatttata aacactaagt ctatcacttg ccattatatt tcttactcat ttaaatgtgg   4560
attttcttat gtatattata aaagtatttt atgacataaa taaataattg taaattgtca   4620
aaagcatcag ttatttaaga aattctctgt gtgatgtatt gctgtgtatg tcctggttgt   4680
gtggggggca ttgtgctgac actaggccat ccatatcttc atatctagcc cagtctctgt   4740
cttgctgaat gttcttgggg ttggtgttac atgagcaggt atgtgaagga ccctttctgg   4800
gggtttcagc agaatgtgat gatgggtgca catttgagga ggtgatgggt gagactgagt   4860
ggtcagcagc tagaacaggc aggcgcgagg tgaaaggagc gatgaggtgg ttctttgtac   4920
aaggctgttg gctcacattt gcaacagctg gagagcacaa agacgttaca cagatatctt   4980
ctcctgttct caggcttccc tttgtacttt tcacagcata gactgtgcaa atagtcttta   5040
cagacatgta cagtcttcta tatgtaagtg tcctgtacac actgcttgtt atatagtacc   5100
ccttaaaggt tgtctcagtt tatatataaa attcagtttt agaagtttac aatatatgtc   5160
attcctttta atggttaatg aaataatcta aaaatcaccc gagtagaaaa attcaattta   5220
tatatttatt tgtgtgtgtg tgtgtgtgtg tatgtgtgaa agagaggcca tgtatgaaaa   5280
tatgatacaa tccattacta tgtgtaatat ggtaacagat actaatatat tataaagctc   5340
cgttcttaca gatatctgta gataaaggta aacacaaaag gttaatattt atgacataat   5400
aaaagaattg atgtgcaaaa t                                              5421
```

<210> SEQ ID NO 6
<211> LENGTH: 2966
<212> TYPE: DNA
<213> ORGANISM: Homo sapiens

<400> SEQUENCE: 6

```
agtttatagt gtgtcgctgc cacgcctagc gggtttaccg cctccctcct ccccctcgcc     60
ctcccgctcc caaccctttg ccttccaaac aatttaaatg tcgcacagaa ccaacctatc    120
gcaagcctcg ttcgagggga aggggcggga gcttccggaa gtgttggcaa aagtccctcc    180
aatcagcggc tggcagcggg aaatttcagt tccgtgaagg gtcggtccgg gagttccttc    240
tgcggatcgg tggagttttc tgtgttgcga cattgttgtg gatccagaaa ctgcttcagg    300
atgctggtgt cacgttttgc cagtcggttt cggaaagact cgagcactga gatggttaga    360
accaacttgg ctcatagaaa gtctctgtct cagaaggaga acagacacag ggtgtatgag    420
cgaaacagac acttcggttt gaaggacgtc aacattccac tggaagggcg agagcttggt    480
aatatacacg agacatcgca agacctctct ccagagaagg ccagctccaa aacaaggtca    540
gtaaaaatgg tcctgagtga ccaacggaag cagctcctcc agaagtacaa ggaagaaaaa    600
caacttcaaa aactgaaaga acagcgagag aaagccaaac gtggagtgtt caaagtgggt    660
ctctatagac ccgctgcgcc tggctttctt gtcacagacc agaggggtgc gaaagctgag    720
ccagaaaagg cttttccaca tactggacgg attacaagat caaagaccaa agaatatatg    780
gagcagacta agattggtag caggaatgtt cctaaagcaa cccagagtga ccaaagacaa    840
acttctgaaa aacaaccatt agacagagag agaaaagtta tgcagcctgt gctgttcacg    900
tcagggaaag ggactgaatc agcggctact cagagggcca agctgatggc ccgaacagtg    960
tcatccacta caagaaagcc agtcacaaga gccacgaatg agaaaggatc agaaagaatg   1020
agaccaagtg gagggagacc tgccaaaaaa ccagaaggca agccggacaa ggttattcct   1080
tccaaagttg agcgggacga aaagcatttg gattcgcaga ccagggaaac aagtgaaatg   1140
```

```
ggtccgctcg gagtcttccg agaagtggaa agcttgcctg caacagcccc tgcccaaggg   1200
aaggaaagga agtcctttgc ccccaagcac tgtgtcttcc agcccccgtg tggtctgaag   1260
agctaccagg tggctcccct gagccctaga agtgccaacg ctttcctgac acccaattgt   1320
gattggaacc agttaagacc agaagttttt agcactacaa ctcaagacaa agcaaatgaa   1380
atcttggtac agcaaggatt ggagtcgcta acagaccgta gtaaagaaca tgtcttaaat   1440
cagaagggtg cttctacttc agattcaaat cacgcttctg tgaaaggagt cccatgctct   1500
gaagcgagcg aaggccagac ctctcagccc ccccacgatg tgccatactt cagaaaaatc   1560
ctccaatcag aaactgacag gctgacctcg cactgccagg agtgggaggg gaagctggac   1620
ctggacatcc ctgatgaagc taaaggtctt atccgtacaa cggttggtca aacaagactc   1680
cttatcaagg agagattcag acagtttgaa ggactggtgg acaactgcga gtataaacgg   1740
ggtgaaaagg agacgacctg cacagatctg gatggattct gggatatggt tagttttcag   1800
gtcgatgatg tgaaccagaa attcaacaac ctgatcaaac ttgaggcgtc aggatggaaa   1860
gacagcaata atccaagcaa aaaagtcctc cggaaaaaaa ttgtgcccgg tagaacaagc   1920
aaagcaaagc aggatgacga cggacgagcg gcagctagga gtcgccttgc agccataaag   1980
aatgcaatga aggcaggcc acagcaggaa gtgcaggccc acgcagcagc tccggagaac   2040
acaaaggaag ttgacaaaat agtgtttgat gctgggtttt tcagaatcga gagcccagtg   2100
aagtcattct cagtcctgtc ttctgaacgt cgttctcaaa gatttggaac acctctgtct   2160
gccagcaaag ttgtgcctga gggcagggct gcaggggacc ttctgagaca gaagatgcca   2220
ctgaagaagc cggaccctca gagcagcaag agcgagcatg ttgatcggac gttttcagat   2280
ggtcttgaaa gcaggtgcca cgtagaagac accccctgtc ctggagagca agattcaagt   2340
gacatagagc atgatgtaaa taaaataaat gtcaagatgg attgtttctc tgttgaaacg   2400
aatttgcctc ttcctgctgg tgatgctaat accaatcaaa aagaagcaat ctcagctgtg   2460
gaaggagcga gctctgcagt cacctcccag gatttgctga tgagcaaccc tgagacaaat   2520
acctcctcac agagcaacac ctcacaagaa gaagctgagg cgtcgcagtc agtactgtta   2580
cataaaagtc tcacttctga atgccacctt cttgaaccac caggcctcag ctgcaccagc   2640
ccctgcactc gggaggagac cagacagcca gatcgcagca gacagttctc ctttggaggt   2700
gacctcattc tcttctcacc actatgaccc tgaagggaac accaggaggg ctttaaattt   2760
aacatgactt ttaatattaa tttaaataaa cattcagtgc tcgcctttaa tcccagcact   2820
ccgggaggta gaggcaggcg gatttctgag ttcgaggcca gcctggtcta cagagtgagt   2880
tccaggacag ccaggactat acagagaaac cctgtctcga aaaaccaaaa taaataaata   2940
aataaataaa caaacaaaca aacaaa                                        2966
```

<210> SEQ ID NO 7
<211> LENGTH: 773
<212> TYPE: DNA
<213> ORGANISM: Homo sapiens

<400> SEQUENCE: 7

```
gtgggcggac caatggactg acgggggcgg gctcttcgcg ggcggtgtcc taaaggctgc     60
gagggcggcg gcactggtta cggcgagtgg cgacccgcga tgaagccgcc catttcaata    120
caagcaagtg agtttgattc ttcagacgaa gaacctgttg atgaagaaca gactccaatt    180
caaatttcat ggctacctct gtcgcgagtg aattgttccc agtttctcgg tttatgtgct    240
cttccaggtt gtaagtttaa agatgttaga agaaatattc agaaagatac agaagaacta    300
```

```
aagagctacg ggatccaaga cgtgtttgtt ttctgcacca gaggggagct gtcaaaatat    360

agagtcccaa accttctgga cctctaccaa caatatggaa ttgtcaccca tcatcatccg    420

atcccagatg gagggactcc cgacattggc agctgctggg aaatcatgga ggagctggcc    480

acctgcctca aaaacaaccg gaaaaccctg atacattgtt acggaggact tggaagatcc    540

tgtcttgctg cttgtctcct cctatacttg tctgactcaa tctcaccaca gcaagccata    600

gacagccttc gagatgtcag aggatctggg gcgatacaga ccatcaagca atataactat    660

cttcatgaat tccgggataa attagctgcg tatctatcat caagagattc actatcaaga    720

tctgtgtcca gataatgaag atcccaaata aacgagcaca tctagggtct cca           773
```

<210> SEQ ID NO 8
<211> LENGTH: 2960
<212> TYPE: DNA
<213> ORGANISM: Homo sapiens

<400> SEQUENCE: 8

```
ggtgacgcct tcaccttaga ctcggaggac ccgagagggg agaacccttc caccacctga     60

gtgtcccact ccatggagga ggtaagagaa aaaggtgtat cacaagagtc acgacgtgac    120

tgggtctcca agaagcgaag actgcggcgc gagagagtcg ccatatttct ttgaagcgcg    180

cgcctctttc tcgcacgctc caagtcccgc ccacctgtct ccctgcgtct tcattggaca    240

atgttcctga aagacacgct ctcaatacgc tcagcgccag catattggta tagtttgcgg    300

aatagcggtc ttcagccaat cacgctactg gcccgcatcg gaaaccccac cctcgaggca    360

gttcaaccaa tgaacttaca gcagtcttaa tttaaactcc atatataagt cggcttgtca    420

acgtcttggg tggcgccagt tttgagccgc tctgttttga gttgtgtggc tgtttttctg    480

ggaatcaccg agattgcaga acgcgatgac cgtcccctct gcagaggagc tggactcctt    540

taagtacagc gacctgcaaa atttagccaa aaggctgggc ctccgggcta acatgaaggc    600

agacaagttg ttaaaagcct tgaaagcaca cctgaatcca gaaacaagga aagaaaataa    660

aaatcaggat gaaaatcaat tctccactga tgaaactgag atacacgtta gcagtgagga    720

gcaagctgag acggaatcag gtggtcacgt caccaaaacg aggaggagga ggaggaagaa    780

gcacaagacc atccatggaa ttcctacctc ccagactttg ttgcaggatc atttggagat    840

gaaaggaact gatagtagta acttccaaaa tcaagaaaat caggaaaatc aagaccccag    900

ggatacagca gaagttcctt ctctgccgga gcagaggcca gaggacggca atgcggcttc    960

ttcaggagaa ggagaagtaa atgacattaa agattcaaag aagcctttag aaaaaagatc   1020

tctatgcacg gatgagtttt ctaaacttgg gaacaataaa aggacttcag ccacaacacc   1080

aaactttaag aagcttcatg aggctcgttt taagaaaatg gaatccattg atgaatatat   1140

tatgaggaaa aagaaacacc ttaaagaaca cagttcactt aatgaactaa agcttgacaa   1200

aaaagggata gtgaccccag ttcctccaag aggaaggctc tctgtaccct gtactcctgc   1260

caggcagcag tgcccacaag gccactcagc aactaaaatg aatgtcaggt tttcagctgc   1320

tactaaagac aatgaacata agtgctcact gaccaagaca ccagccagaa agtctccaca   1380

cgtgactgca cctgggagtg cttcaaaagg ccaggctgtg ttcaggacac ccaagtcaaa   1440

ggccactgaa aggacttcta ttgcagttat taccccttc aagttgatga ctgaagcaac    1500

acagactcca agttctagta agaagccagt atttgatctc aaagcaagct tgtctcgtcc   1560

cctcaactac aagccacaca aaggaaagct gaaaccttgg ggacaagcta aagagaacaa   1620
```

```
ttctctgaac gaacgtgtaa gcagagttac cttccacagg aaaacttaca aacaacctca   1680
tctccaaacc agggaagaac gatggaagag acaagagcaa gaacgaaagg agaagaaaga   1740
aaagcttttg gaagctcgaa gaaacctggg tgtgactaaa gcccagtgac cctgtctgtt   1800
cctttactct aacttgtttt ccttttgtat gtttttttact ctttctctac ttcagtcaaa   1860
agctcttttc tatcataact tttggtcata atttgtgtag tgtctcttct gtgctatatc   1920
tgagaatata ttatcacctt aaagttcata actaaagtag ttttcatcta atgccctata   1980
catctccaat ttttaaaaga cttgtcctca tgattcttaa cagaggtttt tcatgtcaag   2040
gtcctgatag ttccgaggga gatgacctgc acccttttct gcacaagctg tagcagaatc   2100
ttagcatgag aaaataagat atcgctcata ggaaaaggga ggctggaaga ccacattttt   2160
gttcagtagc ctggaaaatc tattagtctt attgaaatct tattttatca aggtaaaaag   2220
ttttagctta taagagcctt gttctgactt ttcatgtatt tgccatctgt cattcattat   2280
aatcctaaac gagaaaacct ctactctctc tacttgttaa ataaaagcca cagggcaaag   2340
ggtgtgcttt agttgtacaa cacttgtcta tcacactcct gtccctgaac tgtaccacca   2400
aaaccaaagc tgagaattgc tgctgtaaga attactgtca ttggcagact tttttcttac   2460
aagtagtaaa gagaggaaag ctgcaagggg tgaccttctg atctttgctc tgccttacag   2520
agattctgag atgtgtgtaa tgcttacaat gttcataaat aaaaattttc actgtgatag   2580
gttcattgtt ttaagcgtaa gttgctcagg atttggatgg acatcagaga tcagtaaaca   2640
cacctcctcc atccacttgt cttccacaac tgttgagaca gggcctcatg tagggcaaac   2700
tggtcccaaa ctcattttgt atctgaagat gaccttgaac tcctgatccc ccagcctcta   2760
cctcccaggt gagtgcagag ttagatgtat accaccatac ctggctataa agaagtgttt   2820
ttgtttttcc ctttgttact gactacattt tgaatctaag gccttgcaac ttaccagaaa   2880
tagtacgata acaaggttaa taaccaacag ttctatttgt atatactata agtcaataaa   2940
gctaagctga atgtggtagc                                               2960

<210> SEQ ID NO 9
<211> LENGTH: 1541
<212> TYPE: DNA
<213> ORGANISM: Homo sapiens

<400> SEQUENCE: 9

ggtatttgaa tcgcggaccg ggcggtggac gcggagcggc ggggccctga ccctcccaac     60
ggtgtcgcag accggagtgg ctgtgcctcg tccgcacttg ccagggcggc cctcatggcg    120
ctgctccgac gcccgacggt gtccagtgat ttgaagaata ttgacacaga agttattcct    180
aaagccaaga gccatgtgac tatccggcgg gcagttttag aagaaattgg aaataaagtt    240
agaaacagaa ccactcaggt ggcgaagaaa cctcagaaca ccaaagtacc agctctgccc    300
accaaagtga caaatgtcaa caagcagccg aaacccacag cctctgtgaa accagtgcag    360
atggaggcgc tagctcccaa ggatcgtcct cccgcccctg aggatgtctc catgaaggaa    420
gagagcctct gccaagcttt ctctgatgct ctgctctgca agatcgagga catagataac    480
gaggacaggg agaaccctca gctctgcagt gactacgtga aggacatcta ccagtacctc    540
aggcagcttg aggttttaca gtccattaat ccacacttct tagatggaag agatataaat    600
ggacgtatgc gtgccatcct ggtggactgg ctggtccaag tccattccaa gtttcggctt    660
ctgcaggaaa ctctgtacat gtgcattgcc atcatggacc ggttcctgca ggctcagctg    720
gtctgccgga agaaactgca gctggtcggg atcacagctc tgctcctggc ttccaaatat    780
```

```
gaggagatgt tttctccaaa tatcgaagac tttgtttata tcacagataa tgcttacacc    840

agttcccaaa tccgagaaat ggagactctg attttgaaag agttgaaatt tgagttgggc    900

cgacctttgc cacttcactt cttaaggcga gcctcaaaag ccggagaggt ggatgttgaa    960

cagcacactt tagccaagta cctgatggag ctgacgctcg tcgactatga catggtgcac   1020

taccatcctt ctcaggtggc agccgctgcc tcttgcctgt ctcagaaggt gctgggccaa   1080

ggaaaatgga atttgaagca gcagtattac acaggctaca tggagagtga agtcctggaa   1140

gtcatgcagc acatggccaa gaacgttgtg aaagtcaatg acaaccgtac caagttcatc   1200

gctgtcaaga acaagtatgc cagcagcaga ctcctgaaga tcagcacgat ccctcagctg   1260

aactccaaaa tcatcaaaga cctggcctcc cctctgctgg gcagccccta gacactggac   1320

tgccatcctg cgcttctcag atcctgtatg tattttattc tagtttacat cacaaacctc   1380

ttctcaaact cattttctaa ttgtgtattg atgaaaaata aagctattga ttttcttata   1440

ctatcctgtg tatgtttgta tactctacac tgaagaaatg tagaatggcc tacaataact   1500

ctgctctgta ttgaaggaaa ataaagctat tgatctactt a                       1541
```

<210> SEQ ID NO 10
<211> LENGTH: 5938
<212> TYPE: DNA
<213> ORGANISM: Homo sapiens

<400> SEQUENCE: 10

```
gtgagctcac tcccgcctcc atgttcccgg agtcgcctgg aagcgtccgc ccaaggtcgc      60

gggccgcttg gggagtcagc agcgcgccag gccccttcgg gccccacacg cattaggtgc    120

cttcttgatg ggtacggagt gaacgcgggc ggcggcggga ccgaggcagc gcccagtttg    180

taaccgccgc gccgcccgtg cccgcgcgcg ccacacccca gcgcgcttcc ggccgggcca    240

cgtgaccgcg cgtgcacgtg ttccggcctc tccgcttcgc cgctccgaac ctcctcctgg    300

tcgtcccggc attcgtccac gcggagccgg cttgggcggg gcccgggagg cggcggccgg    360

agaagccgcg gagacgcgag cgccgagcgt cgcgagggag caggcccggg caggcaagcg    420

gcggcctccg ccatgaaccc caggggcctg ttccaggact tcaaccccag taagtttctc    480

atctacacct gcctgctgct cttctcggtg ctgctgcccc tccgcctgga cggcatcatc    540

caatggagct actgggccgt ctttgccccc atatggctgt ggaagcttct agtcgtcgca    600

ggcgcctccg tgggcgcggg cgtttgggcc cgcaaccctc gctaccgcac cgagggagag    660

gcctgtgtgg agttcaaagc catgctgatc gctgtgggca tccacctgct gctgctcatg    720

ttcgaagtcc tggtctgcga cagggtggag aggggcaccc acttctggct gctggtcttc    780

atgcctctct tcttcgtgtc ccccgtgtcc gtggctgcct gcgtctgggg ctttcgacac    840

gataggtcgc tggagctgga gatcctgtgc tcggtcaaca tcctgcagtt catcttcatc    900

gccctaaagc tggacaggat tattcactgg ccgtggctgg tggtgtttgt gcccctgtgg    960

atcctcatgt cgttcctttg cctggtcgtc ctctattaca tcgtctggtc cctcctgttc   1020

ctgcggtccc tggatgtggt tgccgagcag cggagaacac acgtgaccat ggctatcagt   1080

tggataacga ttgtcgtgcc tctgctcact tttgaggtcc tgctggttca cagattggat   1140

ggccacaata cattctccta cgtctccata tttgtccccc tttggctttc cttactaact   1200

ttaatggcca caacatttag gcgaaagggg ggcaatcatt ggtggtttgg cattcgcaga   1260

gacttctgtc agtttctgct tgaaattttc ccatttttaa gagaatatgg gaacatttca   1320
```

```
tatgatctcc atcacgaaga tagtgaagat gctgaagaaa catcagttcc agaagctccg   1380
aaaattgctc caatatttgg aaagaaggcc agagtagtta taacccagag ccctgggaaa   1440
tacgttcccc cccctcccaa gttaaatatt gatatgccag attaaactcc tagagaggac   1500
ccaggcacac acagactcca cttggccttc gcctcttgtt cattcatccc aaacctggaa   1560
atggaaacag gcttcaaaca ctcgtctcac gccgtgtttg agatcaccgc ctcatcagta   1620
tgcatcatag atggaggtgg tttcagtatg tgggtgtgtg tgatgtgtac ctgggtaaga   1680
gacttgcttt ccaggttcgc actttcaggt gtagctgggg gcagtaagtc gaattgtttt   1740
agtaggtcct caaaaggaat aaccacacag ctgtttgttt aaatgctact gtacctatca   1800
aaactattgt ttaaaaagta tttttataca ctgctaatct aaaattgtat ttcagattgt   1860
gcctgtcata acaatagcaa atgtaaaaag ttctctttcc caccacttgt ttataaacct   1920
catagttgat atttttagtg ttcctactgt taaaatactc tctccttggg ctttgctgat   1980
actggtcttt aatattctga taggtgaatt tttctaatgg aatgaaccca tgcatatata   2040
gtatttatat gaatatttta gcagtgtaat atgttgaatt ctagttctct gcattaccat   2100
tattacgtta aagtattttt taaagcttag gtgtgaagat atgtgtctat tgcagatgtc   2160
cttgaaaact gcataaaaca gtatgtgcct ggtgtggatc ttaccaaagt actaggcatg   2220
aatgtaggga ctgcaaatcc catgggtctt aatatttagg tgttagtaac caaggtctct   2280
ggtagtaccc gttagtagag gaagaggcca ctgcccttgg gaacttgtga caggctctag   2340
tgtggtacca ggccataaag tgacactgtt atttagcaac ttgaattttt ccacacaggt   2400
agtaactgtg tggaaataag caacaagtgg tttgtccatt tctaagaatc ttaaactatt   2460
agttggctgt agtgtgaagc attacttgtc attggaaaga tggagagagt ggccttaacc   2520
ggaagtggtc agtagaagca ggtgtcattt taagggccaa actttaatct gtcagcaata   2580
gggaaacaac tgttcaaatt atctttgtag ataagaacag tgtttctttt ttcttttctt   2640
ttgttttttt gtttgtttgt tttgttttgt tttgagacag agtttcactc ttgttgccca   2700
ggctggagtg caatggcaca atcttgatct cagctcgccg cagcctccgc ctcccggttc   2760
aagcgattct tctgcctcag cctcgcgagt agctgggatt acaggcatgc accaccacgc   2820
ctggctaatt tcgtattttt aatagagaca gggtttctcc atgttggtca ggctggtctc   2880
aaactcctga cttgaggtga tctgcccgcc ttggcctccc aaagtgctgg gattacaggc   2940
gggaaccact gcacccggca ggtacagtgt ttctttaggt gctggtggta caccagggaa   3000
tcagggcaga agctggatcc tgcaagagta atgtttgaga acaaataaat actttcgaaa   3060
ggaggtcgaa acaaaaagga gtgtaggtgt tattactgca gagaagactg aatggagtcc   3120
acttttctta ttagtaactt actaaaaatg atctcaaatg ggctccacac actttgccct   3180
ggccatgagg caaacttgtt gggtttggag aaaaacacat aaccctaaat tcactatttt   3240
tgccctatat aaaacattaa aataacatgc tctgtacaca tgctgtcaac aaaagccagc   3300
tctaggaacc tgagtgccag aatgcctgag ggagctacag ctgggcttag ttggctggga   3360
ttgagctcgc tgtctgaggg agctcgctct gtctctctca cactggcagt ttacaccagc   3420
cggcagccct gagcagcagt gggtgtaact ttttataaat aaggattcat tgattcattc   3480
atattctcaa tatttcttga agacctaccc cgagccaagc atggtgccag gcagtgggga   3540
tgcagtggag agcaaacagc cctgcccatg caaagtgtcc tgtacggtga gaagtgtgag   3600
ctgcacccac aaagggaaag agcccagtgc agcttttgca aaatgcaggg aaggatgctg   3660
ctagcctcag ggtgacctag aactttaagc tcatctttgt tttcaggagc ccagtgcctc   3720
```

```
ccctccaccc ctaaagaata tctcaaagac gtggattttc atttcagtaa gatttagggg   3780

tgcatgggca ggcagtgctg gaggaactgg gaggcaggtt tggaggctgc agtgggacca   3840

ctggcccctc ctggctacag tttcaggcca ggagcttgtt ggcacctggt gcaaactccc   3900

aaacctgagg ggtccccaca accccccagc ccatcttaac ttcctcttcc cccaagctat   3960

ctggtgttgg aaagccagca tctagtgtgg aaacaagctt tctcaccagg taggccatcc   4020

gctgtcagga ccattaggta aaaacagaag tgacaggttg taggaagtcg ttcgatctgt   4080

gaggctgcga gcacttcagt gcctgggatt tacctaactg ccatgaaaca ctgattatcc   4140

agcattcagc atgtgtcaga ttctgtaact atttctcctg tgatgtatca gtcagctttt   4200

gctgcaaaac agcatcagaa atctcagtgg tctacaacta gattcccatt cttgggtagt   4260

ctacaagttg gcttctaggt tatgctccag gctgggggtc tgatcacgtc tgctccacaa   4320

catgtcccgt attctgggtc cctggttgaa gcagcagctt accttgggcc gtgttctttc   4380

tcatggcaga agcacaggag gccaagccct accttgcaag cacaaataca gcccctgctc   4440

actttctgtt ggccacaaca catggccatg cctgacctct gtggggtgag gcagtgcatg   4500

gccaaggaac aagcacagtc cacacagggg gctgtcactc cgtgacctca gtattacaaa   4560

atggttctca aggagtcgca aaatgtgtgg cagatcatcc atgatttgtt tcccgtgtgc   4620

tttacgaata tcctgaaatt tttaaaagct gtttccatta gaagggatct gttggggatt   4680

tgaggtgaga tgagaaagac cctgcattcc agcccctcag ttagcagtgg tgaggccgga   4740

gtactccaca cgggacagtt ttaggaaagt gctggaatcc aaagtttctc cggagggcta   4800

tgcaaggcgc tttggaaagg cgaagcctgg gcgcagggag cccagccatg taggtagaag   4860

cagcagacgg tgagggaggc catccccacc tggccctgcc agggccctga ctcagtgaag   4920

gaagctgttg ggatacaggt cattcagccg ggcaggaaag atgggatgaa gcccagcaag   4980

ttcacaggga tccgggaagt tgtgtggctg gaaacccagg cagggctgca ccacagggac   5040

catttgctgg agatgcagca cttgccacag ccaccaccac tgacagcatg acacccacaa   5100

aaagggagcc tccagctgca cccctgctgc tgcgagtact tcctcagctg tctgccatga   5160

gcttaaggtt aagtaccagg agggaggata tgattgggca aacctcaggc atgtgttcat   5220

tctgtagctt ccagaacatg cgaggagaga gcatctggct cctttgtctc gaggaggagg   5280

gggcaggact ctgccagaac tcactcgata aaagattttc ccaaaaggaa gggtgttcag   5340

atgacaaaag tccactacac cactttcctt ggctatctga tgcaccccca tcttcccatg   5400

cgcgcacctc agaaatcagg ctcccacctg acataacaca accatgcctc acaaaaagac   5460

agtggtttat cccttcccta ggagaaaaga gaggcaatgc caagctgctt catcaactgt   5520

taatacttct tccagcccgc aacccaggat atctgcaggt gtctctccct ctggtttggt   5580

catggctctc tctgttctag aatgtatggg ttaaagtcgg ctgccacacc atgccctcgg   5640

cagtgtggtc caaggacccc tgagggtcct caaggtcctt cctttcccaa ccccacgtgg   5700

ttttcttcag tcaggatacc atactgcaac agaccgaagg cggaagcagc tatgaggatg   5760

cagcagcctt ctgttaagcc aggctttaag gatctgcaaa aatgtaaaac gatgccactc   5820

ctactgatga aatatattgt tttggaaaat ataggtttaa aaattttttt aaggtaacat   5880

gtaatggatg tatagtcttc aaatggatga ataaatgttt ttcagagtta ttggcttt     5938
```

<210> SEQ ID NO 11
<211> LENGTH: 464
<212> TYPE: DNA

<213> ORGANISM: Homo sapiens

<400> SEQUENCE: 11
gttttatctt tctctttgtt gcttgtttct accatgcccg agcctgcgaa gtccgctcct 60
gccccgaaga agggctccaa gaaggccgtg accaaggccc agaagaagga cggcaagaag 120
cgcaagcgca gccgcaagga gagctactcg gtgtacgtgt acaaggtgct gaagcaagtg 180
caccccgaca ccggcatctc ctccaaggcc atgggcatca tgaactcgtt cgtgaacgac 240
atcttcgagc gcatcgcggg cgaggcgtcc cgcctggcgc attacaacaa gcgctcgacc 300
atcacgtccc gggagatcca gacggccgtg cgcctgctgc tgcccgggga gctggccaag 360
cacgccgtgt cggagggcac caaggctgtc actaagtaca ccagctccaa gtgagttcat 420
ttaactcaca ctcctaaccc aaaggctctt ttcagagcca ccca 464

<210> SEQ ID NO 12
<211> LENGTH: 3669
<212> TYPE: DNA
<213> ORGANISM: Homo sapiens

<400> SEQUENCE: 12
ggggagcggc gaggctacgt ctgcgtcaag agacgttaaa tttgaaactt ggcggcccgt 60
gcgtgatggg ggcgtgagga ggctattctg agaaggaatc gggtgcgtgg ttttgtttag 120
gagcacgggg tgacgatctt cgcagctcca gagccagctg aaggttgagg gagactcagt 180
tagcactcgg aggataaagg tctgcggaag ggcgagagca agtattggga atgcaggatg 240
gcggaggcga gtgaagccat gtgcctggag ggagcagagt gggagctgag taaagaaaac 300
atacagccct tacggcacgg gcgggtcatg tccacacttc agggagcttt ggcaaagcaa 360
gagtcagccg gccacactgc tctgcagcag cagaaacggg catttgaatc tgaaatccgc 420
ttttactctg gagatgaccc tctggatgtg tgggacagat atattaattg gacagaacag 480
aactaccctc aaggggggaa agagagtaac atgtcagcgt tagtggagag agcgatagaa 540
gcactccaag gagagacgcg ctattataat gacccccgct ttctcagtct ctggatcaaa 600
ttgggacatt tgtgcaatga acctttggat atgtacagct atttacaaag ccaaggaatt 660
ggcgtttccc ttgcccagtt ctatatttca tgggctgaag aatacgaagc tagagaaaat 720
ttcaagaaag cggacataat attccaggaa gggattgaac gcaaggctga gccccctggac 780 agactgcagt cccagcacag acagttccag tctcgagtgt cgcgacaagc tttcttggcc 840
cttgggaatg aagaggagga ggctttggag ccttctgaac cacagagaag ctcgctagct 900
gagctgaaga gcagagggaa gaagatggcc agagcgccca tcagccgtgt cggaggtgct 960
ctgaaagctc caggtcagag cagagggttc ctaaatgcag ttccccagcc agtacacggt 1020
aatcgcagga tcaccgtttt tgatgaaaat gccgataccg cgtctagaac ggagttatct 1080
aagcctgtag cccagccatg gatggcaccc cctgtgccca gggccaaaga gaacgaactt 1140
cagccaggcc catggagcac agacaggccg gcgggacgca ggcctcatga caatccagcc 1200
tctgtgacgt cgattcccag cgtgcttccc agctttacgc cgtacgtgga agagagcgcc 1260
cagcagacag tcatgacacc atgcaagatt gagcctagta tcaaccatgt tctcagcacc 1320
aggaagccag ggagagaaga aggagacccc ttgcagagag ttcagagtca tcagcaaggc 1380
tgtgaggaga agaaggagaa gatgatgtac tgtaaggaga agatctatgc cggagttggg 1440
gagttctcct ttgaggagat ccgagctgaa gtgttccgaa agaagctgaa agaacgaagg 1500
gaagccgagc tgttgaccag tgcaaagaag agggaggaga tgcagaagca gatcgaagag 1560
atggagagga ggctgaaggc aatgcaggct gttcagcaag aaggagctgg gggccagcaa 1620
gaagagaaga tgcctacaga ggacccagcc agattgcaga ttgcttcggg gcctcaggaa 1680
atgtcgggag ttcctctgtc ctgttccatc tgtccactaa gctcgaatcc tagggaaatt 1740
tcacctgctg agaacatttt gcaagaacag cctgattcta aaggttccag tatgcctttc 1800
tccatttttg atgagtctct ttcagacaaa aaggacaaaa gtcctgctac aggtggtcca 1860
caggttctca atgcccagag aagacccctt tcagttctca aaactacaga agtgggcacc 1920
acaaatgagg atgtgtctcc cgatatttgt gatgaactca cagaacttga gcctctgagt 1980
gaagacgcca tcatcactgg tttcaggaac gtcactctct gtcccaaccc tgaggacact 2040
tgtgactttg ctagagcagc tcgtttggca tctactcctt tccatgagat actgtcctcg 2100
aagggcatcg ctgctgatcc cgagggactg ttgcaggaag aggatctgga tgggaaggcc 2160
gccgaggctc atcacactgt tcatcaccag gccctcatca taaagaaact gagcccaatt 2220
attgaagaga gccgtgaggc cacccactca tctggcttct ccaggtcttc ttcctcagct 2280
cccagtacat cctccatcaa aggctttcag cttctggaaa agctggagct gactaatgac 2340
ggggcagaag atgctattca gtcaccctgg tgttcacagt atcgcctaca actgttaaaa 2400
tccctactag aattaagtgc ttttgcggag ttttctgtgg aagaccgacc gatgcctgtg 2460
ctggaaatag ggaaggagat tgagttaggt cctgaggatt acgtcatcaa gcaagagcac 2520
ctaacatgtg acgattacag gttattctgg gtggcaccaa gaagctctgc agagctaacc 2580
atgataaagg catcatctca gcctatcccg tgggattttt atatcaacct caagttgaag 2640
gagcgtctga atgaggacta tgaccagctt tgcagctgct gtcagtacca agatggccat 2700
gttgtttggt accagtatat aaactgctcc acccttcaga atcttctcca acacagcgaa 2760
tttgttactc atgaaataat agtgttgatt atttacaacc tcttgacaat cgtggagaag 2820
ctacacagag ctgaaatagt acacggagac ttgagtccac ggagtctgat cctacgaaac 2880
agaatccacg acccctatga ctatgtaaat aaggacgatc acgctgtgag gatcatggac 2940
ttctcctaca gtgttgacct gagggtgcag ctggatgcgt ttgcctatag tggctttcgg 3000
actgcacaga tcctggaagg acaaaagatc ctggctaact gttcttctcc ctaccatgta 3060
gatctgttgg gtatagcaga cctagcgcac ttactcctgt tcaaggagca cctccatgtc 3120
ttctgggatg gactcctctg gaaacttagc cagagcacct ctgagctaaa agacagtgaa 3180
ttgtggaata aattctttgt gcggattctg aatgccagtg acaagtccac agtgtctgtt 3240
ctgggggagc tggcagcaga aatgggtggg gcttttgatg ccacattcca tagccacctg 3300
aacagagccc tgtggaagct ggggaagaca atcagcccgg aagctttgct cactcagcaa 3360
gacaagcagc caggcggctc ccagagccct gcctaagcca tgggtatggt gaagaactgg 3420
tctggggctg ctgtgatttg tttagagcac acttagacac atcagcagtc cttcactagg 3480
ggtcactctc agtagcacag ctttcagcca ggtggctgtg ccctggcagc ctcatctggt 3540
ttattcaaaa ggtttctgtg cagacagctg ctttttagcc ctctggcttc tgccttctct 3600
cttttgtaat tttataacat gtactctcct ttcactgtgt attttataat aaaatagttt 3660
ttgttacat 3669

<210> SEQ ID NO 13
<211> LENGTH: 4532
<212> TYPE: DNA
<213> ORGANISM: Homo sapiens

<400> SEQUENCE: 13

```
gtttttacgg tggtgatcga gacgcgagga gtgtgcactg agcgacacgg ccctgaagag     60
tgcaaagctc cgcgaggtct ggtgtccaga gagttgtgtg gccatcatgc ctcaaaccag    120
atcccagaca caagctacca tcggttttcc gaaaaagaag ctatctaata ccctgaagaa    180
acccaattcc cgggattgtg aagtaaaact tagaaacgtc cagcctgtac ccaccactcc    240
gtgtgtggac gtaaaacttc tgcctctcag tccccgaaaa cgtctgggcg atgacaacct    300
gtgcaacact ccccggttat ctccctgttc tccaccaaag ctgggcaaga aagaaaacgg    360
accccctcgc tcacatacgt ggaaggggtg cagattagta ttcgatgatg agccgacatt    420
taaggcttcc cccccaaaag aacaagacag agttcgccaa caccagatac gttcctcctc    480
cgctcaaaga agtccagaga gcaaagcaga tcctgagcag aaatgtccgc cggagaagga    540
gtctgtgtgt ataagactgt tcaagcaaga aggcacttgc tatcagcaag ccaagctcgt    600
cctgaataca gctgtcccgg atcggctgcc tgccagagag caggagatgg gtgtcatcag    660
gaattttctg aaggagcaca tctgtgggaa gaaagctggc agtctctacc tttctggcgc    720
tcctgggact ggaaaaactg cctgtttaag ccggattctg caagacttca agaaggaagt    780
aaaaggcttt aaatccatcc tgctgaattg catgtccctg aggagtgccc aggctgtgtt    840
cccagctatt gctcaggaga ttggtcggga ggagctgtgc agaccagctg ggaaggactt    900
gatgagaaaa ctggaaaagc acttgacagc agagaaaggc cccatgatcg tgttggtgtt    960
ggacgagatg gatcagctgg acagcaaagg gcaggatgta ttatacacac tgtttgagtg   1020
gccgtggcta agcaactccc gattggtgct cattggtatt gctaataccc tagatctcac   1080
ggacagaatt ctgccgagac ttgaagctag agaaaactgt aagccgcagt tattgaactt   1140
cccaccttat accaggaatc agatagctgc catcttgcag gatcgactta gtcaggtgtc   1200
aaaagaccag gttctggaca gtgctgcgat ccagttctgt gcccgcaaag tgtctgctgt   1260
ttcaggagac atccgtaaag cgctggatgt ttgcaggcga gctatagaaa ttgtggagtc   1320
ggatgtcagg agccagacag tcctcaaacc actctccgaa tgtaaatcac ccagcgagtc   1380
gccggtcccc aagcgcgttg gtcttgctca catatcccaa gtcatttcgg aagttgatgg   1440
gaacagggtg actttgagcc aagaaaacac acaggattcc cttcctctcc agcagaagat   1500
cctggtttgc tctttgctgc ttttgacccg gcggctgaaa atcaaagagg tcaccctggg   1560
gaagttatat gaagcctaca gtagcatctg tcgcaaacag caggtgacgg ccgtagacca   1620
gtctgagtgt ttgtcccttt caggactcct ggagtccagg ggccttgtgg gattaaagaa   1680
aaataaggag agccgcctca ccaaggtgtc tctgaagatt gaagaaaagg aaatagagca   1740
tgtcctgaac ggcaaagctt tcaccgggaa catcctcgct gctggtctgc cctgaatggc   1800
tcttactcat ggcacttgca ggtgtccctc ccactggcat ttgagagccc ccagaatctt   1860
cattttagta aggtcgtttg gaaacagtta cggccttttt tactccgcac cagtaaattt   1920
tagtgtatgg attcatgagt gttagcgctg gctgatatct ttggttctta ctggttttac   1980
ccataaaaat gaccgagtag ctgggtgtgg tgacttttat gcctgtgatc ccagcacttg   2040
ggaaatagag tcaagagtta aaggccatcc tttgctacat agtgagcttg agctggcctg   2100
gactacatga gactctgtaa gaataaaaac agtggccctt tttaaagcaa tgttcagtac   2160
ttttcccctt tcacattcct aaacacagtg cctacgagta tatacggact tgtgttggag   2220
agtgtgtgta tgtattacct ctgtctacaa aggatatatt ttgtaaagaa ctttgaagtt   2280
tagaaggatg aaatggaatg atccaggaaa atttacgagc ctccgtggaa gggcattgtg   2340
```

```
ttcagaggat gcctcattca tgtgacaggt gttgctgccc tggacttttt aaggactgat   2400
gaagaatctc ccgtgctccc caccagtatg gggtgacga ggagaataac tacagattgt    2460
gaatatattt attttcaagt ttcgtttgtc tgggctgcat ttgttgtctc tgggttttcg   2520
ggcacatagg tgttcatatc cgagtcaagc agcaggagtc gctgtttgcc ttctacggtg   2580
tggaccgcta ggactgagct cgggccatca aacttggctg gcgaccagcg cctacccttc   2640
aagccatttt atgggtttgt gttcgtcttt ttaagcagcc acactccatg gtagcttagg   2700
ttttcagagg ttaataagaa aataccttct catcgggcct tggtagtaca cacccttaaa   2760
tcccagcccg caggtgatag atagaggcag gcgggtccct gtgtttcaga catgttccag   2820
gacagtctgg tctacagaga ctccagaaac aacaacaaca aaattaaaaa taactagcaa   2880
gtggaaatac tctctcacac tttgcctcag ggttagcttc cctcagacag agccattgtt   2940
tcaataggat gcagctccgg atgaattttc atctgagccc ctctttctag gctccctaga   3000
gaagttcatc ttcctggcat caagtggcag tttgtgacag ggacaccaga gggcaccatt   3060
acaacgccgc tttgaaagtg tggcccgggc aagggtggtt ttgagggaag gggcaggaag   3120
gtgcctgagt ccgacttgtt tgggaggttg ctgatgcatt cgtacctggc taagtgcttg   3180
ggagcaaacc atgcctggga tgaactgtct gagtctttgc ttttctccag gcgaggctgc   3240
tgccccgatg cctgatccgg ccccgagctt gggaatctga tatgggtaca ggagatctgt   3300
tggccactgt ttgatgcagc ctgcacatta tccttgtaaa gcgatctgaa ccccacagca   3360
ggtgggatgg gatgggatgg gatgggatgt gctgggatga gataggaggg ctcgctcgac   3420
gccctctgag atgcacactg cccactgcag aagactgtag agaggagatt ggatgccaag   3480
cactcactca tagaatacac attccctctg gggcggtgca caagaccata ctctcccaag   3540
gagtttggag agagtctgga actgtaaggg ttaacgagca caactgtaaa gattgtccga   3600
agactgatgg gaagcagaga ccgaatggga ttgagaacag atgtgaggct tgatttaaat   3660
tacattttat tggatgctgc agccttaaga gacgtgactg ctttacagtt tgtttccaca   3720
ctgtgggcag ctgctgtctg ttctgtgtcc atagtaggat cctgcccaaa gaggagcggc   3780
ctccccgcct ccgatgtagt tgaggcttgg cgccttcctc ttaactgcag ggcttgagtc   3840
aggaacaggg tttgactctc agtgggactg ggctgtatcc tccctggctt ctagccaaga   3900
ttgcatttac agattcaaag gggccaagtt ccttcccctc tctctgtctt ctccccattt   3960
ggaaataggg ctttctgtgg actgttttgt ttccttcagc acacacacac acacacccca   4020
cacacactgt cgatttctag gtcattgcta ctcttaaggc ttcagcaatt ggaacagggt   4080
gggttgtgtc agtgatgcgt gaagcagact tagagtccct gcttggcttc cgctgccctt   4140
gtgggagcag aggctgatgt atgtttgtca gcaaagtctt aagtgtaatt cagacgccga   4200
ggcggaaagg aggagagagg cctttccttg ctgcttttc tcaccgaagc tggaagctat    4260
gggaaggtgg tgggagttta agtggaaagg gatgggcctg tggttgctag tttttgccag   4320
gatcttaggc cacatggcgt agtggcaaag atgctgacct acatttcctc cttttgaaga   4380
cactggggtg tgtgtatcct ggtttgtcat tattattatt gttattattg ttgttgttgt   4440
tattttaaga accagattaa gtttccatag tgtcaggtat cgctatggaa agaacataga   4500
ctcaataaag ttggtatgaa ttccaacccc aa                                 4532
```

<210> SEQ ID NO 14
<211> LENGTH: 2775
<212> TYPE: DNA

<213> ORGANISM: Homo sapiens

<400> SEQUENCE: 14

```
acccttccg  cgagcagcac gcctgaaccc cacggatcgg atcggcggcg gcggcggcgg      60
cggcggccaa gcccgggagg cggcggcggg acgcgggagg cggtggcggc ggtggcggtg     120
cgcggagacg tagcagcggc agcatgtcgg ccggcggagc agtcccgccg cccccgaacc     180
ctgccgtgtc cttcccggcg ccccgggtca ccctgcccgc tggccccgac atcctaagga     240
cgtactccgg agctttcgtc tgtctggaga ttgtgcttgg aggacttgtc tggattttgg     300
ttgcttcctc caatgttcct ctacctctgc tccaaggatg ggtcatgttt gtgtcggtga     360
cagctttctt cttttcgctt ctcttcctgg gcttgttcct ctctggtatg gtgactcaga     420
ttgatgccaa ctggaacttc ctggattttg tctaccattt catagtcttt gtcttctact     480
tcggagcgtt tttactggaa gcagcggcca cctccctgca tgaccttcag tgcaacacaa     540
ccatgactgt gaagccacta ctcaacgaca accagtataa catcaacgtg gccgccacag     600
tttttgcctt catgacaaca gcttgttatg gttgcagttt gggtctggct ttgcgaagat     660
ggcgaccgta acactccttg gaaactgaca gttgtgtgct ggtttcattt gtctacttta     720
tatgtctgat cacttgggta ccatttgtcc caatataaca ttccaaacat tgttagctta     780
gtacagagag gacctcagtg caagctgtgg tttgttacat gggtgggatt ttcattttgt     840
tctgatgtta gagaagtatc ctttcctttt tcatctctcg tttcttttta aatgcatttc     900
cattgtatat tcttaaaata cacaggcact gttcacaaaa caatagtatt cctttttttt     960
ttttttggtt gagtcacccg aaccttaata atagtaaata actaaaacaa tacatctcat    1020
gcaggcttct catctaattc tatctttagt ataaaacagg aaatgataca catgtttttt    1080
ttacaaaaag gccaggtagc acatatgtag gctttaatag gccatatagc ctctgtggca    1140
attgttccat cctatgataa cataaaagca gctacagatg atgtgtaaat aaatgtctgt    1200
atcctaataa agcttatttc aaaaagggag caaaactgga tgtggtctac agaccataat    1260
tttatcaact actgccataa aaaccttagg tgttctgtgt tctattgaac taatcatgaa    1320
acctcattag acaagccaca taacatattt tgtttcatta tgcatcaatc acattgcctt    1380
tgtttaatag tcaaatatta cccttggaag gtcatataat ttctcaagct aaccccagca    1440
gagccttgga tgaagagcaa aataaggtag gaaataaact ccaaactaat gatttcctaa    1500
tagctcagca aggcactcac acgagagtac ttaagacatg atccccagag gcaattaatc    1560
actactggat ctagtatctt gctactgatg tctttctttt ggtttattta tgccatagac    1620
tgtggttgtt tggcctatgc atgaatatat aaatatttat gtatgtaaag cttttccaaa    1680
tagctctctg aagagttgaa tttttaactt cttattgttt ttgcattgct ttctgagctg    1740
aatttgagta acagattaac tataacataa agctatagat tcttacatgc tttgataata    1800
gcccagatat ctatgttgtt tttacattgg tgtcagacag gcaaaggaca tttaacacaa    1860
gagctaaaac aaaaactgga tctggctgaa tagaacagaa aacaatccta gtccacctgt    1920
atgtgtcgca ggcttggcaa cagatcatga gtgaccacag ttcccaccgc attctcatac    1980
aggccaattc cctattgttt tagtagggct gcctttggaa atggaggctt gggaattgct    2040
ctcgagctga cccatcacct aagagtgcca tgtatggttg gagtattgga ctccctggaa    2100
catagtgaaa aacatgaatg aatagcatca atgcccagtg ttcaagtgct gtttatctaa    2160
tactccccca gaagaagaac caacggggac ctcagtttgt aatacagctg aagacgagat    2220
gtatttctat atgtaggttg aagaaatcag tcttatggct ttccactcat gtcttagctc    2280
```

```
ttctaaaatg ccagacttcc ctcctgtttt tccagctcca gaccacacac tgaaaaacct   2340
gtattatgaa ttatatacta tgaagtcaca aatgtgccat aaagatacat tgtacgtgga   2400
atcactaaaa tgtagtccac tagaatttag ttgagatttt tgttttcccc caggtgtacc   2460
aagccatgct cagtgtggta ttaactcaaa tgaattcatt cagatgtatt ggtggtactt   2520
ttgtaaatgt atggcttcta ggttagcaaa aagaaaactc aaagctgact aactgtgaat   2580
acttaggtct gtagattcat tgcattctag atgttgtgag ctgagcgatg aagcacttga   2640
acaaagacga aggtgtttaa gaatctctct acgtatctta gctgtaaaaa tgaaaaagtg   2700
ttggctggtc ttaaaatctg ataaatttat tttataagtg ttatgactct aataaagtat   2760
tcatttgata acctt                                                     2775
```

```
<210> SEQ ID NO 15
<211> LENGTH: 2748
<212> TYPE: DNA
<213> ORGANISM: Homo sapiens

<400> SEQUENCE: 15

gcgagcgggg cgcgcagcgg ttactctggt tactgtccgc gagggatgct ggggacccgg     60
cgggcaggag ccttcgcctc gctctgaagg acgctcatcc gagacagcca ttcactctcg    120
aggaaggcaa gtgtcggtcg gacaggttcc cggccgtgac ttcggggctt gcttgaggag    180
gaatctccaa gggagggctg agctgccagg ctgccgccgc gcttcgggac gccgtggcca    240
tcttttgttg gagaaggctg ccggggcagt gttgctaagg gcagctttcc cagcacccag    300
atccttctac gctcccgact ccttcctacc gagcacctgc tgctggtgac aaaagaccgt    360
ttacagccag gcgagcggac atcgaagtat acagccacat tcgcacccct cagcccaata    420
gagaggcccg tgtccatcag ttggctgaat gaagaagtgt gtaatcagga gccgttgggg    480
taggcaggct ttaaatgctg ccttttaaga tctggacaac ttaagataca tttgcactct    540
caatgatttc aaaaattgat cacatctgac tcgtgatcct gaaactattt attggaagaa    600
gttcgaccgg ttgccccgaa cccctttgag aactacattt tggggacatt ttaatcactg    660
aagaccttcc gaggaaaaaa gacccccccca agagaccccc aaaacacaaa atcctcagcc    720
ttggctggtg ccaccaaaga agccttttga gccatgtgga cttttcttgg cattgctacc    780
ttcacctatt tttataagaa atgcggggat gtcaccctgg ccaacaagga gctcctgctg    840
tgcgtgctgg tgttcctgtc gctgggcctg gtgctctcct accgctgtcg ccatcgacac    900
gggggcctcc ttggccgcca tcagagcggc gcccagttcg ctgccttctc ggatattctc    960
tctgctttgc ctcttattgg cttcttctgg gccaagtcac ctgaatcaga aaagaaagaa   1020
cagctggagt ccaagaagtg cagaaaagaa atcggtcttt cagaaacgac attaacagga   1080
gcagctacct cagtgtcgac ctcgttcgtg acggacccgg aagtgatcat cgtgggatct   1140
ggtgtgcttg gatctgcctt ggcagcagtt ctctccagag atggaagaaa ggtgacggtc   1200
atcgagagag atttaaaaga gcccgacagg atagttgggg agctgctgca gccaggaggc   1260
taccgtgttc tccaggagct gggccttgga gatacagtag aaggtctcaa tgcccatcat   1320
atacatggct acatagttca tgactatgaa agcagatctg aagttcaaat tccgtaccca   1380
ctgtcagaaa ccaaccaagt gcagagtgga attgcttttc accatggccg attcatcatg   1440
agtctccgga aagcagctat ggcagagccc aatgtaaagt ttatagaagg tgttgtgctt   1500
cagttactag aggaagatga tgctgtaatc ggcgtgcaat acaaggacaa ggagactggg   1560
```

```
gacaccaagg agctccacgc cccgctcacc gttgttgcgg atggactctt ctccaagttc   1620
aggaagagcc tcatctccag taaagtctcc gtttcttccc acttcgttgg cttccttatg   1680
aaggatgcac cacagtttaa acccaatttt gcggagcttg ttctggtcaa ccccagtcca   1740
gttctcatct accagatttc ttccagtgaa actagggtac ttgttgatat tcggggagaa   1800
ttgccaagaa acctaagaga atacatggct gaacaaattt acccacagtt acctgagcac   1860
ctgaaggagt catttctgga ggcctctcag aatggtcgtc tgcggaccat gccggccagc   1920
ttccttcctc cttcctcagt gaacaaacga ggcgtcctta ttctgggaga tgcgtataac   1980
ctgaggcacc ctcttactgg tggaggaatg acagttgctt taaaagatat aaaattgtgg   2040
agacaactgt taaaagacat tcctgacctt tatgatgatg ctgctatttt ccaggccaaa   2100
aaatcattct tttggtcaag aaaaaggacc cattcctttg ttgtgaatgt attggctcag   2160
gccttgtatg aattattttc agctacagat gattccttgc atcagctccg aaaagcttgc   2220
tttctgtatt ttaaacttgg tggagagtgt gtgaccggtc ctgttgggtt gctttcaata   2280
ttgtctcctc accctctggt gttgattcga cacttctttt ccgttgcaat ctacgccacg   2340
tatttctgct tcaaatcaga gccgtgggct acaaaaccac gggccctttt cagtagcggt   2400
gctgtactgt acaaagcgtg ttctatccta tttccactca tctattcaga aatgaagtat   2460
ctggttcatt gaaagggagt ccacgtgcag tcaagtccct tggggcttga agaggatgta   2520
tatagcatag aactgtgtca cttccacagt ggacttgagg accaagcttg tgtataagca   2580
tgtaaatata agccttactt tacagttgaa aatgaaggtc agagaagcta gatgtttaaa   2640
aggatgattg tttctacaaa tcagtgctaa cactcaagtt tttcttttga tttcagtatt   2700
tggggtgact cattgggaca agccaataaa atgaagagtg aactctta                2748
```

<210> SEQ ID NO 16
<211> LENGTH: 3439
<212> TYPE: DNA
<213> ORGANISM: Homo sapiens

<400> SEQUENCE: 16

```
tgtttgaaat gcgccgggcg ggcgcacact tgggcttgca gcgtcgccgc cgggctctcc     60
tcagattgag tcctggtccc cgcggccgtg gtttgctcgg cttagttccc gccagccttg    120
ctcctgtcgg agcccgacgt cccgcgcgcg cgtcaggata gcacggagcc tgcggtcatg    180
aagtcagcga aggctaagac ggtcagaaaa cctgtaataa aaaaaggatc tcagacaaac    240
cttaaagatc cagtgggggt gtactgtagg gttcgccccc tgagctttcc tgaccaagaa    300
tgctgtgtgg aagtgatcaa tagtacaacc ctgcagctcc acactcctga gggctatcga    360
ctcaacagaa atggggacta taaggagact cagtactcat tcaagcgggt atttggcact    420
cacaccaccc agaaggaact tttgatgttt gtagctaatc ccttggtaga tgacctcatt    480
catggcaaga atggtctttt atttacatat ggcgtgacgg gaagtggaaa aacctacaca    540
atgacagggt ctccagggtc tggaggcctg cttcctcgtt gtttgaatat gatctttaac    600
agcatagggt catttcaagc aaaacgttat gtgtttaagt ctaatgatag gaacagtatg    660
gaaatacagt gtgaagtcga tgccttgtta gaacggcaga aaagagaagc cttgcccatt    720
ccaaagaccc cctctagcaa gcgacaagca gatccagagt ttgcagatat gataaatgta    780
caagaattct gcaaagcaga agaagttgat gaagacagtg tctatggagt atttgtctct    840
tacattgaaa tctataataa ttacatatat gatctattgg aagaagtgca gtttgatccc    900
ataaagccca aactcccaca atctaaaacg ctccgagaag ataagaacca caatatgtat    960
```

```
gtggcaggat gtacagaagt agaagtgaaa tctacggagg aggcttttga ggttttctgg   1020
agagggcaga aaaagagacg cattgctaac acccatttga atagagagtc cagtcgttca   1080
catagcgtgt tcagcattaa acttgtccag gctcccctgg atgctgatgg agacaatgtc   1140
ttacaggaaa aagagcaaat tactataagc cagctgtctc tggtagatct tgctgggagc   1200
gaaagaacca accgtactaa agcagaaggg aacagactac gtgaggccgg aaacattaat   1260
cagtcattga tgacactaag aacatgcatg gaggtcctga gagagaacca gacgtatggc   1320
actaacaaga tggttccata tcgagattca aagctaaccc atctattcaa gaactacttc   1380
gatggggagg ggaaagttcg gatgatcgtg tgtgtgaatc caaaggctga agactatgaa   1440
gaaagcttgc aagtcatgag atttgctgaa gtaacccaag aagtggaagt ggcaagacca   1500
gtggacaagg tgatatgtgg cctgacaccc gggaggcggt acaggaacct gcctcgggga   1560
ggccccgttg gagatgaacc tttggtgcct gaagtgattc tacagagctt cccaccgctg   1620
cccccatgca agcttttgga tatcaatgat gaggagaccc ttccaaagct ggctgacact   1680
ttggagaaac gacatcacct gcgacaacta atgaccgagg accttaacaa aaaatgtcta   1740
gctttcaagg ccttattaaa agaatttgac aattctctat caaataaaga aaactacgtt   1800
caggaaaaac taaatgaaag agaaaaagtg atctcgggac agaaattgga aatagagcga   1860
ctggagaaga aaaacaaaac tttggagtac aagattgaga ttctggagaa aacaactacg   1920
atctatgagg aagataagcg caatctgcag caggagcttg agagccagaa tcagaagctt   1980
cagcggcagt tttctgacaa gcgcagatta gaagccaggt tgcaaggcat ggtaacagaa   2040
acgtcgatga agtggcagaa ggaatgtgag cgtcgggtgg cagccaccca gctagagatg   2100
cagaataaac tctgggtcaa agatgaaaag ctcaaacagc tgaaggccat tgtgactgaa   2160
cccaaacctg agaagccaga gagaccctcc cgggagcggg accgggagaa aatcattccg   2220
agatctgtct ctccttcgcc tctacctctt tctagtaaca atattgctca gatttccaac   2280
ggccagcaac tcatgagcca gccgcagcta cacagacgct ctaactcttg cagcagcatt   2340
tctgtagctt cctgtatctc ggaatgggag cagaaactat ctccattcag cacacctgtc   2400
aatgtcacct cccttgcaag gcataggcag caggagccag gacaaagtaa aacgtgtatc   2460
gtgtcagaca gaaggcgagg catgtgctgg actgaaggca gggagatggt ccccacattc   2520
agcagtgaga taggcgtaga agaggaccat tgccgcagga acaccccaat tcctgtacga   2580
cacagaaggt cccgctctgc agggagcaga tgggtagatc ataagcctgc ctctaatgtg   2640
caaactgaga cagtgatgca gccgcatgtc cctcacgcca tcacagtgtc tgttgcaaat   2700
gaaaaggcgc tagctaagtg tgagaagtac atgctgaccc accaggaact agcctccgat   2760
ggggagattc agactaaagt cattaagggt gatgtttata agacgagagg tggcggacaa   2820
tcggttcagt ttactgatat tgagacttta aaacaagaat tgccaactgg tagtcggaaa   2880
cgaagatcgt ccaccctagc acctgcccaa ccagatggta cagagtctga atggaccgat   2940
gtagaaacaa ggtgctctgt tgccgttgaa atgagagcag gatctcagct gggaccggga   3000
tatcagcacc acgcacaacc caagcgcaag aaaccttgaa ctgacagccc cggcaccaga   3060
agaccgtttt tactcgtgtt ggtgatttat ccaaagctgt tccagacgca gtgtctgagt   3120
catcttgcag aagaatgtat ccagatcacg ttgccctttt ttattgtgac tttttcaact   3180
gctctgaata ttttctaagg ttttataaaa aaaaaaaaaa aacaaacaaa tgctgctatt   3240
gattagctgc aaaaaaaaat gcactttaga catatttaac aattaagact ttcataataa   3300
```

```
agatggcgac tggccagtgg tgaaaccatt ttaggaaggt atttagagtt ttgtatgtat   3360

atattcactt tctgaccttt atatatgcca aaacaactga aataaaaagg cactaagaga   3420

tgcaaaaaaa aaaaaaaaa                                                3439


<210> SEQ ID NO 17
<211> LENGTH: 2316
<212> TYPE: DNA
<213> ORGANISM: Homo sapiens

<400> SEQUENCE: 17

ggaacggctg ttagtgttta gctgtggata gccagaggtt agggtgtctt ctcgaatcgg     60

ggaacctctg attttggagg agccatggcg ctcagggtca ctaggaacac gaaaattaac    120

gcagaaaata aggccaaggt cagtatggca ggcgccaagc gtgtgcctgt gacagttact    180

gctgcttcca agcccgggct gagaccgaga actgctcttg gagacattgg taataaagtc    240

agcgaagagc tacaggcaag agtgcctctg aaaagggaag caaaaacgct aggtactgga    300

aaaggtactg ttaaagccct accaaaacct gtagagaagg tgcctgtgtg tgaaccagag    360

gtggaacttg ctgagcctga gcctgaacct gaacttgaac atgttagaga agagaagctt    420

tctcctgaac ctattttggt tgataatccc tctccaagcc cgatggaaac atctggatgt    480

gcgcctgcag aagagtatct gtgtcaggct ttctctgatg taatccttgc agtgagtgac    540

gtagacgcag atgatggggc tgacccaaac ctctgtagtg aatatgtgaa agatatctat    600

gcttatctcc gacaactgga ggaagagcag tcagttagac caaaatacct acagggtcgt    660

gaagtgactg gaaacatgag agctatcctc attgactggc taatacaggt tcagatgaaa    720

tttaggctgc ttcaggagac catgtacatg actgtgtcca ttattgatcg gttcatgcag    780

aacagttgtg tgcccaagaa gatgctacag ctggtcggtg taacggccat gtttattgca    840

agcaaatatg aggagatgta ccctccagaa ataggtgact tcgcctttgt gactaacaac    900

acgtacacta agcaccagat cagacagatg gagatgaaga ttctcagagt tctgaacttc    960

agcctgggtc gccctctgcc tctgcacttc ctccgtagag catctaaagt cggagaggtt   1020

gacgtcgagc agcacacttt ggccaaatac ctcatggagc tctccatgct ggactacgac   1080

atggtgcatt ttgctccttc tcaaattgca gctggggctt tctgcttagc gctgaaaatt   1140

cttgacaacg gtgaatggac accaactctg cagcactacc tatcctacag tgaagactcc   1200

ctgcttcctg ttatgcagca cctggctaag aatgtagtca tggtgaactg tggcctcaca   1260

aagcacatga ctgtcaagaa caagtatgca gcatctaagc atgctaagat cagcacgctg   1320

gcacagctga actgtacact agttcagaat ttgtctaagg ccgtgacaaa ggcataactc   1380

caatagactg ctacatctgc agatgcagtt ggcaccatgt gccgcctgta cataggatac   1440

ctaccgtgtt tacttgctct tcaataaagg ttgtgacttc tcattttaca tagcttaact   1500

catttgaatg ttgttgcttc tgagtttagg ctaacggaag ttgtcgaatt taggagtata   1560

ttaaaaactg catctagttt taacagtgga tccaactaat gtatatatct gtagcctata   1620

tgtctatata catccttcac tgtgtgtcct tatatcatca tgtcttctgc ctcactctag   1680

tttaaactct aaatctacca gctagtcctt tgttccattt tccagtggtt gccaccttta   1740

accactgtct cttggtttgt caactttcag atctgaaacc aagtatcttt ttttatgtaa   1800

ttatttattt gttcttaatt ggaaaatagg atgttcaaaa ttaaaggtgt gttttaaaaa   1860

gaatttgccc ccaagtctca ctatcaacag ataagggtgt attcttgtat atcctgtata   1920

gatataatca tgcatatact cccaaggaga tatttttata tgggttcatt ttatcaacag   1980
```

```
tattcctatc agcattcctt tcaatgccta tattgcattt cctagtgtga acaaactgtg   2040
tgtaacatag tcattccctc ggtgggattc aagtgcattc tctcagtgcc ctccacagtg   2100
ttcttaaatg atgtttaatg tcttgcttgg cttcattcat agtagctctt ccaggggtgt   2160
gctttgaatt ctgacagcca gatgggtgtg gctgccacca taccaaggcg ccactcctgt   2220
cttgtaatgc cacctggaaa agaatcctgt ctcatttgct gttttaattt atacatctga   2280
tatcaagttg aataaaattt attggtggaa agcttt                             2316
```

<210> SEQ ID NO 18
<211> LENGTH: 3049
<212> TYPE: DNA
<213> ORGANISM: Homo sapiens

<400> SEQUENCE: 18

```
attccgcggg gtccaacggc tcgagagtgg agacggactc cgggtgaagt ctgctgcggc     60
tggttaccgt tctccgtccc gcgcgtggca agtggagggt ctcgattctg gacagcttgg    120
agcgtccacc atgaggagaa gtgaggtgct agcagatgag tctatcacat gcctgcagaa    180
agctctaact cacctccggg aaatatggga actaattggg attccagagg agcagaggct    240
acaaagaacc gaggttgtaa agaagcatat aaaggatctt ctggatagaa tgattgctga    300
agaggagagc ctgagggaaa ggctgctcaa aagcatatcc atctgtcaga aggagctgag    360
taccctgtgc agtgagctac aagtgaagcc atttcaggaa gaaaaagata caaccatctt    420
gcaactagaa aaagatttgc gcactcaagt agaattgatg agaaaacaga aaaaggagag    480
aaagcaggaa ctgaagctac ttcaggaaca ggagcaagaa ctccgtgaca tcctctgtat    540
gccgccctgt gatgtggaca gcacctctgt ccccacctta gaagagctga agctattccg    600
acagcgtgtg gcaacgctga gggagacaaa ggaatcgagg cgtgaagaat ttgtcaacat    660
taagaaacaa atcatattgt gtatggaaga attagaacac tctccagata caagctttga    720
aagagatgtg gtgtgtgaag atgaaagtgc tttttgttta tcactggaga acattgcaac    780
attacagaag ttgctgaagc agctggaaat gaaaaaatca caaaatgaag cagaatgtga    840
ggggctccgc actcaaatcc gagagctctg ggataggtta caaatacctg aagaagagag    900
agagcctgtg gaggcaatta tgactggatc aaaaaccaaa atcaggaatg cgctgaaatt    960
agaagtggat cggttagaag aactgaaaat gcaaaacata aagcaagtga ttgagaaaat   1020
ccgagtggag ctggctcaat tctgggacca gtgtttttat agccaggaac agaggcaggc   1080
ttttgcccct tactattctg aggactacac agaaaacctg ctccatcttc atgatgccga   1140
gattgtacgg ttaagaaact actatgacgt tcacaaggag ctgttccaag gcgtccagaa   1200
gtgggaagag agctggaaac ttttcctaga gtttgagaga aaagcttcag atccaggtcg   1260
atttacaaac cgagggggaa atcttttaaa agaagaaaag gaacgagcaa agctccagaa   1320
aacactccct aagctggaag aggagttgaa agcacggatt gaacagtggg aacaggagca   1380
ctcaacagca tttgtggtga atgggcagaa attcatggag tatgttacag aacagtggga   1440
attacatcgg ctggagaaag agcgagccaa acaggagagg caactgaaga acaagaaaca   1500
gacagaggca gagatgctgt atggcagtac tccccggaca cctagcaaaa gaccaggaca   1560
gacgcccaag aagtctggca aagtacgcaa gatgaacact accaccatgt ctagtgctac   1620
acccaacagt agcattcggc ctgtctttgg tggatcagtg taccggtcac ctatgtctcg   1680
actaccccct tctggcagca agtcagttgt cacttctctg tgttctggaa agaaaacacc   1740
```

```
tcgagctgcc cagcttaggg ccaacaagga gaacttggac ctcaatggca gcatcctgag   1800
cggtgggtac cctggctcga cgcccctcca gcacaactgc agcattaagt ctgttgccag   1860
cacctattct gagttttcgc gagaactttc aaaggcttcc agatctgatg ctacgtctcg   1920
aatcctcaat tcaaccaaca tccagtcctg agagtccttg tccagttagg cagctggggc   1980
ttcctgtgcc tggactggac tgacggatac gtagacaagg agtgacatat acatttccat   2040
cagtttagat gtttgaaact accttgggca ggttctatta actgcaccta actcagacgt   2100
gagtaggaca gaaggaagct gtcccgggcg aactgaggtc acaaagactt gcttttgatt   2160
caagagagac cttaaaggct agttatgata gttaagtaca agttttaaca tctggtagct   2220
aacttttttt ctctaccccg taattctact atgactgctc ttctagaggt cctgagttca   2280
aatcccagca accacatggt ggctcacaac catctataat gggatctgat gccctcttct   2340
ggtgtgcaga aataattttt tttttaattc tacttatttc aatactatat attagaaaat   2400
gaaaaaacga ttgtggcctg ctttggcata caggggtaca agacatgaag taattctggt   2460
aacatctaaa aatatatata tttttgttcg cggacatttg attaatgctg tagctatgga   2520
agctttgatg tcacccagag gcgtgtacct ggctggcact atcccagtga gggtttcttg   2580
agttccagta tgagatggcc tgacctgctg ccaaaaagag tagcagtcat ttctgtagtg   2640
caatttcttg aggtatatgt gtgaacacac atgcttgtct gacctgttga gtttttctcc   2700
agtctcccaa ccctgtgctc attaggccca gtctgttccc tgtagatgac aaccacatag   2760
agaggctgtc tggtgggctg ggccattcct gtcatggagt cagcaacttt gcacatctac   2820
aagttatctg tgtaatcacg tccacaatga ggctctccaa acccatcact actcttcccc   2880
aaagcactat atttattctg tctgtctgtg ccagttctgc ccacactgac tgatcttgaa   2940
aacctgtcag tctgctcttc acacacatat atgttgtttt taaatgtatg aaaataaaat   3000
gtgtatagtt accttttaaa tactaaaaaa aaaaaaaaaa aaaaaaaaa              3049
```

<210> SEQ ID NO 19
<211> LENGTH: 694
<212> TYPE: DNA
<213> ORGANISM: Homo sapiens

<400> SEQUENCE: 19

```
ctgcgcggag cgtgattggt tggtggcttc gcccaatcgg cggagggctg tcggattcaa     60
atccagagcg ttgggcctgc ggtcgttggc ctcattcgag tcgttgcgtc ggccctaggc    120
ggacgtagag ccccttgcgc ccggtttcct gatcccgctt actcctctgc gcgccggcag    180
gatggcccac aagcagatct actactcaga caagtacttc gatgagcact acgagtaccg    240
gcatgtcatg ttacccagag aactctctaa acaagtaccc aaaactcatc tgatgtccga    300
agaggagtgg aggagacttg gtgtccaaca gagtctagga tgggttcatt acatgattca    360
tgagccagaa ccgcatattc ttctctttag acgacctctt ccaaaagaac aacaaaaatg    420
aagtgcagct gggatcatct aatctttttc aaatttaatg tatatgtgta tataaggtag    480
tattcagtga atacttgaaa agtgtacaaa cctttcatcc atacctgtgc atgcgctgta    540
ttcttcacag caacagagct cagtcaaatg caactgcaag tagggttgtt ttaagttgtt    600
caagatagtt tcttgtagtt ttttcttaat ataaatgcct gttttatttt acctgttttg    660
ttaaataaag tttgtatatt gcatttatat cacc                                694
```

<210> SEQ ID NO 20
<211> LENGTH: 1100

<212> TYPE: DNA
<213> ORGANISM: Homo sapiens

<400> SEQUENCE: 20
aaagcgagga gctggttgct ggtgttgtgc gactctgaac aatagaagtg ccgcggcctg 60
ggaactagcg accgtttggg gtgacttggc agttgacggg accacgggac ccgggcgcgt 120
ccgtcatgtt ctgcgaaaaa gctatggagc ttgtccgcga gttacaccgc gcgccggaag 180
ggcagctgcc ggcctttaat gaggacggac tcagacaagt tctggaggag atgaaagctt 240
tgtatgaaca aaaccagtct gatgtgaatg aagccaagtc agctggacga ggggatctga 300
taccaaccgt caaatttcgg cactgtgctt tgttaagaaa tagacgctgc acgatagcat 360
acctgtatga ccggttgctt cggattagag cactcaggtg ggaatatggg agtgtcttgc 420
caaatagttt acgattccac atgtctgctg aagaaacgga gtggttcaac cattataaaa 480
agtctcttgc tacttacatg aggtcgctgg gaggagatga aggcttggac atcacacaag 540
atgtgaagcc ccccaaaagc ctatatattg aagtgcggtg tttaaaagac tatggagaat 600
ttgaagttga tgatggcact tcagtcctgc ttaaaaagaa tagtcagcac tttttgcctc 660
ggtggaagtg tgagcagtta atcagacaag gagttctaga gcacgtgctg tcctgactgt 720
gtcctgtggt gacagcagct ggatgtgaag ctaagccaac tcacagaagg aaacgtcctc 780
actggacctc cccctccttg gttttaaatt gacagacatg cattaacata accaagatgg 840
gctggggtcc agctcattgg tagagcacct gcttaggatt tgagaaaccc agagtttcat 900
ccctagtacc tcaagaaaca agacaacaaa aatcaaagac aaaaccaaga actcttggct 960
aggagcataa gctgccagct cttaagcctt tgttacaggt tatatctcta gttattccat 1020
tcccacagta atattgtact cttataattg aaaataaaca gtctttggtt tgaatctgtt 1080
ttcacaaaaa aaaaaaaaaa 1100

<210> SEQ ID NO 21
<211> LENGTH: 467
<212> TYPE: DNA
<213> ORGANISM: Homo sapiens

<400> SEQUENCE: 21
attcttgtta tttgagtgct ctttcactct cctccgccat gcccgacccg gctaaatctg 60
ctcctgcccc caaaaagggc tccaagaaag ccgtaaccaa ggcccagaaa aaggacggca 120
agaagcgcaa gcgcagccgc aaagagagtt actctatcta cgtgtacaag gtgctgaagc 180
aagtccaccc cgacaccggc atctcatcga aggccatggg catcatgaac tccttcgtca 240
atgacatctt tgagcgcatc gctggcgagg cttcccgcct ggcgcattac aacaagcgct 300
cgaccatcac ctccagggag atccagacgg ccgtgcgcct gctgctgccc ggggagctgg 360
ccaagcacgc cgtgtccgag ggcacaaagg ccgtcaccaa gtacaccagc tccaagtgag 420
ctctcgcagc tgccagcaat ccaaaggctc ttttcagagc cactcac 467

<210> SEQ ID NO 22
<211> LENGTH: 4095
<212> TYPE: DNA
<213> ORGANISM: Homo sapiens

<400> SEQUENCE: 22
gagcgactgg attttttga atcggaggcg gcagcctctc tcgagccatg gcggcgcctg 60 tgaggggggag acttagtgtt tgagaaggat aagcgaggac tgcgccgtcg tggttccttt 120

```
ttaaaatctc tgagcgtgcc ttcatcaagt agtgcaaaca atggctgacg acagcgtgtt    180
accatctcct tctgagataa ctagcttggc agactcttca gtgtttgatt ctaaagttgc    240
tgaaatgtcc aaggaaaact tgtgcttggc gtctacttca aatgttgatg aagaaatgcc    300
gcaggttgaa gcaagagtga taatggtcca ggatgctggg aaacaagaag aacttctaaa    360
ggccttaaag actattaaga taatggaagt ccctgttata aagataaaag aaagttgtcc    420
tggaaaatcg gaggaaaaat taataaaaag tattattaat atggaaatga aagtgccctg    480
tgtaaagatg gactcaatgg aagaatttga aagtttggat tccccagaat ttgagaatat    540
atttgtagtt actgacttcc agaattctgt cttcaatgac ttatacaagg ctgattgtag    600
gattgttggg ccaccagtta tactcaactg tgcacaaagg ggagagccct tgccgttttc    660
ctgccggccg ctgtattgta cgagtatgct gaacctggtg ctctgcttca ctggattcag    720
gaagaaggag gagcttgtca aattggtgac gttggttcat catatgggtg gagttattcg    780
aaaagagtgt aattccaaag taacacatct ggtggcaaat tgtacacaag gcgaaaaatt    840
tagggttgct gtgagcctgg gcactccaat tatgaagcca gaatggattt ataaagcgtg    900
ggaaagacgc aatgaacagt gtttctgtgc agcagttgat gactttagaa atgaatttaa    960
agttcctcca ttccaagatt gcattttaag tttcctggga ttttcagatg aagagaaaca   1020
tagtatggaa gaaatgactg aaatgcaagg aggtagctat ttaccagttg gggatgaaag   1080
gtgcactcac cttattgttg aagagaatac agtaaaggac cttccattcg aaccttcaaa   1140
gaaacttttt gttgtcaagc aagagtggtt ctggggaagc attcagatgg acgctcgtgc   1200
aggagagact atgtatttgt atgaaaaggc taatactcct gagctcaaga aatcggtgtc   1260
tctgctttct ctaagtactc caaacagcaa ccgcaagaga cggagattga aagagaccct   1320
ggctcagctc tccagggaga ctgacctctc tcctttccct ccccggaagc ggccctcagc   1380
tgagcactct ctttctattg gctcactcct ggatatctcc aacacacccg agtccagcat   1440
ccactatgga gaaacaccga agtcctgtgc taagtcttct agaagttcta ctccagttcc   1500
tccaaagcag tcagccaggt ggcaggtggc gaaagagctc taccagactg agagcaatta   1560
tgtcaatata ctggccacaa tcattcaatt atttcaggtg cccttagaag aagaaggaca   1620
gcgtggtggg cctattcttg cacctgagga gatcaagact atttttggga gcatcccaga   1680
tatctttgat gtgcatatga agatcaagga tgatcttgaa gaccttattg ctaactggga   1740
tgagagcaga agtattggtg acatctttct taaatatgca aaagatttgg taaaaaccta   1800
ccctccgttt gtaaacttct ttgaaatgag caaggaaatg atcattaaat gtgagaaaca   1860
aaagcccaga tttcatgctt tcctcaagat aaatcaagct aaaccagaat gtggacgaca   1920
gagccttgtg gaacttctca tccggccagt gcagaggcta cccagtgtcg ctttactttt   1980
aaacgatctt aaaaagcata cagctgatga aaatccagac aaaagcactt tagaaaaagc   2040
tattggatca ctaaaagaag taatgacaca tatcaatgag gataagagaa aaacagaagc   2100
acagaagcaa atttttgatg ttgtttatga agtagatgga tgcccagcta atctcttatc   2160
ttctcatcgg agcctggtgc aacgagtgga aacggtttcc cttggtgagc acccttgcga   2220
ccgaggagaa caagtcactc tcttcctctt caatgactgc ctcgagatag caagaaagcg   2280
gcacaaggtt attggcactt ttagaagtcc tcacgaccgc acccggcccc ccgcttctct   2340
gaagcacatt catctcatgc ctctttctca gattaagaag gtgctggaca tccgagagac   2400
agaagattgt cacaatgcct ttgccttgct tgtaaggcca ccaacagaac aggccaatgt   2460
actgctcagc ttccagatga cgtcagagga gcttccaaag gagagctggc tgaagatgct   2520
```

```
gtgccgacat gtagccaaca ccatttgtaa ggcagatgct gagaatctta tgtatgtggc   2580

tgatccagaa tcctttgaag taaatacaaa agatatggat agtacattga gtcgagcatc   2640

tagagcaata aagaagactt caaaaaaggt tacaagggca ttctcttttt ccaaaactcc   2700

caagagagcc ctgcggatgg ctctttcatc atcccatagc tcagagggaa ggagtcctcc   2760

gagcagtggc aagcttgctg tgagccgtct gtccagcaca tcatccttag caggtattcc   2820

atctccctcc cttgtcagcc tcccttcttt ctttgaacgg agaagtcata cattaagtcg   2880

atctacaact cacttgatat gaaacttaag tcctgtggga cctatgcttc aacaagacgc   2940

tgacttaagt ggtactttga attagcactt ggtaaagttg tagagaagat tagtaacact   3000

aaccaacgcc gttttatttt cttgaaatac aattttcaag atggtctatg taaaaaaaat   3060

atggattttg atgtaattta tctttatttg aatctcacat ctgaagacca gtgacttaag   3120

ttattcctga taatcagtag ctttgtaacc ctgatacagt aaacagttgg tgggtgcaaa   3180

atactattgt gtatttgtat agtatcttga atttttggaa gtacatattt gtgtatctca   3240

atttgtgcaa agactgaaca gcaatgcaac acttgctgaa taaaaccctc tgattaaatt   3300

ctagaggctt gttcagttcg attgtttgat gtacttaact gcgcttttgc agtttatttt   3360

cttttaaaat aagagatcta acacatgaat tttaaaggat acaccattat taaccataca   3420

attacgatcg tttggaattt tcttttgcaa attgagataa gaagagaaag attacaaaac   3480

attgtatatg ttgcgaagat aagatattag tatgtacttt ataattgttt cagagacttt   3540

tatttttatt ttattttctt attctagaca ctagcaaatc ttgatttagt tttgactact   3600

gtattgaatt tatttcaaag gataagacca cgtgaaaact gtgttaagaa ttgcttctgt   3660

tctttgtaca gttctgaagt tgtcttcagt tttgctaatc gcctgtgaaa agcatagata   3720

taatgtgtgg tgaacttttt attgtggtca tatcattaaa ataagattgg aaatttattg   3780

tcaaaaattt tgtgaatctg ccattatctt ctactgcaat atttctttta gtcagtaata   3840

cagaatgact gggctactat ggccaagaat attttatttc ttacacgttc agaggagtgt   3900

tacaggtctc cttgttacat aattttcaat aatctgcttt aatagtttaa ctgactggat   3960

tttttctat accatgtatg taccaattca cacgttagta aatgaccttg ttttgctata   4020

ttttaaaagc agttatatta gcaagaactt tgtaaataaa tagctttaaa atacaagtaa   4080

aaaaaaaaaa aaaaa                                                    4095
```

<210> SEQ ID NO 23
<211> LENGTH: 5683
<212> TYPE: DNA
<213> ORGANISM: Homo sapiens

<400> SEQUENCE: 23

```
agtttgtggc gccagaattc agagcgcgtg agcgcctgag cagcctcctc cggagccagg     60

ttctccactt cccccgcctc gggttccggc ttctgcaagc ggggcaccat ggtggtcctc    120

cgcagcagcc tggagctgca cagtcgctcc accacctcct cggccaccga ctctctggac    180

ctgtccagtg agttcctcag cctgcaggac agcggcggga ggcggcccag attgcgccga    240

gccgggagga aatcgacggc gtccaaggcg gcgggcgatg gattcacagt taagggagct    300

gaaacctacc acaacacgcg ctctttaagg tctctgagaa accaagcaca aacttcttca    360

gagtctagtt ttgacaagaa cgtggacaga acagagaaat actccaatgg cagacatttc    420

acaaggcaat ttgctcgaca gcaggctgat aaaaaagaag agtgcaaaga agacaaagtt    480
```

```
attccagtta ttcgctcatt gaggaataga aacattgctc caactgcaga acatttgcac    540
gaacaaagtg gagatgttga agttcgaaga agttgcagga ttagaagtcg ttacagtacc    600
atgaaccagt ctgtgctatt tgacaagctt ataacaaaca ctgctgaagc tgtacttcaa    660
aagatggatg acatgaaaaa gatgcgcaga cagcggatga agaagcttga agacttggga    720
gtattcaatg aaacagaaga gagtaatctc actatgtaca caagaggaaa actaaaggct    780
atccagcgag ctgatgaaga aacaactgat aaccaggacg gcagtgtgga atcatctgaa    840
gagggggaag agcaagagga tgatgatggc gaagatgaag atgatgaaga tgaagaagag    900
ggagaagaag ataatcaaaa aagatactat cttaggcaga gaaaaacaac ggtttactac    960
cagtctccac tggaaagtaa acctcgtcac cagagaaagc ccaacatgtt ttatagtggc   1020
ccagcttctc ctgcaagacc aagattccgc ttgtcttcta cgggaccaag aagtccctat   1080
tgtaaacgaa tgagcaggcg aaggcatgcc atccacagca gtgactctac ttcctcctcc   1140
tcctctgaag acgactgttt tgagaggaga acaaaaagga accgaaatag agctattaac   1200
aggtgcctcc cactaaattt tcggaaagat gaaataagag ggatttataa agatcgaatg   1260
aaaattggag caagccttgc tgatgttgac ccaatgcaac tagatacttc agtgcgcttt   1320
gacagtgttg gcggcctgtc cagtcacatt gcagctctaa aagagatggt ggtgtttccc   1380
ttactttatc cagaagtctt cgaaaagttt aaaattcaac ccccaagagg ttgtttgttt   1440
tatggaccac ctggaactgg aaaaaccctg gttgctagag cacttgccaa tgagtgcagc   1500
cgaggggata agagagtggc gttcttcatg aggaaaggtg ctgactgcct gagtaaatgg   1560
gtaggagaat ctgagagaca gcttcggttg ctatttgacc aggcctatca gatgcgccca   1620
gcaattatat tctttgatga aattgatggt ttggctccag tacgatctag caggcaagat   1680
cagattcaca gttctattgt ttcaaccctg ttagctctta tggatggttt ggacagcaga   1740
ggagaaattg tggtcattgg agctaccaac cggctagatt ccatagaccc tgctttacgg   1800
aggcccggtc ggtttgacag agaattcctt tttagtctac ctgataaaaa tgctcgaaaa   1860
gagattctga agattcatac aagagattgg aatccaaagc cagtggacat gtttctagaa   1920
gaactagcag aacactgtgt tggctactgt ggtgcggata ttaagtcaat ctgtgctgaa   1980
gctgctttgt gcgccctgcg tcgacggtac ccgcagatct acaccaccag cgagaagctt   2040
cagctggatc tctcttcaat taccatctca gctaaggatt ttgaggcagc tctgcagaaa   2100
ataagaccag cttcccagag agctgtgaca tcacccggac aggcactgtc tgccattgtg   2160
aaaccacttc tgcaaaatac tgttcatagg atcttagacg ccctacagaa agtatttcca   2220
catgtggaag ttggaacaaa caaatcttta aattcagatg tttcttgccc ttttctagaa   2280
agtgatttgg catacagtga tgatgataca ccatctgtgt atgaaaatgg actttctcaa   2340
aaagaaaatt taaattttct tcatttaaat agaaatgcct gttaccagcc tatgtctttt   2400
cgaccaagac tattgatagt gggagaacca ggatttggac agagttctca cttggcacca   2460
gctgtcatcc atgctttgga aaaatttact gtatatacat tagacattcc tgttcttttt   2520
ggcatcagta caacatctcc tgaagaggca tgttcccaaa tgattcgtga agctaagaga   2580
acagcaccca gcatagtcta tgtcccacat atccatttgt ggtgggaaat agttggaccg   2640
acactcaaag ccacatttac aacattatta cagactatac cttcatttgc tccagtttta   2700
ttacttgcaa cttctgagaa accatactca gctttgccgg aagaggtaca agaattgttt   2760
acccatgatt atggagaaat ttttaatgta cagttaccag ataaagaaga acgaaccaaa   2820
tttttttgaag acttaatttt aaaacaagct tcaaagcctc ctgtgtcaca aaagaaagca   2880
```

```
gttctgcagg ccttggaggt gctcccagtc gcaccaccgc ctgaaccaag accactgaca   2940
gcagaggaag ttaaacggct tgaagaacaa gaagaagata cattcagaga actcaggatt   3000
ttcttaagaa atgtcacaca tagacttgct attgataagc gattccgagt ctttactaag   3060
cctgttgacc ctgatgaggt tcctgattat gtcactgtca taaagcaacc aatggacctt   3120
tcatctgtaa tcagtaaaat tgatttacat aaatatctca ctgtgaaaga ctatttgaag   3180
gatattgatc taatctgtag taatgcttta gaatacaatc cagatagaga tcctggagat   3240
cgtcttatta ggcatagagc ttgtgctttg agagacactg cttatgcaat aattaaagag   3300
gagcttgatg aagactttga gcagctctgt gaagaaattc aggaatctcg gaagaagaga   3360
ggttgtagct cctccaaata cgcaccatct tattaccacg tcatgccaaa gcaaaattct   3420
cctcctgttg gtgataaaaa gccagatcaa gagcagaatg agaagctaaa ggtaccgtgc   3480
actcctgtgg cgtgcagcac acctgctcag ttgaaaagaa aattccataa aaagtcaaag   3540
tggcatgtag gcaccaaaat aaagcgaagg aaaatttcac aagctaaaga caacagcttg   3600
aatgctatga acagttcaag caggagcgac acagaagaca gccagcacac acatgcagag   3660
cacacggagc ctggaaacac ggacgagtcc tcggtagaag aaagtgacaa gcaaaataga   3720
cttgaaagca acatagactt gaaaaataac tcaagttcct ctaatattga gaatgaactt   3780
gaagagccta aggaaactac ggagggcaca gaactgagaa aagacaggat tgtttgcagg   3840
ggtgatgcct ctgcctccca ggtcacagac attcccgaag acagtgaatc aaaagaaatg   3900
gattttctgc ggatgactct agctagaggt tcccaggtag agcagcagga gctcatcagt   3960
atggagcagg ctctggccat cctctctcag ccgacaccct cacttgtgct ggaccacaag   4020
cagttaacaa atattttgaa gacggttgtt aaaaaaagtc agaaatataa tatattccaa   4080
ctggagaatt tgtatgcagt aatcagccag tgtatttatg agcaccgcag ggactatgac   4140
aaaacagcgc ttgttcagaa aatggagcaa gcagtagaaa acttcaattg ttccagatca   4200
tagtcgatac attcaagtac tttatcttca gttcctattt aattgtcttc agatatatca   4260
tcataactga tgcaagataa ggtgaaatct tgcatcttca agaaaagatt aaaatagtaa   4320
aagtatctta aatttcctga tatttatgta catatagtaa gataactgat aagtcttaga   4380
tgtttgagtg aagcactgct acaatagtaa tagtttggct agatcttaaa gctgttttgg   4440
taattaatgt cttgtgacat ttaataatga cttagcaagc attggatttt ttttttttgt   4500
tgttcttgtt agctaaagca cttttagttt tatccttccc tagtaggtta ttgtatcaga   4560
ctagaattat atctgttata ttttgctgtc tttgttttcc tttgtctttc tcctgtttgc   4620
caaaattcaa ttcaagttgt gattttcaag aggacctcaa aacaattctg tacttaatat   4680
aaaaatcaat gtctttagat aaatactttc atagttctaa tttgggttaa tatttttaaa   4740
tgtattgttt acttttgtaa ttatatacac aacaaatatt agtgactagt ttttgtattt   4800
gacaactgtt taccattgtg tttaggttat attctataaa tactctttat atgcatatat   4860
atggctataa atataaattt tgtattactg gtaccaaaaa cacttttttt ttttttttcca   4920
gcagggtttc tctgtgtagc cctggctgtc ctggaactca ctttgtagac caggctggcc   4980
tcgaactcag aaatctgcct gcctctgcct cccaagtgct gggattaaag gcgtgggcca   5040
ccacgcccgg ctcaaaaata catttcttaa agttgaaatc atttgcttct tccataatgg   5100
gacgttgaaa cttctgcttt cggaacagcg tgtgttggaa agcttgtttg agaatggcta   5160
ctagagttta agaggctatg tatggagttt gttggggatg tagtgatggt ggtaaggatc   5220
```

```
agacctaggg cccagtgtac acttaagcac atgcctaact caagagttta gattttagta   5280

tagtttaaag ttgagctgcc ttttcttatg tagctattta aaatatttct gaagttcagt   5340

aatttggatg ccttcattag tagatgctgt cctatatacc tattaaaaat gccaaacact   5400

gataacattg aacatgttca tattgataga gataatattg tataggtcta gtgtgtatgg   5460

atctgggatc tccgcccttg aggcagagac gggaagatca ggagttcaag gtcttagcta   5520

catagtaagt ttgaagccag cctggctact tgagactctg tctcacaaaa gcaaataaac   5580

aaaggattat gcttaatagt tttcattgaa gtttattata acttatttca gatgtgtcct   5640

tttattgtac attttgtata ataaatgttg aagttgaaaa ctg                     5683
```

<210> SEQ ID NO 24
<211> LENGTH: 1362
<212> TYPE: DNA
<213> ORGANISM: Homo sapiens

<400> SEQUENCE: 24

```
gtgcttgacg ctgctggcgt ggataagtgg acatggcgag ctccgactgt gagggccatg     60

cgggccagga gggggagaca ttcctgtact tcgcctacgg cagcaatctc ctgaccgaga    120

ggatccacct gcgaaacccc tcggccgtgt tctgctgcgt ggcgcgcctg caggacttta    180

agctcgactt cggcaatttc caaggcaaaa tgagtgagag gtggcacgga ggtatagcta    240

ccatttttca aagtcctggc gacgaagtgt ggggagtggt atggagaatg aacaaaagca    300

atataagttc cctggatgag caagaaggag ttaaaagtgg agtctatgtt gtaatagaaa    360

ttaaagtttc aactcgagaa gggaaggaaa taacctgccg aagttacctg atgacgaact    420

acgagagcgc gcccccatca ccacagtata agaaggttat ctgcatgggt gcgaaagaaa    480

acggtttgcc acaggaatat caagagaaat taaaagcaat agaaccaaat gagtataaag    540

gaaagatctc cgacgaaatg gaagacatca tcaaaaaggg agagtcaaaa ctgtcataac    600

agactctgaa gctatgtgtg ctagtatgaa gtgcttttaa cgtttgcgaa caggagtctg    660

gaccttcttg gttctgacct tgattttcaa cagtgctggg aagggcttct cacataggtg    720

attctttatt tttaactgta acaaagaact ggaatgggga tgggcttaga ccattaaagg    780

gaccagggga tcctggcatg tgcaagtggt gatggccgtg ggttctcctg tggacactgc    840

tatagccccc cactgtgtgg acgacctccg tggagggtag gtctgtagct caggggcgca    900

ctgctgcgct tggtctgctt tctgcttgta tccgatcggc ttgtaagaag taagcaaaat    960

atagagggta ggtggtaagg ctttgagaag tacaaagatg gtacactgtc ctttgagggg   1020

cgactgcttt catgactcta aggggtttct cagcaagagc tccacctcac tgtgctctgc   1080

tcagaccaca cagagcagcc tcagctcata gagtctgtgt taactggtat tgtggactct   1140

ggagccaagc tggccttgaa cctgtgacca tcttgcctca gcttctcata tagctggctg   1200

ggattatagt cttgtgctac tggggctagc tgagcctccc actttccagt tgtgggactt   1260

gagcttctct ggctcactgg accttagttg cttcacctgt ataaataggg aaaatcaaaa   1320

acgtgaattt gaagatttca tgagtaaaca tgtgataagc tt                      1362
```

<210> SEQ ID NO 25
<211> LENGTH: 435
<212> TYPE: DNA
<213> ORGANISM: Homo sapiens

<400> SEQUENCE: 25

```
atgcctgagc cagcgaaatc cgctcccgcc ccgaagaagg gctccaagaa ggccgtgacc     60
```

```
aaggcgcaga agaaggacgg caagaagcgc aagcgcagcc gcaaggagag ctactccgta    120

tacgtgtaca aggtgctgaa acaggtccac cccgacaccg gcatctcctc taaagccatg    180

gggatcatga attcctttgt caacgacatc ttcgagcgca tcgccggcga ggcttcccgc    240

ctggcgcatt acaacaagcg ctcgaccatc acctccaggg agatccagac ggccgtgcgc    300

ctgctgcttc ccggggagct ggccaagcac gctgtgtcag agggcaccaa ggccgttacc    360

aagtacacca gctccaagta aacttgtccc tgcaactgcc ttagtaaacc caaaggctct    420

tttcagagcc actca                                                     435
```

<210> SEQ ID NO 26
<211> LENGTH: 1235
<212> TYPE: DNA
<213> ORGANISM: Homo sapiens

<400> SEQUENCE: 26

```
ggaagtgagt cacaggcagc cgtaggggag aaacagaaga tggccgccag acaggggggg     60

taaaaaaatc caaaacacca cacccagtgt cggaagttaa acactgggcg agtgctccct    120

agaatgacat ccgactcccc agaagaagcg gggaccggcg gtgtaccgct aaaagggctc    180

ccctgaatcg gaactgtccg aaaaggttcc gtgcgagcag ctgcggggaa ccacgtgagg    240

ccggggagcg tttccggtgc gggcagtcgc agccggcggt aaagccttgt catctgaagg    300

ggaccatggc caacagtgag cgcaccttca ttgccatcaa gcctgatggg gtccagcggg    360

ggctggtggg cgagatcatc aagcggttcg agcagaaggg gttccgcctt gttggtctga    420

agtttctgca ggcttcagag gaccttctca aggagcacta cactgacctg aaggaccgcc    480

ccttctttac tggcctggtg aaatacatgc actcaggacc agtggttgct atggtctggg    540

agggtctgaa tgtggtgaag acaggccgcg tgatgcttgg agagaccaac cccgcagact    600

ctaagcctgg gaccatacga ggagacttct gcatccaagt tggcaggaac atcattcatg    660

gcagcgattc tgtaaagagc gcagagaagg agatcagctt gtggtttcag cctgaggagc    720

tggtggagta caagagctgt gcgcagaact ggatctatga gtgacaggac ggtgctggtt    780

ttctacctgc ttactcttgt tctcacaggc aggggaccag caaccctaga tatttctgga    840

acttctttga cctggaagga acctttggga gctgtgactc cctgtgcagt gttacgtgcc    900

actgttagat taaagtgttt aatctgtact ttgtattgct gtacagctct gcattcctta    960

cctccttcag gcttctggat aatctgagtg gacagaatgt aaatgtttta caaattactt   1020

atattggcct catgtgcaca cagagattct tttcatttgt ggtttgagcc accaccctga   1080

gacacaaggg catttctttg tctatctccc ttcctatcac ctgtgttctg ttctctcctg   1140

gcacagtcag acaacaattt gtgtggagga tgtgtgaggt tgtgaaaact gttctgggaa   1200

cagagaattc attagaaata aagatgccaa gccaa                              1235
```

<210> SEQ ID NO 27
<211> LENGTH: 4363
<212> TYPE: DNA
<213> ORGANISM: Homo sapiens

<400> SEQUENCE: 27

```
gggggagggg gaaggaggga ggggagagcg gtggcggcgg ctgcgccggg ctgtgtgtct     60

ctcgccgccg gaggaagatg aggctgaaga tcgggttcat cttacgcagt ttgctggtgg    120

tgggaagctt cctggggctc gtggtcctct ggtcttccct gtcctcgcgg cccgacgacc    180
```

-continued

```
agagcccact gagcaggatg agggaagaca gagatgtcaa taacccccttg cctaaccgag    240
gaggcaatgg actagctcct ggagatgaca gattcaaacc tgtggtacca tggcctcatg    300
ttgaaggagt agaagtggac ttagagtcta ttagaagaaa aaacaaagcc aaaaatgaac    360
aggagcgcca tgctggagga gattcccaga gagacgtaat gcagaggcag taccttacat    420
ttaagcctca gaccttcacc taccgtgatc ctgtgctacg cccaggggtc ctcgggaact    480
ttgaacccaa agaacccgag cctcacggag tggttggtgg ccctggagag aaagccaagc    540
cattggttct gggaccagaa tacaaacaag cagttcaagc cagcattaag gagtttggat    600
ttaacatggt ggcaagtgac atgatctcac tggaccgcag cgtcaatgac ttacgccaag    660
aagaatgcaa gtattggcac tatgatgaaa acctgcttac ttcaagcgtt gtcattgtct    720
tccataatga aggatggtca accctcatga ggacagtcca cagtgtaatc aaaaggacac    780
caaggaagta cttagcagaa atcgtgttaa ttgatgactt cagcaataaa gaacacttaa    840
aagagaaact ggatgagtat ataaagctat ggaatggcct cgtgaaggta tttcgaaatg    900
agagaagaga gggtttgatt caagctcgga gcattggcgc acagaaggct aaactcggac    960
aggttttgat ataccttgat gcccactgtg aggtggcagt taactggtat gctccacttg   1020
tagcccccat atctaaggac agagctacat gtactgtgcc tctaatagat tacatagacg   1080
ggaatgatta ttccattgaa ccacagcaag gtggggatga agatggtttt gccagagggg   1140
cctgggactg gagtatgcta tggaaacgta tcccactaag ccacaaggaa aaggccaaaa   1200
gaaagcataa aactgagcct tatcggtctc cagctatggc gggtggattg tttgccatag   1260
agaaggactt cttcttcgaa ctgggtctct atgatcctgg tctccagatc tggggtggtg   1320
aaaactttga aatttcatac aagatctggc agtgcggtgg caaattgtta tttgtgcctt   1380
gttctcgtgt tgggcacatc taccgtcttg agggctggca aggaaacccc ccaccccttt   1440
acgttggctc ctctccaact ctgaagaatt atgttagagt cgtggaagtc tggtgggatg   1500
aatataaaga ctacttctat gctagccgtc ctgagtcaaa ggcgctgccc tacggggaca   1560
tatctgagct gaagaaattt cgagaagatc acaactgcaa aagtttcaag tggtttatgg   1620
aagaaatcgc ttatgacatc actgcccact accctttgcc ccccagaaat gtcgagtggg   1680
gtgaaatccg aggcctcgaa actgcatact gtattgatag catggggaag acgaatggag   1740
gcttcgtgga gctaggaccc tgccacagga tgggtgggaa ccagcttttc cgaatcaatg   1800
aagcaaacca gctcatgcag tacgaccagt gtttgacaaa ggggcctgat ggatccaaag   1860
tcatgatcac acactgtaac ctaaatgaat ttaaggaatg gcagtacttc aagagcctgc   1920
acaggtttac gcacatcact tccggaaagt gcttagatcg atcggaggtc ctgcatcaag   1980
tgttcatctc cacctgtgac tccagtaaaa tgactcagaa gtgggagatg aataacatcc   2040
acagtgtttg acaagaacag aggaaaccaa caatctacct actgacaagt acatttatgg   2100
aggactgaaa accgcctgga acctgctgca accattatta ctaattttgt acagctccaa   2160
acctggaacc tctctgatca gttggaaggg gcattgataa actgtgattt tacaataaca   2220
ttatcatctg cagtgactgt ttacaaaact gctcttacct taaactctag atgtttacat   2280
cgtttttgt tttgttttat gatgatgttg gtaatttgtg cctttaactc ggtttcctga    2340
accgccgagt taaagcatgt gttgtcttct ttgggaatac actcaggggt ctggaaggca   2400
gtttggtttt ttttgttgtt gatgatgttg ttcttgtttt ttaacacact tgaaaaaaaa   2460
aaaaggttgg agtaagcaga ctttcacatc cgacttggtg atgatcaacc tgctgtgtat   2520
ttaattttac atctttcgga agcactgcca cgggtcgttg gccagggtgg ccttccttca   2580
```

```
gttacgctgc tgtttgaaag gtgaatttca acacatttag tgcctctttc atttctcagt   2640
atattgtttg agagcttcta gtgacacttc tatgatggtg acaatgaatg tcacctgggg   2700
aacccgtctg ttactcacag gagaatttct tggctatgaa gtggaatgtt gtatggctgg   2760
gtcgaggaca acagtgggcc caactcaagg ctgttccgtg ggcttgaag attctgtggc   2820
attacctccc tggcctctgt tcacaccagc ttctaggcta gcaaaggagt ccttcttcta   2880
aaaggagggg ttggttttg cccatctaca ttttgcatct gctttcccca gtaccagtca   2940
tagaaaacta aacataattc tcagtttgaa acttgaaggg gggttgaggg gcagggaaac   3000
aacacaataa agccctagtg tggacgcctt aggttggtcc tgaggtaaaa atccccaagc   3060
ccttgtgaga tggaagcctt agagaaccac ctcgaagcac aagctgtgca cagagataaa   3120
ctgacacttt gtctacattc aaaggaaatt ccatgagcat tctttttaat ttaggaaaat   3180
tagtatctaa ttttctattc ttagatctta ttatctaaga atacaaatca tcaacaaatg   3240
tggacgacat tctgcgaagt tagatgctag ctctgtaggg ttccttaatt tcttttttaa   3300
gaagtataaa tttttttat attccccagg gaaaagaaga tttaatttga acatttatta   3360
atacaatacc tactttaaga gaaccaaatg ttgaaaactt taatttctag gaagtctctt   3420
attacacccc ccttccccca agataaaatg tctacattga gtgccaaaaa aagaaaaaga   3480
aaagcaatgt ggtgagctgg ggccagttaa acatttttga tcatgtaatc atggtatcga   3540
tgacagaaat tcacaaacta ctgccagaag gaaatatttt taaatacagc ttagggaaaa   3600
gaagaaaaaa aaagcctgaa tttttttttg gaagaaaagc atacaattat ttttcttcca   3660
accttagttc atcaaatttg ggcagtaaaa attcaacatc ctgaacagtt ttatttataa   3720
tcttgaattg tcaatttgta ttttgctact gacctgtgat caactattta aactttcatc   3780
tctagggata tttaaagaag aaatgcattt atatgcttat ataattgcaa ataaatccac   3840
tgtagagagg aaactcggag aattggtaat tatttgtgtg ttagaaatgg acaccatttt   3900
tcatgttaaa tagattttaa cctcgtatct atgcataggc taaggtggca catgaactgt   3960
gcatgtcatg ttatgggtaa agtaaattgt ttttacaatt cgttaggata ctatatgaac   4020
atgattctat atattgaaat cagaaacctt tccacacatg aaagtatcag aagctgccac   4080
cataatgact attttgtact tcaggctgct ttggaaataa tccccatcgc cttgctttgt   4140
aagttgataa tatcactatg catttctaca cattttataa atttgattta tgcagatttt   4200
gatacactgt atgtttctgt agaaattgta caaatattca aaattttatt agggtaaact   4260
caagaagctt atgtataact taattctggg ttgcttgttt tttaggtgag gaaaaataaa   4320
atattgtatt ttaatccata aaaaaaaaaa aaaaaaaaaa aaa                    4363
```

<210> SEQ ID NO 28
<211> LENGTH: 3589
<212> TYPE: DNA
<213> ORGANISM: Homo sapiens

<400> SEQUENCE: 28

```
gcctctttga ttggccaggc gtcttcggtc gctgtgacga cagagcggct ggcgggaatc     60
gcttcaccct gcgggcccag gaacgttctc ctgggtggcg cagaaccctg actcgccgtt    120
ttgtgcgcgt ttgcaactaa cccggatccg aggtacgaga ggtcccggag cgggacaact    180
gagagccaga tttcttttgt cgcgcagcaa ccacagcacc atgtcgtccc cggcatccac    240
cccgagccgc cgcagcagcc gacgcggacg agtcacccca acccagtccc ttcgaagtga    300
```

```
ggaaagcagg tcgtcaccca atcggagacg tagaggcgaa gattcttcca ccggagagct    360
actgccaatg cccacctcac caggagccga cctgcagagc ccacctgcac agaatgcctt    420
gttttccagc cctcctcaga tgcattcttt agctattcct ttggactttg atgttagttc    480
accattgaca tatggcactc ccagctcgcg agtggaagga accccaagaa gtggggtgag    540
aggcacacct gtaaggcaga ggccagatct gggctcagca cgaaagggtt tgcaggtgga    600
tctgcagtct gatggcgcag cagcagaaga catcgtacca agtgaacagt ctctaggcca    660
aaagcttgtg atttggggaa cagatgtgaa tgtggcaaca tgtaaagaga attttcagag    720
attccttcag tgttttactg atcctctggc caaagaagaa gaaaatgttg gcatagatat    780
tactcaacct ttgtacatgc aacaacttgg agagattaat attacaggag agccattttt    840
aaatgtgaac tgcgaacaca taaaatcatt tagcaaaaat ctgtatagac agctcatctc    900
ctacccacag gaggttatac caacctttga catggctgtc aatgagatct tctttgaccg    960
ttatcctgac tccatcttag aacatcagat tcaagtcaga ccttttaatg cgttgaagac   1020
aaagagtatg agaaacttga atccagaaga cattgatcag ctcatcacca tcagtggcat   1080
ggtcatcaga acatcacagc tgattccgga gatgcaggag gcctttttcc aatgccaagt   1140
ctgtgcccac accacccggg tggagataga tcgaggcaga attgctgagc cctgcagttg   1200
tgtgcactgc cacactaccc acagcatggc actgatccac aaccgatcat tcttctctga   1260
caagcaaatg atcaaacttc aagagtctcc tgaagacatg cctgctgggc agacacctca   1320
cactattgtc ctttttgccc acaatgacct tgttgacaag gttcaaccag gggacagagt   1380
gaacgtcaca ggcatatatc gagcagtacc aattcgagtt aatccaagag tgagcaacgt   1440
gaagtctgtc tataaaaccc acattgatgt cattcattat cggaaaacgg atgcaaaacg   1500
tctgcatggc cttgatgaag aagcagaaca gaaacttttt tcagagaaac gtgtgaaatt   1560
gcttaaggaa ctttccagga agccagatat ttatgagcgg cttgcttcag ccttggctcc   1620
cagcatttat gaacatgaag atatcaaaaa gggaatctta cttcagctct ttggtggaac   1680
aaggaaggat ttcagtcaca ctgggagggg taaattccgt gctgagatca acatccttct   1740
gtgtggggac cctggcacca gcaagtccca gctgctacag tatgtgtaca acctggtccc   1800
cagaggccag tacacgtctg gaaaaggctc cagtgcggtc ggcctcaccg cctatgtgat   1860
gaaagaccct gagaccaggc agcttgtcct ccagacaggt gccctcgtcc tgagtgacaa   1920
tgggatatgc tgcatcgatg agtttgacaa aatgaatgaa agcacaaggt ctgtgctgca   1980
tgaggtcatg gaacagcaga ctctgtccat tgcaaaggct gggatcatct gtcagctcaa   2040
tgcgcgcacc tctgtcctgg cagcagcaaa tcctattgag tctcagtgga atcctaaaaa   2100
aacaaccatt gaaaatatcc aactaccgca cacattgttg tcaaggtttg atctcatttt   2160
cctcatgcta gaccctcagg atgaggcata tgaccggcgt ctagctcatc acctggtttc   2220
attgtactac caaagtgagg agcaagtgga ggaggagttc ctggacatgg ccgtgctgaa   2280
agactacatt gcatatgccc atagtaccat catgccccga ctgagtgagg aggccagcca   2340
ggctctcatt gaggcttatg taaacatgag gaagattggg agtagccggg ggatggtttc   2400
tgcttaccct cgacagctag agtcattaat tcgcttagca gaagcccatg ctaaagtaag   2460
attttcaaac aaagttgaag caattgatgt ggaagaggca aaacgcctcc accgggaggc   2520
tctgaagcag tctgcaactg accctcgtac tggcattgtg gatatttcta ttcttactac   2580
aggaatgagt gccacttctc gtaaacggaa agaagaatta gctgaagcat tgagaaaact   2640
tattttatct aagggtaaaa caccagcctt aaagtaccaa cagctgtttg aggatattcg   2700
```

```
gggacagtct gacacagcaa ttaccaagga catgtttgaa gaagccctgc gagctttggc   2760
tgatgatgat ttcctaacag tgactgggaa gactgtccgc ctgctctgag ctgcatggcc   2820
ctcggactag agtcactcac tgttgttatt gctgcaaaag gagtctgaaa ggcagtattc   2880
cactatataa acctcttcta ttcctggaat gtattttgtt agtaaatgta tgttttcacc   2940
tttttttaac attttaaatt atcaacatat agtagagttt atattctcaa tatgccatat   3000
tttttaagca gcttgcttct tacctgtttg tacacagaga gcctaagccc agttttggag   3060
gttttttttta atgtaggggc tgtgcctttg ttgtgttgca atgctgggga ggaaggtaag   3120
agtaccatgc atgctgtatg tagaggctat gtccttactg tgtggagcat tgtgtgcttg   3180
gtataactgg cagccgtaca tcctttactg tgatatgatg ggctaatgat ttttatagca   3240
cctggactta actttcttta cagagacttt ttcccataac tattattaga acaaagatat   3300
gcttgaaaaa ttattaaatc aagttgcctt ctgtttttttc ctaatatgta aaacattttc   3360
ctaaataaat gatagaaaag taatacttgg tttaaaatta tttctcatta agagcagaac   3420
tttgctaaag actatatttt ttgaaatcat aatagtgctg gataggttat aaaaaaatca   3480
aggtatgaat ttcattaatt tttatagatc cttagattat tagtttcaaa gccattgtag   3540
cattaaatct tgtgtaaata ttacaataaa tctctaaacc atttgaatt              3589
```

<210> SEQ ID NO 29
<211> LENGTH: 4028
<212> TYPE: DNA
<213> ORGANISM: Homo sapiens

<400> SEQUENCE: 29

```
cgaggcggcg ggcccgactt acaggctccc ggggcggtgg cggcaggcgc tgagccggcg     60
gagcgcggag cgggcgaagg agacgggcgg cgcgagcccg cacccttccg cgcggtgcgc    120
cgcgacacca tggagcccgc cgtgtcgctg gccgtgtgcg cgctgctctt tctgctctgg    180
gtgcgagtga aggggttgga gttcgttctc atccaccagc gctgggtgtt cgtgtgcctc    240
ttcttgctgc cgctctcgct catcttcgat atctactact acgtgcgcgc ctgggtggtg    300
ttcaagctga gcagtgcgcc gcgcctgcac gagcagcgcg tgcgggacat ccagaaacag    360
gtccgggaat ggaaggaaca gggcagtaag accttcatgt gcacggggcg cccaggctgg    420
ctcactgtct cgctgcgagt cggaaagtac aagaagaccc ataagaacat catgatcaac    480
ctgatggaca tcctggaggt ggacaccaag aaacagattg ttcgagtgga gcccttggtg    540
tctatgggtc aggtgacagc tttgctgaac tccattggct ggaccctgcc tgtgttgcct    600
gagcttgatg acctcacagt gggggcctg atcatgggca caggcatcga gtcatcgtcc    660
cacaagtatg gcctgttcca acacatttgc actgcctacg agctgatcct ggcagacggc    720
agctttgtgc gctgcacacc gtctgaaaac tcagacctgt tctatgccgt gccctggtcc    780
tgtgggaccc tgggcttcct ggtggctgcc gagatccgga tcatcccggc caagaagtat    840
gtcaagctgc ggtttgagcc tgttcggggc ctggaggcca tctgtgaaaa attcacccgc    900
gagtcccagc ggctggagaa ccacttcgtg gaagggttgc tgtactccct ggatgaggct    960
gtcatcatga caggggtcat gacggacgac gtagagccca gcaagctgaa tagcattggc   1020
agttactaca agccctggtt cttcaagcat gtggagaact acctgaagac aaaccgggag   1080
ggcctcgaat acattcccct gagacactac taccaccgac acacgcgcag catcttctgg   1140
gagctccagg acatcatccc tttcggcaac aaccccatct tccgctacct cttcggctgg   1200
```

-continued

```
atggtgcctc ccaagatctc cctcctgaag ctgacccagg gcgagacgct acgcaagctg   1260
tacgagcagc accacgtggt gcaggacatg ctggtgccca tgaagtgcat gtcacaggcc   1320
ctgcatacct tccaaaatga catccacgtc taccccatct ggctgtgccc attcatcctg   1380
cccagccagc caggactagt gcatcccaag ggagatgaag cagagctcta cgtggacatc   1440
ggggcatacg gggagccacg tgtgaagcac ttcgaggcca ggtcctgcat gaggcagctg   1500
gagaagtttg tgcggagtgt gcacgggttc caaatgttat acgccgattg ctatatgaac   1560
cgcgaggaat tctgggagat gttcgatggc tccttgtacc acaagctgcg caagcagctg   1620
ggctgccagg acgccttccc tgaggtgtac gacaagatct gcaaggcggc aaggcactga   1680
gcagggcacc tggggagcca gctgcatgga cctgctctcc ctcgctcgct ccggcttctc   1740
tgctttccca ggtctcagaa aagaaacccc tccacatccc cgaggcagcc cgatggcttc   1800
cagggtggct cgggcaagtg gaagcacgtg gagtcagaca gacctaagtc ccaggcccag   1860
attagccact cgttagctgt gtgactgact ctgggctagt cacctggccc ctgtgtgccc   1920
cgtgttcatc tgtgaaagga ggtaaaaaaa aaaaaatatc tacctgctgg atgtcacccc   1980
acactaaggg cttccaccac tgcttccatg caacctcacg cctggctcct gctttggatc   2040
taacagctga gtccagacag gctccccaca ggtcaccctt gcacgggttt ggccaacacc   2100
atgaaggagt tgccttggag tttcacctgc atagcttgca tcagccccga gagggcaaag   2160
gagggtcagc cttccacttg gcctcggggg tggggcaggg ggcatctgat tggcaggcag   2220
gcccaggatg tgctgtgcca aagccaggtc tactccaaag tcctctctgc catcttcgga   2280
ccatcctggc cctacttctg tgtgctcgag ctgccccagc catcactgag cccactcagg   2340
actgctcctg gaagacatct caaggtggga agcctggctt tcctgggctt tgctttctta   2400
actcccacca tccaggcctc ctctagagtc cactgagtca caatgggggc acatgctcat   2460
gactgtgtca cttaggggcg gtccccacac tgagtgagaa aggggcatct gccctgttgc   2520
tactgtgagg accctccctg ggttagaaa gaaagcatcc agggtcactc atctccccct   2580
cccccatttt gttccctccc ccccccctccc cccccccccc cccccggctc tagttaattt   2640
cagtgcctta caaatcctaa gctcagagaa agttagctcc atttccgttc ccaagggagg   2700
ggcctctgag gtccttctgc cttgttgatg aagagtggtt ggttgtagag cccccacctt   2760
cagaactgcc tggcccagct ggaaacccag agtctgaggg ggaatcaggt tctggaaggc   2820
aagccagaac tccagagctg agctggtcac agtcactcct cccccaccac ccctgcccct   2880
ccagaggctg cagttttctc gcctgtcact tggaacatta gagctcctga agcctgtctg   2940
tcttaagacg ttgggaaagc ctcgtgttga aagccggggg agcttaaatg atccaggtgg   3000
tagctaggga ccgtccatca gtggtccttc cctccaccgc cacgccagct cctgggtcgt   3060
tttcatttat ctggcagagc ccaggaccct tagaatcata ttttagctga aggatgctca   3120
ctgatgcggc cgagggcttg ggatactgca cagtgctact gtgtcctgtg aaggctggtg   3180
cactcagggc tgtgggaagg cagaatcacc tcatccattt ggcctgtgaa ggaagtaacc   3240
tcactttgct gtctgagcag catgtattcc tggcatgggc tctcctagtg gtccatgtgc   3300
atccttgcgc atgtgcactc gctcgcagac tgatgaccct gcttgctgca gatgaatggt   3360
caacgcgagc taggttagtt agtgtgatgt ataaggcgcc atcattcctc aagtcaagcc   3420
tccatcccaa agcacctgga gctgtggcaa tgatgccagc aacctgtgtc acccaaaata   3480
gtcaaaatcc agccctccac agacactccc caggacctgg ggagggaagg gattttgagt   3540
cacattagcc tcaggttagt gtttggctcc agtaatatct tgcccgaaaa gtggtcgtct   3600
```

```
tccaagcatg gtgttctggg tcccagcctt gtcttatcgc ctgtcctgtc agtgtccaac   3660

cacacggtgg cttggtgggg tcactcagct gctatgggac agcacatgtg ggaagtcaac   3720

gcaagcctct cccctccgtg gctctggttt cttggctgca tggttctctg taaattcagt   3780

tgtagccact gtctttggct agaaagctga attggctgtt gctgaaagga aggaggggat   3840

gggtgtggcg atgtgtgctg tgtgatttgt tgtttttttt tttttaattt ggtcatgggg   3900

accaaggaga aggcatgaat ccctgtattt ggctcttgca gcctcaggca ctgtgcctac   3960

tctccaggtc atgtccctgt ggttctgggg ccaccacttg tgtaaaataa agtacagcct   4020

ggacgcta                                                            4028

<210> SEQ ID NO 30
<211> LENGTH: 3632
<212> TYPE: DNA
<213> ORGANISM: Homo sapiens

<400> SEQUENCE: 30

gaaccgagga tttgggcggc cggaagagcc gcgccgtaac ggccgccatc ttgtttgttt     60

gagtgaatcg gaaaaggagg cggcggccgt ggcggtggcg ggagcagctc cgaggctaca    120

ccgcacaagg gctccccctc tccccgcccc ctcccctgac ccttcccccc ctccccgggc    180

cacccacccc tcccggctcc ccgccgagat ccaggtttct tcttatttca tagcaaataa    240

gaaaaatgtt ctacgcacat tttgtcctca gtaaacgagg gcctctggcc aaaatctggc    300

tggcggccca ttgggacaag aagctaacca aagcccatgt atttgagtgc aacttagaga    360

gcagtgtgga gagcatcatc tcaccaaagg tgaagatggc gctgcggacg tcaggacacc    420

ttctcctggg agtagtccgc atctatcaca ggaaagccaa atacctcctc gcagactgta    480

atgaagcatt tattaaaata aagatggcgt ttcggccagg tgttgtcgat ctacctgagg    540

aaaatcggga agcagcttat aatgccatta ctttacctga ggaattccac gatttgatc     600

agccactgcc agatttagat gatattgacg tcgcccagca gttcagcctg aaccaaagca    660

gagtagaaga gataaccatg agagaagaag tcggaaacat cagtatccta caggaaaatg    720

actttggtga cttcggaatg gatgaccgtg aaataatgag agaaggcagt gctttcgagg    780

atgacgacat gttagtgagc accagcgctt ccaaccttct cctcgagcca gagcagagca    840

ccagcaacct gaatgaaaag atgaatcact tagagtacga agaccagtac aaagatgaca    900

attttggaga aggaaatgat ggcggtatat tagatgacaa acttataagt aataatgatg    960

gtggcatctt tgacgatccc cctgccttgt ctgaggcagg ggtcatgttg ccagagcaac   1020

ctgcacatga tgacatggat gaagatgaca atggctcact gggtgggccg gatagtcccg   1080

actctgtgga tcctgtcgaa ccgatgccaa ctatgactga tcagacaact ctcgtcccaa   1140

acgaggaaga agcttttgcg ttggagccca ttgatataac tgtcaaagag acaaaagcca   1200

agaggaagag gaagctgatt gttgacagtg tcaaagaatt ggatagtaag accattagag   1260

cccagcttag cgattattct gatattgtta cgactctgga cctggctccg ccaaccaaga   1320

agcttatgat gtggaaagag acaggaggag tggaaaagct cttcttttta ccagcacagc   1380

ccctgtggaa taaccggcta ctgaagctct tcacacgctg ccttacccca cttgtaccag   1440

aagaccttag gaagagaagg aaagggggag aggcagataa tctggatgag ttcctcaaag   1500

agtttgagaa tccagaggtt cccagagagg agcagcagcc acagcagcag cagccacagc   1560

cgcagcgaga tgtcatcgat gagcccatta tagaagagcc aagccgcctc caggactcag   1620
```

```
tgatggaggc cagcagaaca accatagaag aatcagccat gcccccacca ccccctcaag   1680
gagttaagcg gaaagccggg caaatagacc cagagccttc gatacctcct cagcaggtag   1740
agcaaatgga aataccacca gtagaacttc ccccagagga gcctccaaat atctgtcagc   1800
tgatcccgga gttagagctc ctaccggaga aggagaagga aaaagagaag gagaaggaag   1860
aggaggagga ggaggaggat gaagatgctt caggggggtga tcaggatcaa gaggaaagga   1920
gatggaacaa acgcactcag cagatgcttc atggtcttca gcgagctctt gctaaaactg   1980
gagcagagtc tatcagtttg cttgagctgt gtcgaaacac aaaccgaaag caggcagcag   2040
caaagttcta cagcttttg gttcttaaga agcagcaagc catcgagctc acacaggaag   2100
agccgtacag tgacatcatt gcaacccctg gaccacggtt ccatattatc tgaggagcta   2160
gatgtgttcg agctagtgat aactcactag tacatacaaa ttgcccccgt gtgcagggca   2220
ccaaaaccct ttaagaaagt ttttagattt ctgtttgtac aaaaatcttt gccttttctt   2280
tcttcttttt ccccccagtg tttctaattt tgtcaaccat atttttaagg gaaactgctt   2340
atttgggttg ggtttgtatt cctggagaaa acagtagccc aagaacccag aagactttta   2400
acagttcaga acagatgtgt gcaatattgg tgcatgtaag aatatggagt aacagtcaaa   2460
aggcaccatt tttaatgtta gttttccatt actatgttga aaggaaaacc tgcctaggaa   2520
aatgcctgac actttaagaa ctgtggtttg agtcccttga caggaagaga aaaatgtctt   2580
cccatcagtg aaaccaacgg tctggttaac cactgtagta gggatagtgt gtgaagcatc   2640
gtgcttgtct tcttgatcat gtttaaagta aatccacact gagcaagaat ttgtgaggtt   2700
gtgctgactg atcttcttcg gctattatgt tctgaaatca ttccgtgagt cttaggacct   2760
ctgatgctat gcaccgcagc tcagaacgat cagacgtcta cagtggcgtg actcctcagg   2820
ggctgcagat cactctcaga ggtgtttgga tgtttgcttg aataatgaga tcatggaagc   2880
agacattccc ctgcctgctg aagggcagac caatgagaga ctaccccaga ttgacttcct   2940
ttaagcaaac agtgctgtaa aaactaatgg cttctctgat atttattata aatgttagta   3000
ctcatctttt tccaaggctg cacactcctg tatttgcaac ttattttttaa taactttgca   3060
actataatcc tgtatcagtt tcctataatt taagtggaga aaaacatcct aataaaggct   3120
ttattattaa cagaccagat agcaccagaa attatgtgac tatataaata tcaaaacatg   3180
ttcactttgt aggacaaaat tatgttgaaa agttctagct taagtgttgg cacttttatg   3240
ggggggaaat cagttttaaa actaagactt ccatgtatac ccagtaattt aaaattatgt   3300
gaaatatttt aaatttgtga actcgtaatt actactttaa tgattcagtt tctcgagaat   3360
ggtaattgta taaaattgct cttgcagttt tcttttcaat acgacgtgcc tgtaaccatg   3420
gatgtcccct ttgtaaaaag acactgtaga taattgaatg tttgattata gaaaggtcgt   3480
tagtttcttg ttaaacattt tgttagtcca gtttttgtcg cttattgggt ttaatattgt   3540
tcttgaaaat agtcgatgct atgttatgta taacttttct aataaaagtt gtgtttcaag   3600
ctgtaaaaaa aaaaaaaaaa aaaaaaaaaa aa                                 3632
```

<210> SEQ ID NO 31
<211> LENGTH: 1333
<212> TYPE: DNA
<213> ORGANISM: Homo sapiens

<400> SEQUENCE: 31

```
cagctcgggc gcggggcttc taaccacgta gcaggcttct atcaccggct tgccagtcgt     60
agcccaacgg acaggaggga acatgggggc cctggcagct aggcgctgtg tcgagtggct    120
```

```
cttgggcctc tacttcgtct cgcacatccc catcacgctg ttcatcgacc tgcaggcggt    180

gctgccgccc gaactatacc cgcaggagtt cagcaacctg ttgcggtggt actcaaagga    240

gttcaaagac cctctgatgc aggagccccc agtgtggttc aagtccttcc tgctctgtga    300

gcttgtgttc cagctgcctt tctttcccat tgcggcatat gccttcttca aaggaagctg    360

ccggtggatc cgaatccctg caatcatcta tgcagctcac accataacga ctttaattcc    420

aatcctctac acactcctgt ttgaggattt ctctaaagcc gttgctttca agggacaaag    480

acccgagagt ttccgtgaac gactgaccct cgtaggtgtc tacgcccccct atttaataat    540

ccccctcata ctcctcctgt tcatgcttcg gaacccgtac tacaagtatg aggagaaaag    600

aaagaaaaaa tagggacggc caccagcctg gtggggaaga ccccacagca cagttgcctt    660

ttggacaaca caggaaaact gccccaaaca tgtttcagca gcatttgaaa caccaacagc    720

agtgcataca aacaagacag tggtgggaga cgtgccaggc cttcaccttt cagcaggggt    780

gtgaccaagt tacagcaaaa tggtgccaaa gcgctaccac agcactgcta aaaaggccag    840

gtgggaagcc ggttagctcc tgacctggaa tgcacacacc tgaccaagtc ctcacctcga    900

ccttgatagt caacaaatga gcagtatttt gtctctttag cactttttaa catggtttcc    960

tgcccacacc tccacctctg ggagaaaaat atattatagc ctcacatgag tccaagccag   1020

aaatgggtta cagggaagga aggtgcctcc atttctatct tgaacagata gcctgctctg   1080

ggttattctg gtgctggttc tatgaacggc tctcatgtcc ctactctggc acctcacccc   1140

actgggcttc ctagtacgca ggcttgtgag ggtgactgga ctgtccagtg tatgtctgct   1200

gcttgttcca ctgactctac agaaacaaaa cccggtgggt gctagacagt gctggctctg   1260

cttgcaagcc atgttgctgt ggttgttact tatgtgtctg gtccaaataa aggcagctgc   1320

tgatttgttg tta                                                      1333
```

<210> SEQ ID NO 32
<211> LENGTH: 3518
<212> TYPE: DNA
<213> ORGANISM: Homo sapiens

<400> SEQUENCE: 32

```
gagtcccggg attggcagag gtagccgctg tcccgccctc tgtcccctcc cggcgctgcc     60

cgagtcgggt gggtcggtgg ctataaagct gcggagggcg ggaggcacag tctgcggtct    120

ccttgctttg ctcgttcttc ttccagggtc tgatcccctt tggctctttc accatgcctg    180

ggtcacttcc tttgaatgca gaggcttgct ggccaaaaga tgtgggaatc gttgcccttg    240

aaatctactt tccttctcaa tatgtcgatc aagctgagtt ggaaaaatac gatggtgtag    300

atgctggaaa gtataccatc ggcctgggcc aggccaggat gggcttctgc acggatcgtg    360

aagacatcaa ctctctttgc ctgactgtgg ttcagaaact gatggagaga catagccttt    420

cctatgattg cattgggcgg ctagaagttg gaacagagac aatcatcgac aaatcgaaat    480

cagtgaagtc taatttgatg cagctgtttg aggagtctgg gaatacagat atagaaggaa    540

tagatacaac caatgcatgc tatgggggca cagctgcagt cttcaatgcc gtgaactggg    600

tcgaatccag ctcttgggat ggacgatatg ctctggtagt tgcaggagac attgctatat    660

atgccacagg aaatgccaga cctacaggtg gagttggagc tgtggccctg ctaattgggc    720

caaacgctcc tctaattttt gaccgagggc tccgtgggac acacatgcag catgcctatg    780

acttttacaa gcctgacatg ctctccgagt accctgtggt cgacggaaag ctctccatac    840
```

```
agtgctacct cagcgccctg gaccgctgct attctgtcta ccgcaaaaag atccgtgccc    900
agtggcagaa agagggaaag gataaagatt ttaccctgaa tgattttggc ttcatgatct    960
ttcactcacc atattgtaaa ctggtgcaga aatctctagc tcggatgttc ctgaatgact   1020
ttcttaatga tcaaaacaga gataaaaaca gtatttacag tggactggaa gcctttgggg   1080
acgttaaatt agaagatact tactttgaca gagatgtaga aaaggcattt atgaaggcta   1140
gttctgagct attcaaccag aaaacaaagg cgtctttgct tgtgtctaat cagaatggaa   1200
atatgtacac atcctctgtc tatggttccc tggcttctgt cctggcacag tactcacctc   1260
agcagttggc agggaagagg gttggagtgt tctcttacgg ttctggcttg gctgccacgc   1320
tgtactccct taaagtcaca caagacgcca caccaggatc tgcccttgat aaaataacag   1380
caagtttatg tgaccttaaa tcaaggcttg actcgagaac ttgtgtggca ccggatgtct   1440
ttgctgaaaa catgaagctc agagaggaca cacatcactt agccaactat attccccagt   1500
gttcaataga ctcactcttt gaaggaacgt ggtatctggt cagagtggat gaaaaacaca   1560
gaaggactta cgcccggcgc cccttcacaa atgaccacag tttggatgaa ggaatggggc   1620
tcgtgcatag taacacagca acagagcata ttccaagccc tgctaagaaa gtgccaagac   1680
tccctgcaac ctcggccgaa tctgaatcag ctgtcatcag taacggggag cactgagagt   1740
ctgtggcctt tacagaggct cggggccggg atggggtatg gaaacggttg gaggaatgga   1800
tgtcttggga caattttgca gattatgtgt tgcttaaaat gtaatgtaac tgacacagag   1860
cccagaaagc tattgtgttt ttggaaaagt ctctgctgaa ctgaacttgc taacatgctt   1920
cctgttgtgg tctggccagt ggtaaatgta ctgcagtgat gttaaagggc tctgtagaac   1980
tttatacctc tctggatgtt tatacgcatg cagtttagtt ttcagatgtg gtatgaactg   2040
agtgcttctg acagcaaaag gcagaggtac tagtgtccaa tttttaaaaa aacgtttttt   2100
tttttctttt tttatgtgta agaattttat acttaaagta tctgtagctt ttggggtgaa   2160
aaaaaacttt tctaggttgg gggttgtgaa atttaaatgt tacacacaag accctgtttg   2220
aaaatggcaa ggcaaacatt tatctttttc aaagatttgt aaatcctgaa gagaaaaaag   2280
agggtatggt tctaagatct ggatgaacca tcagtgagag gaaggttagc tgtaatcacg   2340
tgagcagaaa gatgctggca ctgagcaggc ctccatcgtg ttgggcaggg tacacctggg   2400
cgttgtggac acagctgcgg gaactttttg gccaggtctc cgtggcagtg ctcagcagca   2460
ctgagagatg gcgctggagc ttgctgccct cctgagcacc ctccctgggg gataaagtgt   2520
gaagtaggaa ggatggggca ggcattatta ggttagtgtt acagatccag tttatagact   2580
gacagcttca attcacggga cacctttttt cctttgtggt ttgtgtattt ctgtgttttg   2640
tttgtttttg tatccgttcg aaaatttaac ccacattttc acatagtgaa aatttcacat   2700
ggtctgatta gccaaaaaag aataagatct agaagtagaa ctcacaccat tttttttctt   2760
aactttgatt tctaaaacaa caaaaactac cacatgagct gaataagaaa attcactagc   2820
aagttctctg gatgattttt ggtgctgaac aatgacatga gcctcagact gtaaaataga   2880
ggtagttgga actaatgtac agaactaaat ttcttaacct tatttgcgtt taattctgtg   2940
aagtttcagt tatctaaaat aaatgtgtaa tgtttcagat tgcaaggtga taagtaatgt   3000
agcatttgta agatactctt gtcaatatta actagtagga ttttgatttg tacagtttta   3060
attggttaaa atgatctcat tttaacatcc actgctatag atgaataatg taagttcaga   3120
tttaatgaat ggtggggaga tggtgcatgt aatttttttg caagtattga gagttctgta   3180
tgttttgaaa agagtaattt taacgtttgg gtgccaagaa gtgggttttc tcagagtcca   3240
```

```
ttgccggcaa tgggcaagcc tggcggtact ggcacggagc gttaaccaca ccttactaat   3300

agcaaggcca ataactttga aataaagttt tagacaaata tttcagctct ttgagtgttt   3360

tttttttccc tgagggaaca gtttgtttat ggagtcagca aataggtatt ttaaacgtgg   3420

gccttcagtt ggttactcat ttgcttagtc ttcaaacatt tccaaaccca gtataaataa   3480

cacactcttt ataccagaaa taaactgtat tgcctgtg                           3518
```

<210> SEQ ID NO 33
<211> LENGTH: 1824
<212> TYPE: DNA
<213> ORGANISM: Homo sapiens

<400> SEQUENCE: 33

```
agaggtagtg aggaggccgc tgcacctgcc aggacttgcg cttagaccgc tgtctgtcgc     60

ggggacgcca ggaataaaag gtccctcgca gagatttgaa aatggccaca aacaaaagtg    120

ttggcgtgtt cagctctgca tccctggctg tggagtatgt ggactcactg ttgccggaga    180

atcctctgca ggagcccttt aagaatgctt gggtctacat gttggacaac tatacaaagt    240

tccagatcgc aacctggggc tccctgatag ttcacgaagc catctatttc ttgttctctt    300

tacctggatt cctattccag tttatacctt acatgagaaa gtacaagatt caaaaggata    360

aaccagaaac cttcgaaggc cagtggaagt gtttgaaaaa aattctattt aatcattttt    420

ttatccagtt gcctctgatt tgtggaacat actattttac agagtttttc aatattcctt    480

atgattggga aagaatgcca agatggtact taactttggc aaggtgtttg ggctgtgcag    540

tcattgagga cacctggcat tatttcctgc acagactcct tcaccacaag agaatttata    600

aatacattca taaagtccat cacgagtttc aggctccatt tggaatcgaa gcagaatacg    660

cacatccctt ggaaaccctg attcttggga caggattttt catcggaatt gtgcttttgt    720

gtgatcacgt aattctcctg tgggcatggg tgaccatacg tttgctggaa accatcgatg    780

tgcacagcgg ttatgatatt cctctcaacc cgctgaactt ggttcctttt tatacgggcg    840

ctcggcacca tgatttccac cacatgaact tcattgggaa ttatgcctcc accttcacgt    900

ggtgggataa actctttggg acagatgccc agtatcatgc ctacattgaa aaatcgaaga    960

agcttgggaa aaagtctgat tgagcacccc cactcgacgc cttcctcaac tgcagctggc   1020

cactaacact gcttctgggg acttggctgc caagtgataa aaacgttaac gacctttaag   1080

tactcttcca gatgagagct cttctacctt acgtccaaga tctgtatatg tgggaacaaa   1140

taagtaaata tatatacata tatatatatt taagtacagt tttcatcagg aggttttaaa   1200

ggccatattg ctaacctcac caaaaggttt cgggaactgg aggaagtatt aatgtacaac   1260

tcaccacttc atgccatagg aggctgaagt tgacgttgcc ttttaagcct tttacataca   1320

ctggtcagtt cggaaaattc tcaacaataa tgtttgcctt ctagtttaag acatggtgta   1380

ttttagaaat tacctgaagt gaagctatca cgaagtgagt gtatcacctg gtgagcgagt   1440

gactgaaacc tgctctggtc tgggtttgac caggttagga ctattctttc tgtgaaggat   1500

tgtttgattg tagtaactct attggcatct tgtaaattgg ctcatttcct acgtgatgta   1560

catagaatat tatagcctaa agattttcca gttacttgcg gtctttttaa attgaggagc   1620

cccacttcca ctgtccaccc cttgtctttg tgtgtcaggt gatcattgaa atcgtatctt   1680

gagcttgaat tcacttctct gtctgtttcc ggagctggtg aaataaatgt gatttttgtc   1740

cgatccttct ggttttcatg aagattagct gccatgtttt attcttataa ggaaaagcac   1800
```

```
agagatcatt aaagtaagtt ttac                                          1824

<210> SEQ ID NO 34
<211> LENGTH: 3389
<212> TYPE: DNA
<213> ORGANISM: Homo sapiens

<400> SEQUENCE: 34

ggcgccatct tccgcggcgc ggattgaatg agcgcgccgc attcgggcaa ccgaggtgat     60

tctcccgccg ccgccacctc cgccatggcg tctctgccgc cccacgcggg gcccgccacg    120

ccgctgtcgc ccacgcgtct gtctcggctg caggagaagg aggagctccg tgagctcaac    180

gaccgcctgg cacactacat cgaccgtgtc cgcgcgctgg agctggagaa tgataggttg    240

ctgctccgga tctccgagaa ggaggaggtg accactcgcg aggtgagtgg catcaagacc    300

ctgtacgagt cagagctggc tgacgcccga cgggtactgg atgagacggc ccgtgaacgt    360

gcccggctgc agattgaaat tggaaaggtg caggctgagc tagaggaggc caggaagagt    420

gccaagaagc gggaaggtga gctcacagtg gcccagggcc gagtgaagga tctggaatca    480

ctgtttcacc ggagtgaggc tgagctggcc acagccctca gtgacaagca gggcctggag    540

acagaggtgg cagagcttcg agcacagctg gccaaggcag aagatggtca tgctgtggcc    600

aagaagcagt tggagaagga gacgctgatg cgtgtggacc tggagaaccg atgccagagc    660

ctgcaggagg agctggcttt cagcaagagt gtgtttgagg aggaggtacg ggagacccga    720

cggaggcacg agcggcgctt ggtggaggtg gacagcagcc ggcaacagga atatgacttc    780

aagatggctc aggccctgga ggacctgcgc agtcagcacg atgagcaagt gcgcctgtac    840

cgggtagaac tggagcagac ctaccaggcc aagctggaca acgccaagct gctctcggac    900

cagaatgaca aggcagccca tgcagcccgc gaggagctca aggaggcccg catgcgcgtg    960

gagtccctca gctaccagct tttaggcctc caaaagcagg ccagtgctgc agagaaccac   1020

atccatgagc tggaggaggc cttggctggg gagcgtgaca agttccgcaa gatgctggac   1080

gctaaggaac aggagatgac ggaggtgcgg gacgccatgc agcagcagct ggcagagtac   1140

caagagctgc tggacattaa gctggccctg gacatggaga taagcgccta ccgcaagctg   1200

ctggagggcg aggaggagag gctgaagctg tctcccagcc cttcatcacg gatcaccatc   1260

tctcgggcca catcgagcag cagcagcagc agcggggttg gcatgtctgt gggccagggc   1320

cggggcaagc gccggcggct ggagactgag gacacctcag gctcacccag cagggcttcc   1380

agagtgagca gcggctcccg cctggctcag cagactgtgg ccacgggtgt tgtgaacatc   1440

gacgaggtgg acccagaggg caggttcgtg cgccttaaga actcttcaga caaggaccag   1500

tctttgggga actggaggat caagagacag gttctggagg gtgaggacat tgcctacaag   1560

ttcacaccca agtatgtcct gcgggccggc cagactgtca cggtgtgggc agctggcgca   1620

ggggctaccc acagtccccc atcaaccctt gtgtggaaaa gccagaccaa ctggggccct   1680

ggggagagct tccgcactgc cctggtcagt gccgacggtg aggaggtggc cgtgaaggct   1740

gcaaagcact catctgtcca ggggagggag aacggggaag aggaggaaga ggaagaggca   1800

gaattcggtg aagaggacct cttccaccag caggggggacc caaggactac ctcaaggggc   1860

tgccgactga tgtgaaacct gccccacggt caccatggtc cccagagccc ctaaaactac   1920

ttttttatgg tctgctctca ctagtccttg gtctgtttct cgatgactgt taagcaacca   1980

tgagaatgtg ggtgggctct gctgggtttc cgagatggag gtgccctctg cccaccggcc   2040

tgacctggcc ccatgccgtc aagatggtat agaggcctgg ggctaggaac ccgcaggctg   2100
```

```
agggacttgg gcctggatct ggggcaggag aatggctgct agctcagggt ggactttgta   2160

tgaaactggt gattcagttg ttttctttga agcctttcaa atcaaatcaa attcagaatc   2220

caagagtgct gtggggccca ctagcctgtc aggatgtggt ggctcttagg acacagggca   2280

gaccctcctc tcctggagtt gatggcacct gaaaccaggg atggcccagc tttgtgctct   2340

gaatctgaag ggtttataac agtccccagc tccagggcat tcacaggctt ctctggtccc   2400

agattctgaa ttgttctagt cccttctaaa gcggaggacc aaggaggagc gagttcacac   2460

atgggacgac gcctcccatc ctaagactga aggggacagg caaaccgtgg gcgttgtgcc   2520

ttcaggagca aaggctgcag gttcccagcc agtgactgct cacatgagtg tggccacact   2580

agctatgctc ctggcctctc ctgtatgaat actgtgtggc ccctctgtgc cccacctcga   2640

tggcaaggcc tggaaacttg cttccctgca acttagtgcc aggagccagc cagtttcacc   2700

tgtcacctcc ccaccactga cacatggtat ttttttaaag aatatttatt tttttacatc   2760

ggtcagtaac gcagctcact gggatgatgc tctggggggtt caggcctgga gctgccacaa   2820

ctggcagctt cctttactga gctagggcga gttctttctc tctcctggca cagctgatgg   2880

taggaagagt ccaggcctag tcttccccca aggcaagagc tcttggccac aggatgccac   2940

cactgccacc aacctccaga acccaccagc cacctcctgc ttctagatac ctccgttttc   3000

tttgtgaccg gcgttggatc ctggatagtt atggctggct gcagtcactg cgcagctctg   3060

ctgccttgcc cacagggcag gtgtactctg cactggagct agcttccttg tatttgagga   3120

gcaggtctag agtaatctgc aggtcctcag ggtctgtttt ctggccctgg ctaggtgaga   3180

tggttaccgg agtggcactg ctgctgggga gccgccggca ctgcgcacat cgctcagctc   3240

tacagattgt ttcttttata agatgcatgc caaacgtgtg ttccaccttt tcttttacgc   3300

ctatgatttg taatatacat tttacaactg gaaacttttg tatactcaaa taaacattga   3360

ctttaactgc aaaaaaaaaa aaaaaaaaa                                      3389


<210> SEQ ID NO 35
<211> LENGTH: 3564
<212> TYPE: DNA
<213> ORGANISM: Homo sapiens

<400> SEQUENCE: 35

tggatacgtg catctgtccg gagagaactg ccagatccgc ggccccgcga tggttctggc     60

cccactgcta ctggggctgc tgctgctacc cgcgctctgg agtggaggca ctgccgagaa    120

gtgggaagag accgagctag atcagctatt ttcagggcct ttaccaggga gactcccagt    180

caaccacagg ccattctctg ctcctcactc cagccgggac cagctgccac caccccagac    240

tggaagatca catccagcac acacagccgc tccccaggtg acctccacag catcaaagct    300

cctacctcct gttgcgttta atcacaccat tggacacata gtactgtcgg aacataaaaa    360

tgtcaaattt aattgctcca tcaatattcc taacacatac caagaaacag ctggcatttc    420

atggtggaaa gatggaaagg aattgctcgg ggcacatcat tcaatcacac agttttatcc    480

tgatgaggaa ggggtatcaa taattgcatt gttcagcata gccagtgtgc agcgctcaga    540

caatgggtcg tacttctgta agatgaaggt gaacaataga gagattgtat ctgatcccat    600

atacgtggaa gttcaaggac tcccttactt tattaagcag cctgagagtg tgaatgtcac    660

cagaaacaca gccttcaacc tcacctgcca ggccgtgggc cctcctgagc ccgtcaatat    720

cttctgggtt caaaatagca gccgtgttaa tgaaaaaccg gaaaggtccc cgtctgtcct    780
```

```
aaccgtacct ggtctgacag agacagcagt cttcagctgt gaggcccaca atgacaaagg    840
actgacggtg tccaagggtg tacatatcaa catcaaagta atcccctccc cgcccactga    900
agtccatatc ctcaacagta cagcacacag catcctggtc tcctgggtcc ctggttttga    960
tggctactcc ccacttcaga actgcagcat tcaggtcaag gaagctgacc ggctgagtaa   1020
tggctcagtc atggttttta atacctctgc ttcgccacat ctgtatgaga tccagcagct   1080
gcaagccctg gctaattaca gcatcgctgt gtcctgtcgg aatgagattg gctggtctgc   1140
agtaagccct tggattctgg ccagcacaac agaaggagct ccatctgtag cacctttaaa   1200
catcactgtg tttctgaacg aatctaacaa tatcctggat attagatgga cgaagcctcc   1260
aattaagcgg caggatgggg aactggtggg ctaccggata tctcacgtgt gggaaagcgc   1320
agggacttac aaagagcttt ctgaagaagt cagccagaat ggcagctggg ctcagattcc   1380
tgtccaaatc cacaatgcca cctgcacagt gagaatcgcg gccattacta aggggggcat   1440
cgggcccttc agtgagccag tgaatatcat cattcctgaa cacagtaagg tagattacgc   1500
accctcgtca accccagccc ctggcaacac cgactctatg ttcatcatcc tcggctgctt   1560
ctgtggattc attttaatcg ggttaatttt gtgtatttct ctggccctca gaaggagagt   1620
ccaggaaaca aagtttgggg gagcattctc tgaggaggat tcccaactgg tcgtaaatta   1680
tagagcgaag aagtccttct gccggcgagc catcgagctt accttgcaga gcctgggagt   1740
gagcgaggag ctgcagaata agctggaaga tgttgtgatt gacagaaacc ttctggttct   1800
cggcaaagtt ctgggtgaag gagagtttgg gtctgtaatg gaaggaaatt tgaagcaaga   1860
agatgggact tctcagaagg tggcagtgaa gaccatgaag ttggacaact tttctcaacg   1920
ggagatcgag gagtttctca gcgaagcagc atgcatgaaa gacttcaacc acccaaatgt   1980
catccgactt ctaggcgtgt gtatagaact gagctctcaa ggcatcccga agcccatggt   2040
gattttaccc ttcatgaaat acggagacct ccacaccttc ctgttatatt cccgattaaa   2100
cacaggaccc aagtacattc acctgcagac actactgaag ttcatgatgg acattgccca   2160
gggaatggag tatctgagca acaggaattt tcttcatagg gatttggcag ctcgaaactg   2220
catgttgcgg gatgacatga ctgtctgcgt ggcagacttt ggcctctcaa agaagattta   2280
cagtggtgat tattaccgcc aaggccgcat tgccaaaatg cctgtgaagt ggatcgccat   2340
cgagagcctg gcggaccgag tctacacaag caaaagtgac gtgtgggctt ttggcgtgac   2400
catgtgggaa ataacaacac ggggaatgac tccctatccc ggagttcaga accatgagat   2460
gtacgactac cttctccacg gccacaggct gaagcagcct gaggactgct tggatgaact   2520
gtatgacatc atgtactctt gctggagtgc tgatcccttg gatcgaccca ccttctctgt   2580
gttgaggctg cagctggaaa agctctccga gagtttgcct gatgcgcagg acaaagaatc   2640
catcatctac atcaataccc agttgctaga gagctgcgag ggcatagcca atgggccctc   2700
actcacgggg ctagacatga acattgaccc tgactccatc attgcctctt gcacaccagg   2760
cgctgccgtc agcgtggtca cggcagaagt tcacgagaac aaccttcgtg aggaaagata   2820
catcttgaat gggggcaatg aggaatggga agatgtgtcc tccactcctt ttgctgcagt   2880
cacacctgaa aaggatggtg tcttaccgga ggacagactc accaaaaatg gcgtctcctg   2940
gtctcaccat agtacactac ccttggggag cccatcacca gatgaacttt tatttgtaga   3000
tgactccttg gaagactctg aagttctgat gtgaagccag ctgagaggag gcatgagaga   3060
accaagcaaa tacagcttcc tgggatctgg tggtcttaga tactttgtta ttgctctgat   3120
aaaacatcat gaccaaggca atcttcaaga gaaagtgttt aactaggttt actgtttcag   3180
```

```
ggggttagag tctatgattg cagaaggaag ttatgatggc aggaacagct gagtgcttat   3240

atctttaaga gcaagcagga gacagagagc actctgggaa atggcaccta tcttttgaaa   3300

cctcaaagcc tgctcccagt gacaaaagtc cttcaacagg ccatacctcc taatccttcc   3360

caaacaattc caccaactgg agaccaaaca ttcaaatgta tgcgcgtatt ggggccattc   3420

ttaagcaaac cactacactg gttatacctg aggttttggt acttgttttc cttaccaagt   3480

agagttcatg gccggacagc accaggtgaa agctgtcaag tcaggtttgc aaatacataa   3540

ccaaggtctt gagagctcgt gccg                                          3564
```

<210> SEQ ID NO 36
<211> LENGTH: 1372
<212> TYPE: DNA
<213> ORGANISM: Homo sapiens

<400> SEQUENCE: 36

```
atgctagcaa ttattgtacc cacaattata cttatgccag tgacacgata ttctaaaaat     60

tctaaaattt gaattcacac aactatgcac tgcttactaa ttagtttcat caaattattc    120

ctcttaagcc aatttagtaa aaataaccta aacttttcat tagttttttt ctccaactca    180

ctatcagcct ccatttcatt atactaacaa attgattact tcccctaata attatagcaa    240

gttaacatca tctctccaaa gaatcatata tatgaaaaag ctacatattt caatattaat    300

ctttctacat ttattcttaa tcataacatt tactgccaca gaactaaatc tattttacat    360

tctctttgaa gcaacactaa ttccaactct aattattatt ctctgataag gaaacaaaag    420

agaatgatta aatccagggc tctatttcct gttctacaca ctaattggtt ttttacctca    480

actcgtatca ttaattttta tccaaaactc cacatactca ttacactttt taataacctg    540

ttactgtgtt caaactcagc tcttgacata atagtctttt atgattagca tgcattatag    600

catttatggt caaaataccc ctttatagtt tctatctctg actaacaaag tacacacaga    660

aactccaatt gctgaatcca cagtttttgc agccataaaa ttagcaggct ttaatataat    720

acgaattact ataattccaa acccactaat ggaatatata gcttatccat ttcatatagt    780

atccccgtga tgaataatta taacacactc tatttgttta caccaaatag acttaaaatc    840

acttaatcac ttatcacata ttcatccata aatcatatag cactaacatt tatagccatt    900

ttcatccaag ctcaacgaat ttttatagga gccataaccc taataattgc ccatgccctc    960

acctcatcca tactattctt catcacaaac tcaaattatg aatgaattta tagctgaaat   1020

atgctcttca ttcaaggact gcagacatta ctccctttaa taacaacatg atgagtatta   1080

gctagcctaa ccaatctagc cctaccacca accatcaacc taatcagaga actatgtgta   1140

gtcacagcac cattttcatg atttaatttt accattatta ttaataggac ttaatatatt   1200

aattatagcc taatattccc tctgcatatt aattacaatg caacaaggaa aatttaccaa   1260

tcacattaat aaattagcca tcactcacat tagaaaatgc tttatacatc tacctctgct   1320

actcctatca cttaatgaca aaattattct aggacctaca tactgttttt aa           1372
```

<210> SEQ ID NO 37
<211> LENGTH: 312
<212> TYPE: DNA
<213> ORGANISM: Homo sapiens

<400> SEQUENCE: 37

```
aattatctca tttgtttttt ctgacaacat aataagaaaa agaaaaacat ccattcatga     60
```

```
gagttcaggg atacgtgaaa atgaagcaaa tgaggaaaga cccattcaca ttcctccaaa    120

agatctgtgg ctcactggaa tcatgttact ggctcctggt agtccctgac tttacctgtt    180

tgttccagga acttgcttta tggccatttg ttctaatgat cagtttggac aaccaacctt    240

tattcctcca cctcagacaa tattcaacat cctgtaatca tcatagcgac aaactgttaa    300

aacaacaaca gc                                                        312


<210> SEQ ID NO 38
<211> LENGTH: 2784
<212> TYPE: DNA
<213> ORGANISM: Homo sapiens

<400> SEQUENCE: 38

gtgagccgag attgcacctc tgcactccaa cctgggcgac gagagtgtaa ctctgtctca     60

aaaaagaaaa tattctcttg gtaacactat tggaatagga acattcactg atggaggaaa    120

tgcaaaactg tataatctct gttatagggg aatttggcaa ttttacattt aaatttgcct    180

tgtgacccag caatcctgct atattattcc tttcatattg ctataaaaaa atctgaggct    240

gggtaattta taaagaaagg aggtattttt tttcatggtt cttcaggctg tatacaagca    300

gggctgttag catctgctca gcttctgatg aggcccagga agcttttggt cttggtggaa    360

gagaagagga gccagcatat tacatgacga gaggaagcaa gagagatacc aggctctttt    420

aagcaaccag ttctcatgtg aacgcattgc tactgagaaa gtgccaaacc attcacgagg    480

gatccactac ctagacccaa acacctcccc ctaggccccg tctccaacag cggggatcat    540

atttcaacat gagacttcga ggagacaaat atccaaacca tatcgcccac gtttaggaat    600

gtctctccat ggtagatgat ttgcaaatag acggtggtat acccattcca tggaagcagg    660

gaaatatgtt tgcacgtctt tggttagtcc tcttcttttc tactgacagt gggcttgtcc    720

atgtgtcctg catgatcaaa atgacaatag caaacttgat ggccacagaa gattgaaaag    780

tgcttgggca ttgagcttgc tctctcttga agtgcttgga gccctgagac tgccatgaga    840

ccacataaat gatcactagc tagcctgctg gaggatgaga ggtcacttga gaaaccttgg    900

ctcacagcct gcttacacca gacacatgga tgagtctgtc ttagactatc cagctccagc    960

tgagttgcca gctgacttca gtcacatgag tgagaacaac agaaggacag cactgagctc   1020

tgccaaaatt gctgacctac agaatcttga gctaatgaat gattgtagct ttatgccatt   1080

aagttctgag gcagtgtgct atacatagca aaagctaact gatacaaaac taaagataca   1140

atggcacaaa catgaaaaga catgttcacc gaagcattgc ctataatagt taaagactgg   1200

aaacgactca gatgtccacc aactcaggag tggttgaacc tactacagtg cattcacccc   1260

gtggaatact aagcagctcc aacaggggta ggaaatttgt atactttcat aaaatgatct   1320

ttaggatata ttgttaagtg aaaaaaacaa ggtgtagaat agttaataga gtatgctacc   1380

tcttatttaa taaagggaga atataaatat gtattttgct tttatttaga aaatgaaaga   1440

ataagaaacc actaaaatga ttttttagaa gaaagcaagg ggacacagat ggaagttaga   1500

tttctctaaa tttactttgt tttgtagcta gaactttaga accatgtcaa tgttttacac   1560

acgtcacact tataatcaag ataaaaaata cttatacagt gatgtgtcac ttaatgacag   1620

ggatatattc tgagaaatgg tgccgttagg cacttttgtc cctgtgccaa catcatagaa   1680

tatacctact gcacacctag gctatatgat gtagtctatt gctcctaagc tacaaacctg   1740

tatagcatgt tactgtactg aatactgtag gcaattgtaa cagaatggta aacatttgtg   1800

tatctaaaca tagaaaaggt acagtaaaaa cacagtataa aagtcaaaaa atggtacact   1860
```

-continued

```
tgcaagggca cttaccagga atggagctta gaggttggaa gttgctctgt atgagtcagt   1920

gagtgagtgg tgagtgaatg tggaggccta ggaaattatt ctacactact gtagaattta   1980

tgaacatttg ggctacacta aatttataaa aaacattttc ttcttcaata atgagttagc   2040

tcactgtaac ttacttttta aactttttaa atgtttttta agtttttaac tcttgtaata   2100

acacttagct taaaacacac attgtacagc tgtacaaaaa tattttcttt atgtcattct   2160

ataagctttt taaaatattt tcaaatgtat tttttttttt aaagcttaaa aaaaacatgt   2220

aagacaccca catattagcc tagacctaca cagggtcagg atcattaata tcagtgtctt   2280

ccatctccac atcttgtccc actggaaggt cttgaggggc aataacatgt atggagctgt   2340

catttcctat gataacaatg ccttctggaa ggcttcctga aggacctgcc tgaggctctt   2400

tttgaggcag tgtcactctt ttcagaaata tgtccatggt ggtttactca atttgcttct   2460

tttttattca tagatttgca tatgtaatgc attgcgctat accattaaga cagctatgat   2520

gtcactgcag ttacagtgtc actaggtgat agaaattgtc cagctccatt acaaccttat   2580

ggaaccactg gtgcatacgt ggttcattgt ggtccattgt tgactgaaac aatgttatga   2640

ggtgcgtaac tatatatcca aagcaaaagc taaatgaaat aaatgaaact aattgtgttg   2700

gtgtcctaaa cacacagagg agaattactt caagtatttt taaaacacag tcacttgtct   2760

atgcattttt agtggatatg ccct                                          2784
```

HER2-REGULATED RNA AS A DIAGNOSTIC AND THERAPEUTIC TARGETS IN HER2+ BREAST CANCER

RELATED APPLICATION

This application claims priority from U.S. Provisional Application No. 62/128,784, filed Mar. 5, 2015, the subject matter of which is incorporated herein by reference in its entirety.

BACKGROUND

Breast cancer is the leading cause of cancer among women, with over 200,000 new cases diagnosed in the United States each year. Breast cancer is composed of several subtypes, with 20-30% of early-stage breast cancers characterized by the amplification of the human epidermal growth factor receptor 2 (HER2) gene, also known as HER2/neu and ERBB2. In normal cells, HER2 signaling is initiated through heterodimerization of HER2 with other ERBB family members in response to extracellular signals. Dimerization and subsequent autophosphorylation through the tyrosine kinase domain initiates a signaling cascade that ultimately leads to changes in gene expression patterns that regulate cell proliferation and growth. However, how HER2 gene amplification in breast cancer leads to uncontrolled cell proliferation is yet to be fully understood.

The human genome encodes, in addition to mRNAs and small non-coding RNAs, over 8,300 long intervening non-coding RNAs (lincRNAs). Recent studies have demonstrated important roles for lincRNAs in embryonic and organ development in vivo. Additionally, gene expression studies revealed that each lincRNA can regulate numerous mRNA genes, mostly at genomic sites far away from a lincRNA site of transcription, and thus, lincRNAs are thought to exert their effects in trans. The impact of lincRNAs on gene expression patterns has implicated lincRNAs in a wide range of biological functions including dosage compensation, genomic imprinting, alternative splicing, nuclear organization, and regulation of mRNA translation. Intriguingly, lincRNAs utilize various mechanisms to exert their effects in the cell. These mechanisms include acting as scaffolds and guides for chromatin-modifying complexes to specific regions of the genome, serving as decoys that regulate transcription factors binding to specific DNA sequences, and as microRNA "sponges" that regulate miRNA:mRNA interactions.

Recently, there has been growing interest in unraveling the roles of lincRNAs in human disease with the hope that these novel transcripts can be used as diagnostic biomarkers and/or therapeutic targets. In addition, there is a significant interest in studying the functional roles of lincRNAs in cancer since numerous lincRNAs have been shown to be dysregulated across multiple cancer types. These studies have also shown that the expression of some lincRNAs correlates with clinical parameters, such as overall patient prognosis and metastasis. For example, the lincRNA HOTAIR is highly upregulated in breast cancer, hepatocellular carcinoma, and colorectal cancers. Additionally, in vitro and in vivo functional studies have implicated HOTAIR in promoting cancer metastasis. The lincRNA linc-p21 is transcriptionally activated by the tumor suppressor p53 and subsequently represses a subset of p53 gene targets in trans through binding of hnRNP-K, thereby facilitating the p53 response in cells. A final example focuses on the X inactive specific transcript (Xist), which has been known for decades to be the key transcript for X chromosome inactivation (Xi) in mammalian females. Recently, it has been shown that genetic deletion of Xist in hematopoietic stem cells results in a variety of hematological cancers and premature death in mice. Taken together, these selected examples, as well as many others, demonstrate important roles of lincRNAs in tumorigenesis and metastasis, and their potential utilization as biomarkers and/or therapeutic targets.

SUMMARY

Embodiments described herein relate to RNAs (e.g., lincRNAs) associated with HER2 signaling (HER2-associated RNA) in HER2 positive human breast cancer cells, methods and compositions of modulating the levels of HER2-associated RNA in breast cancer cells of the subject to treat breast cancer cells or a subject in need thereof, and/or methods of measuring the expression profile of HER2-associated RNA to determine whether the subject has breast cancer or an increased risk of breast cancer and/or the efficacy of a therapeutic regimen agent.

In some embodiments, breast cancer in a subject can be treated by administering an agent to breast cancer cells of the subject that is effective to modulate the level of HER2-associated RNA in the breast cancer cells. In other embodiments, the HER2-associated RNA can be HER2-associated long non-coding RNA.

In some embodiments, the agent administered to the breast cancer cells to treat breast cancer in the subject can be effective to decrease the level of HER2-associated RNA, which is over expressed in the breast cancer cells compared to normal cells. An agent effective to decrease the level of HER2-associated RNA, which is over expressed in the breast cancer cells, can include an RNA inhibitor of the HER2-associated RNA, such as siRNA, miRNA, stRNA, snRNA, shRNA, and antisense nucleic acids to the HER2-associated RNA.

In one example, the HER2-associated RNA that is over expressed or upregulated, can include at least one of RRM2, TOP2A, CCNE2, EXO1, ANLN, DLGAP5, CDKN3, NUSAP1, CCNB2, FAM11B, HISH1H2BG, BUB1B, CDC6, MAL2, SQLE, KIF23, CCNB1, PRC1, CKS2, GINS1, HIST1H2BO, ECT2, ATAD2, GGCT, HISST2H2BE, NME1, GALNT7, MCM4, DHCR24, RAD21, TMEM97, HMGCS1, MSM01, LMNB2, or linc-STRAD6-2.

In another example, the HER2 associated RNA that is over expressed can include at least one of MAL2, ATAD2, GGCT, GALNT7, TMEM97, HMGCS1, MSM01.

In yet another example, the HER2 associated RNA that is over expressed can include linc-STRAD6-2.

In other embodiments, the agent administered to the breast cancer cells to treat breast cancer in the subject can be effective to increase the level of HER2-associated RNA that is under expressed or downregulated in the breast cancer cells compared to normal cells. The agent can include, for example, a nucleic acid encoding the under expressed HER2-associated RNA that is administered to the breast cancer cells using, for example, an expression vector.

In one example, the HER2-associated RNA that is under expressed or down regulated in the breast cancer cells can include at least one of MERTK, linc-GJA1-2 or linc-SLC39A10-10.

In another example, the HER2-associated RNA that is under expressed or down regulated in the breast cancer cells can include at least one of linc-GJA1-2 or linc-SLC39A10-10.

Other embodiments described herein relate to a method of analyzing bodily sample, such as bodily tissue (e.g., breast tissue) or bodily fluid (e.g., blood, plasma, or serum) from a subject having or suspected of having breast cancer. The method includes obtaining an expression profile from a sample obtained from the subject, wherein the expression profile comprises the level of at least one HER2-associated RNA selected from the group consisting of RRM2, TOP2A, CCNE2, EXO1, ANLN, DLGAP5, CDKN3, NUSAP1, CCNB2, FAM11B, HISH1H2BG, BUB1B, CDC6, MAL2, SQLE, KIF23, CCNB1, PRC1, CKS2, GINS1, HIST1H2BO, ECT2, ATAD2, GGCT, HISST2H2BE, NME1, GALNT7, MCM4, DHCR24, RAD21, TMEM97, HMGCS1, MSM01, LMNB2, MERTK, linc-STRAD6-2, linc-GJA1-2, Linc-SLC39A10-10, and combinations thereof. The expression profile from the sample is then compared to an expression profile of a control or standard. A decrease in the expression of the at least one HER2-associated RNA selected from the group consisting of MERTK, linc-GJA1-2, linc-SLC39A10-10, and combinations thereof and/or increase in the expression of the at least one HER2-associated RNA selected from the group consisting of RRM2, TOP2A, CCNE2, EXO1, ANLN, DLGAP5, CDKN3, NUSAP1, CCNB2, FAM11B, HISH1H2BG, BUB1B, CDC6, MAL2, SQLE, KIF23, CCNB1, PRC1, CKS2, GINS1, HIST1H2BO, ECT2, ATAD2, GGCT, HISST2H2BE, NME1, GALNT7, MCM4, DHCR24, RAD21, TMEM97, HMGCS1, MSM01, LMNB2, linc-STRAD6-2, and combinations thereof is indicative of the subject having breast cancer or an increased risk of breast cancer. In some embodiments, the bodily sample is a bodily fluid and an increase in the expression of a protein of the at least one HER2-associated RNA selected from the group consisting of MAL2, ATAD2, GGCT, GALNT7, TMEM97, HMGCS1, MSM01 and combinations thereof is indicative of the subject having breast cancer or an increased risk of breast cancer.

Still other embodiments relate to a method of predicting whether a subject has breast cancer or an increased risk of breast cancer. The method includes obtaining an expression profile from a bodily sample obtained from the subject, wherein the expression profile comprises the level of at least one HER2-associated RNA selected from the group consisting of RRM2, TOP2A, CCNE2, EXO1, ANLN, DLGAP5, CDKN3, NUSAP1, CCNB2, FAM11B, HISH1H2BG, BUB1B, CDC6, MAL2, SQLE, KIF23, CCNB1, PRC1, CKS2, GINS1, HIST1H2BO, ECT2, ATAD2, GGCT, HISST2H2BE, NME1, GALNT7, MCM4, DHCR24, RAD21, TMEM97, HMGCS1, MSM01, LMNB2, MERTK, linc-STRAD6-2, linc-GJA1-2, linc-SLC39A10-10, and combinations thereof. The expression profile from the sample is then compared to an expression profile of a control or standard and whether the subject has breast cancer or an increased risk of breast cancer is predicted based on (i) deviation of the expression profile of the sample from a control or standard derived from a healthy individual or population of healthy individuals, or (ii) the similarity of expression profiles of the sample and a control or standard derived from an individual or population of individuals who have or have had the breast cancer. In some embodiments, a decrease in the expression of the at least one HER2-associated RNA from the group consisting of MERTK, linc-GJA1-2, linc-SLC39A10-10, and combinations thereof and/or an increase in the expression of the at least one HER2-associated RNA selected from the group consisting of RRM2, TOP2A, CCNE2, EXO1, ANLN, DLGAP5, CDKN3, NUSAP1, CCNB2, FAM11B, HISH1H2BG, BUB1B, CDC6, MAL2, SQLE, KIF23, CCNB1, PRC1, CKS2, GINS1, HIST1H2BO, ECT2, ATAD2, GGCT, HISST2H2BE, NME1, GALNT7, MCM4, DHCR24, RAD21, TMEM97, HMGCS1, MSM01, LMNB2, linc-STRAD6-2, and combinations thereof is indicative of the subject having cancer or an increased risk of breast cancer. In some embodiments, the bodily sample is a bodily fluid and an increase in the expression of a protein of the at least one HER2-associated RNA selected from the group consisting of MAL2, ATAD2, GGCT, GALNT7, TMEM97, HMGCS1, MSM01 and combinations thereof is indicative of the subject having breast cancer or an increased risk of breast cancer.

Other embodiments relate to a method of monitoring a subject's response to a treatment regimen for cancer. The method includes administering a therapeutic regimen to the subject. An expression profile from a bodily sample is obtained from the subject, wherein the expression profile comprises the level of at least one HER2-associated RNA selected from the group consisting of RRM2, TOP2A, CCNE2, EXO1, ANLN, DLGAP5, CDKN3, NUSAP1, CCNB2, FAM11B, HISH1H2BG, BUB1B, CDC6, MAL2, SQLE, KIF23, CCNB1, PRC1, CKS2, GINS1, HIST1H2BO, ECT2, ATAD2, GGCT, HISST2H2BE, NME1, GALNT7, MCM4, DHCR24, RAD21, TMEM97, HMGCS1, MSM01, LMNB2, MERTK, linc-STRAD6-2, linc-GJA1-2, linc-SLC39A10-10, and combinations thereof. The expression profile from the sample is compared to an expression profile of a control or standard. An increase in the expression of the at least one HER2-associated RNA from the group consisting of MERTK, linc-GJA1-2, Linc-SLC39A10-10, and combinations thereof and/or decrease in the expression of the at least one HER2-associated RNA selected from the group consisting of RRM2, TOP2A, CCNE2, EXO1, ANLN, DLGAP5, CDKN3, NUSAP1, CCNB2, FAM11B, HISH1H2BG, BUB1B, CDC6, MAL2, SQLE, KIF23, CCNB1, PRC1, CKS2, GINS1, HIST1H2BO, ECT2, ATAD2, GGCT, HISST2H2BE, NME1, GALNT7, MCM4, DHCR24, RAD21, TMEM97, HMGCS1, MSM01, LMNB2, linc-STRAD6-2, and combinations thereof is indicative of an increased efficacy of the therapeutic regimen.

In some embodiments, the bodily sample is a bodily fluid and a decrease in the expression of a protein of the at least one HER2-associated RNA selected from the group consisting of MAL2, ATAD2, GGCT, GALNT7, TMEM97, HMGCS1, MSM01 and combinations thereof is indicative of an increased efficacy of the therapeutic regimens.

BRIEF DESCRIPTION OF THE DRAWINGS

FIGS. 1(A-C) illustrate inhibition of HER2 in vivo by trastuzumab results in significant changes in the expression of mRNAs and lincRNAs in HER2+ breast cancer patients. Differentially expressed mRNAs (A) and lincRNAs (B) in all 22 RNA-seq samples (11 pre-vs 11 post-trastuzumab) are represented by heatmaps; (C) Over enrichment analysis of differentially expressed mRNAs pre-vs post-trastuzumab reveals several key pathways affected in vivo when HER2 signaling is inhibited. Number of genes and p-values are shown for each pathway.

FIGS. 2(A-F) illustrate HER2 affects the expression of mRNAs and lincRNAs in BT474 cells. (A) Real time qPCR analysis of HER2 mRNA levels in BT474 cells transfected with either control siRNAs or HER2 siRNAs (15 nM final concentration. (B) Western blot analysis of HER2 protein levels in BT474 cells transfected with control siRNAs vs cells transfected with HER2 siRNAs at 48 hours post transfections. (C-D) Gene expression analysis by RNA-seq led to the identification of differentially expressed mRNAs and lincRNAs in BT474 cells treated with either control or HER2 siRNAs. Heatmaps of differentially expressed mRNAs and lincRNAs between BT474 cells transfected with control siRNAs vs HER2 siRNAs are shown. (E-F) Validation of RNA-seq data by RT-qPCR of eight mRNA genes and five lincRNAs in cells transfected with control siRNAs vs HER2 siRNAs.

FIGS. 3(A-B) illustrate validation of HER2-regulated lincRNAs in BT474 cells using a second independent siRNA. (A) We designed and confirmed the knockdown of HER2 protein using a second independent siRNA (distinct from first siRNA used for knock down experiments and subsequent RNA-seq analysis). Western blot analysis of HER2 protein levels in BT474 cells treated with siRNA #2 alone or in combination with first siRNA (siRNA pool) demonstrate the effectiveness of this second siRNA in knocking down HER2 protein in comparison to negative control siRNAs. (B) We examined the expression of the same 5 lincRNAs in FIG. 2F post HER2 knock down in BT474 cells with a second independent siRNA by qPCR analysis. We found that HER2 knock down with a second independent siRNA also affects the expression of some of these lincRNAs.

FIGS. 4(A-C) illustrate identification of commonly affected mRNAs and lincRNAs post HER2 inhibition in tumors in vivo and post HER2 knockdown in cell culture by siRNAs. To identify mRNAs and lincRNAs that are likely critical targets of HER2, we intersected differentially expressed mRNAs and lincRNAs that we have identified in pre-vs post-HER2 inhibition by trastuzumab in tumors in vivo and differentially expressed mRNAs and lincRNAs in BT474 cells treated with either control or HER2 siRNAs. We identified 44 mRNAs (A) and 3 lincRNAs (B) to overlap between the two data sets. (C) Of the 44 common mRNAs identified in our aforementioned analysis, several genes are known components of the E2F transcription factor network and PLK1 signaling pathway.

FIGS. 7(A-C) illustrate validation of lincRNAs expression in 12 tumors vs matched normal tissue (TCGA cohort). We have identified three lincRNAs that are affected by both HER2 inhibition and HER2 knockdown in tumors and BT474 cells, respectively. To determine the potential role of these lincRNAs in HER2+ cancer, we examined their expression in HER2+ tumors and matched normal tissues from TCGA RNA-seq data sets. The fold change of (A) linc-STARD6-2, (B) linc-GJA1-2, and (C) linc-SLC39A10-10 was graphed for each TCGA HER2+ patient sample (Tumor/Normal). Linc-STARD6-2 shows up-regulation in 8/12 TCGA Tumor/Normal samples. linc-GJA1-2 and Linc-SLC39A10-10 show down-regulation in 10/11 and 9/12 tumor samples compared to matched normal controls, respectively.

DETAILED DESCRIPTION

Figure 5C:
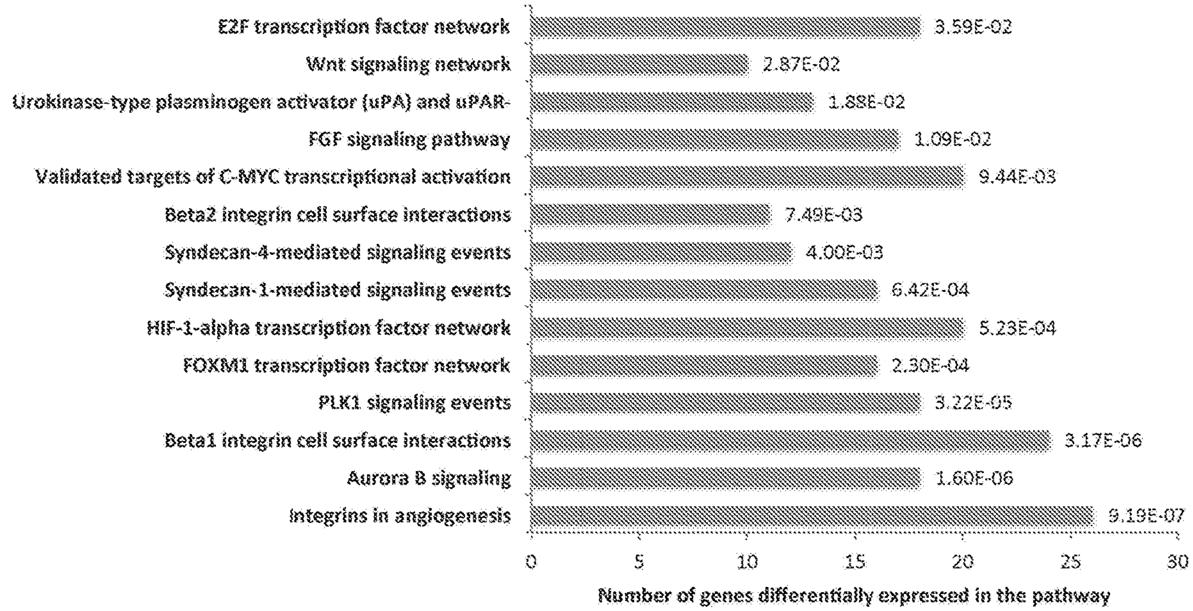
FIGS. 5(A-C) illustrate dysregulation of mRNAs and lincRNAs in HER2+ tumors. We utilized public RNA-seq of 12 HER2+ tumors and 12 matched normal breast tissues to identify differentially expressed mRNAs and lincRNAs. Differentially expressed mRNAs (A) and lincRNAs (B) in HER2+ breast cancer patient tumors vs. adjacent matched normal tissue obtained from The Cancer Genome Atlas (TCGA) are represented by heatmaps. In total, 2,521 mRNAs and 283 lincRNAs were identified as differentially expressed. (C) Cancer-associated pathways are affected when HER2 is amplified. Over enrichment analysis of differentially expressed mRNAs between tumors and matched control samples from 12 HER2+ breast cancer patients (TCGA cohort) reveals several biological pathways that become altered due to increased HER2 expression in these tumors. Number of genes and p-values associated with each pathway are also shown.

For convenience, certain terms employed in the entire application (including the specification, examples, and appended claims) are collected here. Unless defined otherwise, all technical and scientific terms used herein have the same meaning as commonly understood by one of ordinary skill in the art to which this invention belongs.

It is to be understood that this invention is not limited to the particular methodology, protocols, cell lines, plant species or genera, constructs, and reagents described as such. It is also to be understood that the terminology used herein is for the purpose of describing particular embodiments only, and is not intended to limit the scope of the present invention which will be limited only by the appended claims.

The term "pharmaceutically acceptable carrier" refers to any of the standard pharmaceutical carriers, such as a phosphate buffered saline solution, water, emulsions such as an oil/water or water/oil emulsion, and various types of wetting agents. The term also encompasses any of the agents approved by a regulatory agency of the US Federal government or listed in the US Pharmacopeia for use in animals, including humans.

The term "subject" refers to any organism or animal to whom treatment or prophylaxis treatment is desired. Such animals include mammals, preferably a human.

The term "mammal" or "mammalian" are used interchangeably herein, and encompass their normal meaning. While the methods and compositions described herein are most desirably intended for efficacy in humans, they may also be employed in domestic mammals such as canines, felines, and equines, as well as in mammals of particular interest, e.g., zoo animals, farmstock, transgenic animals, rodents and the like.

The terms "gene silencing" or "gene silenced" in reference to an activity of a RNAi molecule, for example a siRNA or miRNA refers to a decrease in the mRNA level in a cell for a heterologous target gene by at least about 5%, about 10%, about 20%, about 30%, about 40%, about 50%, about 60%, about 70%, about 80%, about 90%, about 95%, about 99%, about 100% of the mRNA level found in the cell without the presence of the miRNA or RNA interference molecule. In one embodiment, the mRNA levels are decreased by at least about 70%, about 80%, about 90%, about 95%, about 99%, about 100%. As used herein, the "reduced" or "gene silencing" refers to lower, preferably significantly lower, more preferably the expression of the nucleotide sequence is not detectable.

The term "double-stranded RNA" molecule, "RNAi molecule", or "dsRNA" molecule refers to a sense RNA fragment of a nucleotide sequence and an antisense RNA fragment of the nucleotide sequence, which both comprise nucleotide sequences complementary to one another, thereby allowing the sense and antisense RNA fragments to pair and form a double-stranded RNA molecule. In some embodiments, the terms refer to a double-stranded RNA molecule capable, when expressed, is at least partially reducing the level of the mRNA of the heterologous target gene. In particular, the RNAi molecule is complementary to a synthetic RNAi target sequence located in a non-coding region of the heterologous target gene.

The terms "RNA interference", "RNAi", and "dsRNAi" are used interchangeably herein and refer to nucleic acid molecules capable of gene silencing.

The term "RNAi" refers to any type of interfering RNA, including siRNAi, shRNAi, stRNAi, endogenous microRNA and artificial microRNA. For instance, it includes sequences previously identified as siRNA, regardless of the mechanism of down-stream processing of the RNA. The term "siRNA" also refers to a nucleic acid that forms a double stranded RNA, which double stranded RNA has the ability to reduce or inhibit expression of a gene or target gene when the siRNA is present or expressed in the same cell as the target gene. The double stranded RNA siRNA can be formed by the complementary strands. In one embodiment, a siRNA refers to a nucleic acid that can form a double stranded siRNA. The sequence of the siRNA can correspond to the full length target gene, or a subsequence thereof. Typically, the siRNA is at least about 10-50 nucleotides in length (e.g., each complementary sequence of the double stranded siRNA is about 10-22 nucleotides in length, and the double stranded siRNA is about 10-22 base pairs in length, preferably about 19-22 base nucleotides, preferably about 17-19 nucleotides in length, e.g., 10, 11, 12, 13, 14, 15, 16, 17, 18, 19, 20, 21, or 22 nucleotides in length).

The terms "shRNA" or "small hairpin RNA" (also called stem loop) is a type of siRNA. In one embodiment, these shRNAs are composed of a short, e.g., about 10 to about 25 nucleotide, antisense strand, followed by a nucleotide loop of about 5 to about 9 nucleotides, and the analogous sense strand. Alternatively, the sense strand can precede the nucleotide loop structure and the antisense strand can follow.

The term a "stem-loop structure" refers to a nucleic acid having a secondary structure that includes a region of nucleotides, which are known or predicted to form a double strand (stem portion) that is linked on one side by a region of predominantly single-stranded nucleotides (loop portion). The terms "hairpin" and "fold-back" structures are also used herein to refer to stem-loop structures. Such structures are well known in the art and the term is used consistently with its known meaning in the art. The actual primary sequence of nucleotides within the stem-loop structure is not critical to the practice of the invention as long as the secondary structure is present. As is known in the art, the secondary structure does not require exact base-pairing. Thus, the stem may include one or more base mismatches. Alternatively, the base-pairing may be exact, i.e., not include any mismatches. In some instances the precursor microRNA molecule may include more than one stem-loop structure. The multiple stem-loop structures may be linked to one another through a linker, such as, for example, a nucleic acid linker or by a microRNA flanking sequence or other molecule or some combination thereof. The actual primary sequence of nucleotides within the stem-loop structure is not critical as long as the secondary structure is present. As is known in the art, the secondary structure does not require exact base-pairing. Thus, the stem may include one or more base mismatches. Alternatively, the base pairing may not include any mismatches.

The term "hairpin RNA" refers to any self-annealing double stranded RNA molecule. In its simplest representation, a hairpin RNA consists of a double stranded stem made up by the annealing RNA strands, connected by a single stranded RNA loop, and is also referred to as a "pan-handle RNA". However, the term "hairpin RNA" is also intended to encompass more complicated secondary RNA structures comprising self-annealing double stranded RNA sequences, but also internal bulges and loops. The specific secondary structure adapted will be determined by the free energy of the RNA molecule, and can be predicted for different situations using appropriate software such as FOLDRNA (Zuker and Stiegler (1981) Nucleic Acids Res 9(1):133-48; Zuker, M. (1989) Methods Enzymol. 180, 262-288).

The term "agent" refers to any entity, which is normally absent or not present at the levels being administered, in the cell. An agent may be selected from a group comprising; chemicals; small molecules; nucleic acid sequences; nucleic acid analogues; proteins; peptides; aptamers; antibodies; or fragments thereof. A nucleic acid sequence may be RNA or DNA, and may be single or double stranded, and can be selected from a group comprising; nucleic acid encoding a protein of interest, oligonucleotides, nucleic acid analogues, for example peptide-nucleic acid (PNA), pseudo-complementary PNA (pc-PNA), locked nucleic acid (LNA), etc. Such nucleic acid sequences include, for example, but not limited to, nucleic acid sequence encoding proteins, for example that act as transcriptional repressors, antisense molecules, ribozymes, small inhibitory nucleic acid sequences, for example but not limited to RNAi, shRNAi, siRNA, micro RNAi (mRNAi), antisense oligonucleotides etc. A protein and/or peptide or fragment thereof can be any protein of interest, for example, but not limited to; mutated proteins; therapeutic proteins; truncated proteins, wherein the protein is normally absent or expressed at lower levels in the cell. Proteins can also be selected from a group comprising; mutated proteins, genetically engineered proteins, peptides, synthetic peptides, recombinant proteins, chimeric proteins, antibodies, midibodies, tribodies, humanized proteins, humanized antibodies, chimeric antibodies, modified proteins and fragments thereof. The agent may be applied to the media, where it contacts the cell and induces its effects. Alternatively, the agent may be intracellular within the cell as a result of introduction of the nucleic acid sequence into the cell and its transcription resulting in the production of the nucleic acid and/or protein environmental stimuli within the cell. In some embodiments, the agent is any chemical, entity or moiety, including without limitation synthetic and naturally-occurring non-proteinaceous entities. In certain embodiments the agent is a small molecule having a chemical moiety. For example, chemical moieties included unsubstituted or substituted alkyl, aromatic, or heterocyclyl moieties including macrolides, leptomycins and related natural products or analogues thereof. Agents can be known to have a desired activity and/or property, or can be selected from a library of diverse compounds.

The terms "a reduction" of the level of an RNA, mRNA, rRNA, tRNA, or lincRNA includes a decrease in the level of the RNA, mRNA, rRNA, tRNA, or lincRNA in the cell or organism. "At least a partial reduction" of the level of the RNA, mRNA, rRNA, tRNA or lincRNA means that the level is reduced at least about 10%, at least about 25%, at least 50% or more relative to a cell or organism in which the level of RNA, mRNA, rRNA, tRNA or lincRNA is not reduced by some means. "A substantial reduction" of the level of RNA, mRNA, rRNA, tRNA or lincRNA means that the level is reduced at least about 75%, at least about 85% or more. The reduction can be determined by methods with which the skilled worker is familiar Thus, the reduction can be determined for example by reverse transcription (quantitative RT-PCR), ELISA (enzyme-linked immunosorbent assay), Western blotting, radioimmunoassay (RIA) or other immunoassays and fluorescence-activated cell analysis (FACS).

In its broadest sense, the term "substantially complementary", when used herein with respect to a nucleotide sequence in relation to a reference or target nucleotide sequence, means a nucleotide sequence having a percentage of identity between the substantially complementary nucleotide sequence and the exact complementary sequence of said reference or target nucleotide sequence of at least 60%, at least 70%, at least 80% or 85%, at least 90%, at least 93%, at least 95% or 96%, at least 97% or 98%, at least 99% or 100% (the later being equivalent to the term "identical" in this context). For example, identity is assessed over a length of at least 10 nucleotides, or at least 11, 12, 13, 14, 15, 16, 17, 18, 19, 20, 21, 22 or up to 50 nucleotides of the entire length of the nucleic acid sequence to said reference sequence (if not specified otherwise below). Sequence comparisons are carried out using default GAP analysis with the University of Wisconsin GCG, SEQWEB application of GAP, based on the algorithm of Needleman and Wunsch (Needleman and Wunsch (1970) J MoI. Biol. 48: 443-453; as defined above). A nucleotide sequence "substantially complementary" to a reference nucleotide sequence hybridizes to the reference nucleotide sequence under low stringency conditions, preferably medium stringency conditions, most preferably, high stringency conditions (as defined above).

The term "substantially identical", when used herein with respect to a nucleotide sequence, means a nucleotide sequence corresponding to a reference or target nucleotide sequence, wherein the percentage of identity between the substantially identical nucleotide sequence and the reference or target nucleotide sequence is at least 60%, at least 70%, at least 80% or 85%, at least 90%, at least 93%, at least 95% or 96%, at least 97% or 98%, at least 99% or 100% (the later being equivalent to the term "identical" in this context). For example, identity is assessed over a length of 10-22 nucleotides, such as at least 10, 11, 12, 13, 14, 15, 16, 17, 18, 19, 20, 21, 22 or up to 50 nucleotides of a nucleic acid sequence to said reference sequence (if not specified otherwise below). Sequence comparisons are carried out using default GAP analysis with the University of Wisconsin GCG, SEQWEB application of GAP, based on the algorithm of Needleman and Wunsch (Needleman and Wunsch (1970) J MoI. Biol. 48: 443-453; as defined above). A nucleotide sequence "substantially identical" to a reference nucleotide sequence hybridizes to the exact complementary sequence of the reference nucleotide sequence (i.e., its corresponding strand in a double-stranded molecule) under low stringency conditions, preferably medium stringency conditions, most preferably high stringency conditions (as defined above). Homologues of a specific nucleotide sequence include nucleotide sequences that encode an amino acid sequence that is at least 24% identical, at least 35% identical, at least 50% identical, at least 65% identical to the reference amino acid sequence, as measured using the parameters described above, wherein the amino acid sequence encoded by the homolog has the same biological activity as the protein encoded by the specific nucleotide. The term "substantially non-identical" refers to a nucleotide sequence that does not hybridize to the nucleic acid sequence under stringent conditions.

The term "disease" or "disorder" is used interchangeably herein, refers to any alternation in state of the body or of some of the organs, interrupting or disturbing the performance of the functions and/or causing symptoms such as discomfort, dysfunction, distress, or even death to the person afflicted or those in contact with a person. A disease or disorder can also related to a distemper, ailing, ailment, malady, disorder, sickness, illness, complaint, inderdisposion, affection.

The terms "malignancy" or "cancer" are used interchangeably herein and refers to any disease of an organ or tissue in mammals characterized by poorly controlled or uncontrolled multiplication of normal or abnormal cells in that tissue and its effect on the body as a whole. Cancer diseases within the scope of the definition comprise benign neoplasms, dysplasias, hyperplasias as well as neoplasms showing metastatic growth or any other transformations like e.g., leukoplakias which often precede a breakout of cancer. The term "tumor" or "tumor cell" are used interchangeably herein, refers to the tissue mass or tissue type of cell that is undergoing abnormal proliferation.

The term "biological sample", "bodily sample", or "sample" as used herein refers to a cell or population of cells or a quantity of tissue or fluid from a subject. Most often, the sample has been removed from a subject, but the term "biological sample" can also refer to cells or tissue analyzed in vivo, i.e., without removal from the subject. Often, a "biological sample" will contain cells from the animal, but the term can also refer to non-cellular biological material, such as non-cellular fractions of blood, saliva, or urine, that can be used to measure gene or protein expression levels. Biological samples include, but are not limited to, tissue biopsies, scrapes (e.g., buccal scrapes), whole blood, plasma, serum, urine, saliva, cell culture, or cerebrospinal fluid. Biological samples also include tissue biopsies, cell culture. A biological sample or tissue sample can refers to a sample of tissue or fluid isolated from an individual, including but not limited to, for example, blood, plasma, serum, tumor biopsy, urine, stool, sputum, spinal fluid, pleural fluid, nipple aspirates, lymph fluid, the external sections of the skin, respiratory, intestinal, and genitourinary tracts, tears, saliva, milk, cells (including but not limited to blood cells), tumors, organs, and also samples of in vitro cell culture constituent. In some embodiments, the sample is from a resection, bronchoscopic biopsy, or core needle biopsy of a primary or metastatic tumor, or a cellblock from pleural fluid. In addition, fine needle aspirate samples are used. Samples may be either paraffin-embedded or frozen tissue. The sample can be obtained by removing a sample of cells from a subject, but can also be accomplished by using previously isolated cells (e.g., isolated by another person), or by performing the methods of the invention in vivo. Biological sample also refers to a sample of tissue or fluid isolated from an individual, including but not limited to, for example, blood, plasma, serum, tumor biopsy, urine, stool, sputum, spinal fluid, pleural fluid, nipple aspirates, lymph fluid, the external sections of the skin, respiratory, intestinal, and genitourinary tracts, tears, saliva, milk, cells (including but not limited to blood cells), tumors, organs, and also samples of in vitro cell culture constituent. In some embodiments, the biological samples can be prepared, for example biological samples may be fresh, fixed, frozen, or embedded in paraffin.

The term "tissue" is intended to include intact cells, blood, blood preparations such as plasma and serum, bones, joints, muscles, smooth muscles, and organs.

The term "treatment" refers to any treatment of a pathologic condition in a subject, particularly a human subject, and includes one or more of the following: (a) preventing a pathological condition from occurring in a subject which may be predisposition to the condition but has not yet been diagnosed with the condition and, accordingly, the treatment constitutes prophylactic treatment for the disease or condition; (b) inhibiting the pathological condition, i.e., arresting its development, (c) relieving the pathological condition, i.e. causing a regression of the pathological condition; or (d) relieving the conditions mediated by the pathological condition.

The term "computer" refers to any non-human apparatus that is capable of accepting a structured input, processing the structured input according to prescribed rules, and producing results of the processing as output. Examples of a computer include: a computer; a general purpose computer; a supercomputer; a mainframe; a super mini-computer; a mini-computer; a workstation; a micro-computer; a server; an interactive television; a hybrid combination of a computer and an interactive television; and application-specific hardware to emulate a computer and/or software. A computer can have a single processor or multiple processors, which can operate in parallel and/or not in parallel. A computer also refers to two or more computers connected together via a network for transmitting or receiving information between the computers. An example of such a computer includes a distributed computer system for processing information via computers linked by a network.

The term "computer-readable medium" may refer to any storage device used for storing data accessible by a computer, as well as any other means for providing access to data by a computer. Examples of a storage-device-type computer-readable medium include: a magnetic hard disk; a floppy disk; an optical disk, such as a CD-ROM and a DVD; a magnetic tape; a memory chip.

The term "software" is used interchangeably herein with "program" and refers to prescribed rules to operate a computer. Examples of software include: software; code segments; instructions; computer programs; and programmed logic.

The term a "computer system" may refer to a system having a computer, where the computer comprises a computer-readable medium embodying software to operate the computer.

The term "statistically significant" or "significantly" refers to statistical significance and generally means a two standard deviation (2SD) below normal, or lower, concentration of the marker. The term refers to statistical evidence that there is a difference. It is defined as the probability of making a decision to reject the null hypothesis when the null hypothesis is actually true. The decision is often made using the p-value.

The term "optional" or "optionally" means that the subsequent described event, circumstance or substituent may or may not occur, and that the description includes instances where the event or circumstance occurs and instances where it does not.

Other than in the operating examples, or where otherwise indicated, all numbers expressing quantities of ingredients or reaction conditions used herein should be understood as modified in all instances by the term "about." The term "about" when used in connection with percentages can mean+/−0.1%.

As used herein, the word "or" means any one member of a particular list and also includes any combination of members of that list. The words "comprise," "comprising," "include," "including," and "includes" when used in this specification and in the following claims are intended to specify the presence of one or more stated features, integers, components, or steps, but they do not preclude the presence or addition of one or more other features, integers, components, steps, or groups thereof.

In this specification and the appended claims, the singular forms "a," "an," and "the" include plural references unless the context clearly dictates otherwise, and therefore "a" and "an" are used herein to refer to one or to more than one (i.e., at least one) of the grammatical object of the article. By way of example, "an element" means one element or more than one element, and reference to a composition for delivering "an agent" includes reference to one or more agents.

Compositions or methods "comprising" one or more recited elements may include other elements not specifically recited. For example, a composition that comprises an inhibitor of HER2-associated RNA encompasses both an inhibitor of HER2-associated RNA but may also include other agents or other components. By way of further example, a composition that comprises elements A and B also encompasses a composition consisting of A, B and C. The terms "comprising" means "including principally, but not necessary solely". Furthermore, variation of the word "comprising", such as "comprise" and "comprises", have correspondingly varied meanings. The term "consisting essentially" means "including principally, but not necessary solely at least one", and as such, is intended to mean a "selection of one or more, and in any combination."

Embodiments described herein relate to RNAs (e.g., lincRNAs or mRNAs) associated with HER2 signaling (HER2-associated RNA) in HER2 positive human breast cancer cells, methods and compositions of modulating the levels of HER2-associated RNA in breast cancer cells of the subject to treat breast cancer cells or a subject in need thereof, and/or methods of measuring the expression profile of HER2-associated RNA to determine whether the subject has breast cancer or an increased risk of breast cancer and/or the efficacy of a therapeutic regimen.

The amplification of the HER2 gene in 20-30% of early stage breast cancer patients demonstrates the important role of this genetic event in breast cancer tumorgenesis. To determine the effects of HER2 amplification on gene expression, a number of previous studies have examined changes in mRNA expression in HER2+ breast cancer cell lines in response to HER2 inhibition using mRNA microarrays. However, these microarrays are limited in both the dynamic range as well as in the number of gene targets that can be interrogated. Furthermore, since these studies were all performed using cell lines, it was not possible to determine their relevance to what takes place in tumors in vivo.

We identified mRNAs that are clearly dysregulated in HER2+ tumors and become significantly affected by HER2 depletion or inhibition. Several of these genes are known to affect cell growth and proliferation and can impact tumorgenesis as a result of HER2 amplification. For example, we identified the RRM2 gene, which has been previously shown to be associated with decreased survival in breast cancer, to be highly upregulated in HER2+ tumors and is significantly downregulated by both HER2 inhibition and depletion. Another key gene that we identified is TOP2A, which is required for gene transcription and has been a target of several anti-cancer drugs, is also affected by HER2 inhibition/depletion. A final example is PRC1, which is highly upregulated during S and G2/M phases of mitosis is also downregulated by both HER2 knock down and trastuzumab-mediated inhibition.

Although the overexpression of HER2 in breast cancer has been known and studied, most studies have focused on identifying proteins as therapeutic targets. It was found that under expressed or over-expressed HER2-associated RNA in breast cancer cells compared to normal cells can be targeted by agents that promote induction or inhibition, respectively to treat breast cancer cells.

As shown in the Examples, gene expression analyses of HER2-associated RNA demonstrated that breast cancer cell lines dramatically repress expression of some HER2-associated RNA but dramatically promote expression of others compared to normal breast cells. Restoring HER2-associated RNA expression levels to those similar to normal cells resulted in can reduce growth of the breast cancer cells, potentially via the modulation of several pathways.

Table 1 lists RNA and lincRNA that are dysregulated in HER2+ breast cancer cells compared to normal cells.

TABLE 1

| RNA | SEQ ID NO. |
|---|---|
| RRM2 | 1 |
| TOP2A | 2 |
| CCNE2 | 3 |
| EXO1 | 4 |
| ANLN | 5 |
| DLGAP5 | 6 |
| CDKN3 | 7 |
| NUSAP1 | 8 |
| CCNB2 | 9 |
| FAM11B | 10 |
| HISH1H2BG | 11 |
| BUB1B | 12 |
| CDC6 | 13 |
| MAL2 | 14 |
| SQLE | 15 |
| KIF23 | 16 |
| CCNB1 | 17 |
| PRC1 | 18 |
| CKS2 | 19 |
| GINS1 | 20 |
| HIST1H2BO | 21 |
| ECT2 | 22 |
| ATAD2 | 23 |
| GGCT | 24 |
| HISST2H2BE | 25 |
| NME1 | 26 |
| GALNT7 | 27 |
| MCM4 | 28 |
| DHCR24 | 29 |
| RAD21 | 30 |
| TMEM97 | 31 |
| HMGCS1 | 32 |
| MCM01 | 33 |
| LMNB2 | 34 |
| MERTK | 35 |
| linc-STRAD6-2 | 36 |
| linc-GJA1-2 | 37 |
| linc-SLC39A10-10 | 38 |

In some embodiments, the agent administered to the breast cancer cells can be effective to decrease, reduce or downregulate the level of HER2-associated RNA that is over-expressed or upregulated in the breast cancer cells compared to normal cells. As used herein, the term "down-regulate", or "reduce", means that the level of HER2-associated RNA molecules or equivalent RNA is reduced below that observed in comparative normal cells. The HER2-associated RNA is down-regulated when expression of the HER2-associated RNA molecules is reduced at least 10%, at least about 20%, at least about 30%, at least about 50%, or at least about 75% relative to a corresponding non-modulated control. Thus, in some embodiments, the agent can be an inhibitor (e.g., antagonist) of HER2-associated RNA that is upregulated or over expressed in the breast cancer cells compared to normal cells.

In one example, HER2-associate RNA that is over expressed or upregulated in breast cancer cells compared to normal cells can include at least one of RRM2, TOP2A, CCNE2, EXO1, ANLN, DLGAP5, CDKN3, NUSAP1, CCNB2, FAM11B, HISH1H2BG, BUB1B, CDC6, MAL2, SQLE, KIF23, CCNB1, PRC1, CKS2, GINS1, HIST1H2BO, ECT2, ATAD2, GGCT, HISST2H2BE, NME1, GALNT7, MCM4, DHCR24, RAD21, TMEM97, HMGCS1, MSM01, LMNB2, or linc-STRAD6-2.

In another example, the HER2 associated RNA that is over expressed can include at least one of MAL2, ATAD2, GGCT, GALNT7, TMEM97, HMGCS1, MSM01.

In yet another example, the HER2 associated RNA that is over expressed can include linc-STRAD6-2.

An inhibitor of HER2-associated RNA, which is upregulated or over expressed in breast cancer cells compared to normal cells, can include any agent that inhibits or reduces HER2-associated RNA expression or function. Agents that inhibit or reduce HER2-associated RNA expression or function can be any type of entity, for example, chemicals, nucleic acid sequences, nucleic acid analogues, proteins, peptides or fragments thereof. In some embodiments, the agent is any chemical, entity or moiety, including without limitation, synthetic and naturally-occurring non-proteinaceous entities. In certain embodiments the agent is a small molecule having a chemical moiety.

In some embodiments, agents that inhibit or reduce HER2-associated RNA expression or function are nucleic acids. Nucleic acid inhibitors of HER2-associated RNA expression or function include, for example, RNA interference (RNAi) molecules or constructs, such as siRNA, dsRNA, stRNA, shRNA, microRNA and modified versions thereof, where the RNA interference molecule silences the expression or function of the HER2-associated RNA. The RNAi molecule of HER2-associated RNA can have a nucleic acid sequence that is substantially complementary to a portion of at least one HER2-associated RNA that is upregulated in the cancer cells. For example, the RNAi molecule of HER2-associated RNA can have nucleic acid sequence that is substantially complementary to a portion of at least one HER2-associated RNA selected from the group consisting of RRM2, TOP2A, CCNE2, EXO1, ANLN, DLGAP5, CDKN3, NUSAP1, CCNB2, FAM11B, HISH1H2BG, BUB1B, CDC6, MAL2, SQLE, KIF23, CCNB1, PRC1, CKS2, GINS1, HIST1H2BO, ECT2, ATAD2, GGCT, HISST2H2BE, NME1, GALNT7, MCM4, DHCR24, RAD21, TMEM97, HMGCS1, MSM01, LMNB2, and linc-STRAD6-2.

In some embodiments single-stranded RNA (ssRNA), a form of RNA endogenously found in eukaryotic cells can be used to form an RNAi molecule. Cellular ssRNA molecules include messenger RNAs (and the progenitor pre-messenger RNAs), small nuclear RNAs, small nucleolar RNAs, transfer RNAs and ribosomal RNAs. Double-stranded RNA (dsRNA) induces a size-dependent immune response such that dsRNA larger than 30 bp activates the interferon response, while shorter dsRNAs feed into the cell's endogenous RNA interference machinery downstream of the Dicer enzyme.

RNA interference (RNAi) provides a powerful approach for inhibiting the expression of selected target RNAs. RNAi uses small interfering RNA (siRNA) duplexes that target the RNA for selective degradation. siRNA-dependent post-transcriptional silencing of gene expression involves cutting the target messenger RNA molecule at a site guided by the siRNA.

RNA interference (RNAi) is an evolutionally conserved process whereby the expression or introduction of RNA of a sequence that is identical or highly similar to a target gene results in the sequence specific degradation or specific post-transcriptional gene silencing (PTGS) of messenger RNA (mRNA) transcribed from that targeted gene (see Coburn, G. and Cullen, B. (2002) J. of Virology 76(18): 9225), thereby inhibiting expression of the target gene. In one embodiment, the RNA is double stranded RNA (dsRNA). This process has been described in plants, invertebrates, and mammalian cells. In nature, RNAi is initiated by the dsRNA-specific endonuclease Dicer, which promotes processive cleavage of long dsRNA into double-stranded fragments termed siRNAs. siRNAs are incorporated into a protein complex (termed "RNA induced silencing complex," or "RISC") that recognizes and cleaves target mRNAs. RNAi can also be initiated by introducing nucleic acid molecules, e.g., synthetic siRNAs or RNA interfering agents, to inhibit or silence the expression of target genes. As used herein, "inhibition of target gene expression" includes any decrease in expression or level of the target gene as compared to a situation wherein no RNA interference has been induced. The decrease can be of at least about 30%, 40%, 50%, 60%, 70%, 80%, 90%, 95% or 99% or more as compared to the expression of a target gene or the activity or level of the protein encoded by a target gene which has not been targeted by an RNA interfering agent.

"Short interfering RNA" (siRNA), also referred to herein as "small interfering RNA" refers to an agent which functions to inhibit expression of a target gene, e.g., by RNAi. An siRNA can be chemically synthesized, can be produced by in vitro transcription, or can be produced within a host cell. In one embodiment, siRNA is a double stranded RNA (dsRNA) molecule of about 15 to about 40 nucleotides in length, preferably about 15 to about 28 nucleotides, more preferably about 19 to about 25 nucleotides in length, and more preferably about 19, 20, 21, 22, or 23 nucleotides in length, and can contain a 3' and/or 5' overhang on each strand having a length of about 0, 1, 2, 3, 4, or 5 nucleotides. The length of the overhang is independent between the two strands, i.e., the length of the overhang on one strand is not dependent on the length of the overhang on the second strand. Preferably the siRNA is capable of promoting RNA interference through degradation or specific post-transcriptional gene silencing (PTGS) of the target messenger RNA (mRNA).

siRNAs also include small hairpin (also called stem loop) RNAs (shRNAs). In one embodiment, these shRNAs are composed of a short (e.g., about 19 to about 25 nucleotide) antisense strand, followed by a nucleotide loop of about 5 to about 9 nucleotides, and the analogous sense strand. Alternatively, the sense strand can precede the nucleotide loop structure and the antisense strand can follow. These shRNAs can be contained in plasmids, retroviruses, and lentiviruses and expressed from, for example, the pol III U6 promoter, or another promoter (see, e.g., Stewart, et al. (2003) RNA April; 9(4):493-501, incorporated by reference herein in its entirety).

A siRNA can be substantially homologous to the target gene or genomic sequence, or a fragment thereof. As used in this context, the term "homologous" is defined as being substantially identical, sufficiently complementary, or similar to the target mRNA, or a fragment thereof, to effect RNA interference of the target. In addition to native RNA molecules, RNA suitable for inhibiting or interfering with the expression of a target sequence include RNA derivatives and analogs.

The siRNA targets only one sequence. Each of the RNA interfering agents, such as siRNAs, can be screened for potential off-target effects by, for example, expression profiling. Such methods are known to one skilled in the art and are described, for example, in Jackson et al, Nature Biotechnology 6:635-637, 2003. In addition to expression profiling, one can also screen the potential target sequences for similar sequences in the sequence databases to identify potential sequences which can have off-target effects. For example, according to Jackson et al. (Id.) 15, or perhaps as few as 11 contiguous nucleotides of sequence identity are sufficient to direct silencing of non-targeted transcripts. Therefore, one can initially screen the proposed siRNAs to avoid potential off-target silencing using the sequence identity analysis by any known sequence comparison methods, such as BLAST.

siRNA molecules need not be limited to those molecules containing only RNA, but, for example, further encompass chemically modified nucleotides and non-nucleotides, and also include molecules wherein a ribose sugar molecule is substituted for another sugar molecule or a molecule which performs a similar function. Moreover, a non-natural linkage between nucleotide residues can be used, such as a phosphorothioate linkage. For example, siRNA containing D-arabinofuranosyl structures in place of the naturally-occurring D-ribonucleosides found in RNA can be used in RNAi molecules according to the present invention (U.S. Pat. No. 5,177,196).

The RNA strand can be derivatized with a reactive functional group of a reporter group, such as a fluorophore. Particularly useful derivatives are modified at a terminus or termini of an RNA strand, typically the 3' terminus of the sense strand. For example, the 2'-hydroxyl at the 3' terminus can be readily and selectively derivatized with a variety of groups.

Other useful RNA derivatives incorporate nucleotides having modified carbohydrate moieties. The RNA bases can also be modified. Any modified base useful for inhibiting or interfering with the expression of a target sequence can be used. For example, halogenated bases, such as 5-bromouracil and 5-iodouracil can be incorporated. The bases can also be alkylated, for example, 7-methylguanosine can be incorporated in place of a guanosine residue. Non-natural bases that yield successful inhibition can also be incorporated.

siRNA and miRNA molecules having various "tails" covalently attached to either their 3'- or to their 5'-ends, or to both, are also known in the art and can be used to stabilize the siRNA and miRNA molecules delivered using the methods of the present invention. Generally speaking, intercalating groups, various kinds of reporter groups and lipophilic groups attached to the 3' or 5' ends of the RNA molecules are well known to one skilled in the art and are useful according to the methods of the present invention. Descriptions of syntheses of 3'-cholesterol or 3'-acridine modified oligonucleotides applicable to preparation of modified RNA molecules useful according to the present invention can be found, for example, in the articles: Gamper, H. B., Reed, M. W., Cox, T., Virosco, J. S., Adams, A. D., Gall, A., Scholler, J. K., and Meyer, R. B. (1993) Facile Preparation and Exonuclease Stability of 3'-Modified Oligodeoxynucleotides. Nucleic Acids Res. 21 145-150; and Reed, M. W., Adams, A. D., Nelson, J. S., and Meyer, R. B., Jr. (1991) Acridine and Cholesterol-Derivatized Solid Supports for Improved Synthesis of 3'-Modified Oligonucleotides. Bioconjugate Chem. 2 217-225 (1993).

Other siRNAs useful for targeting HER2-associated RNA expression or function can be readily designed and tested. Accordingly, siRNAs useful for the methods described herein include siRNA molecules of about 15 to about 40 or about 15 to about 28 nucleotides in length. In some embodiments, the HER2-associated RNA targeting siRNA molecules can have a length of about 25 to about 29 nucleotides. In other embodiments, the HER2-associated RNA targeting siRNA molecules have a length of about 27, 28, 29, or 30 nucleotides. The HER2-associated RNA targeting siRNA molecules can also comprise a 3' hydroxyl group. The HER2-associated RNA targeting siRNA molecules can be single-stranded or double stranded; such molecules can be blunt ended or comprise overhanging ends (e.g., 5', 3'). In specific embodiments, the RNA molecule is double stranded and either blunt ended or comprises overhanging ends.

In some embodiments, the siRNA or modified siRNA, such as gene silencing RNAi agents, and/or gene activating RNAi agents are delivered in a pharmaceutically acceptable carrier. Additional carrier agents, such as liposomes, can be added to the pharmaceutically acceptable carrier.

In another embodiment, the siRNA is delivered by delivering a vector encoding small hairpin RNA (shRNA) in a pharmaceutically acceptable carrier to the cells in an organ of an individual. The shRNA is converted by the cells after transcription into siRNA capable of targeting, for example, the HER2-associated RNA, to inhibit its function and/or expression. In one embodiment, the vector can be a regulatable vector, such as tetracycline inducible vector.

In one embodiment, the RNA interfering agents used in the methods described herein are taken up actively by cells in vivo following intravenous injection, e.g., hydrodynamic injection, without the use of a vector, illustrating efficient in vivo delivery of the RNA interfering agents, e.g., the siRNAs used in the methods described herein.

Other strategies for delivery of the RNA interfering agents, e.g., the siRNAs or shRNAs used in the methods described herein, can also be employed, such as, for example, delivery by a vector, e.g., a plasmid or viral vector, e.g., a lentiviral vector. Such vectors can be used as described, for example, in Xiao-Feng Qin et al. Proc. Natl. Acad. Sci. U.S.A., 100: 183-188. Other delivery methods include delivery of the RNA interfering agents, e.g., the siRNAs or shRNAs, using a basic peptide by conjugating or mixing the RNA interfering agent with a basic peptide, e.g., a fragment of a TAT peptide, mixing with cationic lipids or formulating into particles.

As noted, the RNA interfering agents, such as siRNA or shRNA can be delivered using an inducible vector, such as a tetracycline inducible vector. Methods described, for example, in Wang et al. Proc. Natl. Acad. Sci. 100: 5103-5106, using pTet-On vectors (BD Biosciences Clontech, Palo Alto, Calif.) can be used. In some embodiments, a vector can be a plasmid vector, a viral vector, or any other suitable vehicle adapted for the insertion and foreign sequence and for the introduction into eukaryotic cells. The vector can be an expression vector capable of directing the transcription of the DNA sequence of the agonist or antagonist nucleic acid molecules into RNA. Viral expression vectors can be selected from a group comprising, for example, reteroviruses, lentiviruses, Epstein Barr virus-, bovine papilloma virus, adenovirus- and adeno-associated-based vectors or hybrid virus of any of the above. In one embodiment, the vector is episomal. The use of a episomal vector provides a means of maintaining the antagonist nucleic acid molecule in the subject in high copy number extra chromosomal DNA thereby eliminating potential effects of chromosomal integration.

RNA interfering agents and nucleic acid inhibitors used in the methods as disclosed herein can be produced using any known techniques, such as direct chemical synthesis, through processing of longer double stranded RNAs by exposure to recombinant Dicer protein or *Drosophila* embryo lysates, through an in vitro system derived from S2 cells, using phage RNA polymerase, RNA-dependant RNA polymerase, and DNA based vectors. Use of cell lysates or in vitro processing can further involve the subsequent isolation of the short, for example, about 21-23 nucleotide, siRNAs from the lysate, etc. Chemical synthesis usually proceeds by making two single stranded RNA-oligomers followed by the annealing of the two single stranded oligomers into a double stranded RNA. Other examples include methods disclosed in WO 99/32619 and WO 01/68836 that teach chemical and enzymatic synthesis of siRNA. Moreover, numerous commercial services are available for designing and manufacturing specific siRNAs (see, e.g., QIAGEN Inc., Valencia, Calif. and AMBION Inc., Austin, Tex.)

In one embodiment, an inhibitor of HER2-associated RNA function and/or its expression can be obtained synthetically, for example, by chemically synthesizing a nucleic acid by any method of synthesis known to the skilled artisan. A synthesized nucleic acid inhibitor of HER2-associated RNA function and/or its expression can then be purified by any method known in the art. Methods for chemical synthesis of nucleic acids include, but are not limited to, in vitro chemical synthesis using phosphotriester, phosphate or phosphoramidite chemistry and solid phase techniques, or via deoxynucleoside H-phosphonate intermediates (see U.S. Pat. No. 5,705,629 to Bhongle).

Synthetic siRNA molecules, including shRNA molecules, can also easily be obtained using a number of techniques known to those of skill in the art. For example, the siRNA molecule can be chemically synthesized or recombinantly produced using methods known in the art, such as using appropriately protected ribonucleoside phosphoramidites and a conventional DNA/RNA synthesizer (see, e.g., Elbashir, S. M. et al. (2001) Nature 411:494-498; Elbashir, S. M., W. Lendeckel and T. Tuschl (2001) Genes & Development 15:188-200; Harborth, J. et al. (2001) J. Cell Science 114:4557-4565; Masters, J. R. et al. (2001) Proc. Natl. Acad. Sci., USA 98:8012-8017; and Tuschl, T. et al. (1999) Genes & Development 13:3191-3197). Alternatively, several commercial RNA synthesis suppliers are available including, but are not limited to, Proligo (Hamburg, Germany), Dharmacon Research (Lafayette, Colo., USA), Pierce Chemical (part of Perbio Science, Rockford, Ill., USA), Glen Research (Sterling, Va., USA), ChemGenes (Ashland, Mass., USA), and Cruachem (Glasgow, UK). As such, siRNA molecules are not overly difficult to synthesize and are readily provided in a quality suitable for RNAi. In addition, dsRNAs can be expressed as stem loop structures encoded by plasmid vectors, retroviruses and lentiviruses (Paddison, P. J. et al.

(2002) Genes Dev. 16:948-958; McManus, M. T. et al. (2002) RNA 8:842-850; Paul, C. P. et al. (2002) Nat. Biotechnol. 20:505-508; Miyagishi, M. et al. (2002) Nat. Biotechnol. 20:497-500; Sui, G. et al. (2002) Proc. Natl. Acad. Sci., USA 99:5515-5520; Brummelkamp, T. et al. (2002) Cancer Cell 2:243; Lee, N. S., et al. (2002) Nat. Biotechnol. 20:500-505; Yu, J. Y., et al. (2002) Proc. Natl. Acad. Sci., USA 99:6047-6052; Zeng, Y., et al. (2002) Mol. Cell. 9:1327-1333; Rubinson, D. A., et al. (2003) Nat. Genet. 33:401-406; Stewart, S. A., et al. (2003) RNA 9:493-501). These vectors generally have a polIII promoter upstream of the dsRNA and can express sense and antisense RNA strands separately and/or as a hairpin structures. Within cells, Dicer processes the short hairpin RNA (shRNA) into effective siRNA.

Methods of delivering RNAi agents, e.g., a siRNA, or vectors containing an RNAi agent, to the target cells (e.g., colon cancer cells, breast cancer cells, or other desired target cells) are well known to persons of ordinary skill in the art. In some embodiments, a RNAi agent inhibitor of HER2-associated RNA function and/or its expression can be administered to a subject by injection of a composition containing the RNA interfering agent, e.g., an siRNA, or directly contacting the cell with a composition comprising an RNAi agent, e.g., an siRNA. In another embodiment, RNAi agents, e.g., a siRNA can be injected directly into any blood vessel, such as vein, artery, venule or arteriole, via, e.g., hydrodynamic injection or catheterization.

Administration can be by a single injection or by two or more injections. In some embodiments, a RNAi agent is delivered in a pharmaceutically acceptable carrier. A gene silencing-RNAi agent, which inhibits HER2-associated RNA function and/or its expression can also be administered in combination with other pharmaceutical agents which are used to treat or prevent cancer.

In one embodiment, specific cells are targeted with RNA interference, limiting potential side effects of RNA interference caused by non-specific targeting of RNA interference. The method can use, for example, a complex or a fusion molecule comprising a cell targeting moiety and an RNA interference binding moiety that is used to deliver RNAi effectively into cells. In some embodiments, a siRNA or RNAi binding moiety is a protein or a nucleic acid binding domain or fragment of a protein, and the binding moiety is fused to a portion of the targeting moiety. The location of the targeting moiety can be either in the carboxyl-terminal or amino-terminal end of the construct or in the middle of the fusion protein.

In some embodiments, a viral-mediated delivery mechanism can also be employed to deliver siRNAs, e.g., siRNAs (e.g., gene silencing-RNAi agents) which inhibits HER2-associated RNA function and/or its expression to cells in vitro and in vivo as described in Xia, H. et al. (2002) Nat Biotechnol 20(10):1006). Plasmid- or viral-mediated delivery mechanisms of shRNA can also be employed to deliver shRNAs to cells in vitro and in vivo as described in Rubinson, D. A., et al. ((2003) Nat. Genet. 33:401-406) and Stewart, S. A., et al. ((2003) RNA 9:493-501).

The dose of the particular RNAi agent will be in an amount necessary to effect RNA interference, e.g., gene silencing RNAi which inhibits HER2-associated RNA function and/or its expression leading to reduction of HER2-associated RNA level.

In other embodiments, an agent that modulates the level of HER2-associated RNA in the breast cancer cells of the subject can be an agent that increases, enhances or upregulates the level of HER2-associated RNA, which is under-expressed or downregulated in the cancer cells compared to normal cells. The agent can include, for example, a nucleic acid encoding the under expressed or downregulated HER2-associated RNA in the cancer cells.

In one example, the HER2-associated RNA that is under expressed or downregulated in the cancer cells can include at least one of MERTK, linc-GJA1-2 or Linc-SLC39A10-10.

In some embodiments, a nucleic acid encoding the HER2-associated RNA can be substantially homologous or have a sequence identity that is substantially identical to native (or nonmutated) HER2-associated RNA such that when the nucleic acid encoding the HER2-associated RNA is administered to breast cancer cells of the subject, cancer growth, proliferation and/or metastasis is inhibited or reduced. By substantially homologous, it is meant the HER2-associated RNA has an at least about 80%, about 90%, about 95%, about 96%, about 97%, about 98%, about 99% or about 100% sequence identity with the nucleotide sequence of the native (or nonmutated) HER2-associated RNA.

In some embodiments, a nucleic acid encoding the down-regulated HER2-associated RNA can have a nucleic acid sequence substantially homologous to the HER2-associated RNA or corresponding nucleic acid sequence selected from the group consisting of MERTK, linc-GJA1-2, and Linc-SLC39A10-10. The nucleic encoding the HER2-associated RNA can be administered to cells through gene therapy using, for example, a nucleic acid construct. In general, there are two approaches to gene therapy in humans. For in vivo gene therapy, a nucleic acid construct encoding the nucleic acid or polynucleotide of interest can be administered directly to the subject or cells. Alternatively, in ex vivo gene therapy, cells are removed from the subject and treated with a nucleic acid construct to express the gene of interest. In the ex vivo method of gene therapy, the treated cells are then re-administered to the patient.

Numerous different methods for gene therapy are well known in the art. These methods include, but are not limited to, the use of nucleic acid constructs provided in DNA plasmid vectors as well as DNA and RNA viral vectors. These vectors are engineered to express HER2-associated RNA when integrated into patient cells.

Additionally, nucleic acid constructs for use in methods described herein may have expression signals, such as a strong promoter, a strong termination codon, adjustment of the distance between the promoter and the cloned gene, and the insertion of a transcription termination sequence.

In certain aspects, the nucleic acid construct includes a nucleic acid substantially homologous to HER2-associated RNA operably linked to a promoter to facilitate HER2-associated RNA expression within a breast cancer cell. The promoter may be a strong, viral promoter that functions in eukaryotic cells, such as a promoter derived from cytomegalovirus (CMV), simian virus 40 (SV40), mouse mammary tumor virus (MMTV), Rous sarcoma virus (RSV), or adenovirus.

Alternatively, the promoter used may be tissue-specific, cell type-specific promoter, or a strong general eukaryotic promoter, such as the actin gene promoter. In another aspect, the promoter is a regulated promoter, such as a tetracycline-regulated promoter, expression from which can be regulated by exposure to an exogenous substance (e.g., tetracycline).

Introduction of one or more of the nucleic acid construct(s) including a nucleic acid encoding a HER2-associated RNA can be achieved using a variety of gene transfer protocols permitting transfection of the nucleic acid construct into the cells. Genetic change can be accomplished either by incorporation of the new nucleic acid into the genome of the host cell, or by transient or stable maintenance of the new DNA as an episomal element. A cell has been "transfected" when the nucleic acid construct has been introduced inside the cell membrane using any technology used to introduce nucleic acid molecules into cells.

A number of transfection techniques are well known in the art and are disclosed herein. See, for example, Graham et al., Virology, 52: 456 (1973); Sambrook et al., Molecular Cloning, a laboratory Manual, Cold Spring Harbor Laboratories (New York, 1989); Davis et al., Basic Methods in Molecular Biology, Elsevier, 1986; and Chu et al., Gene, 13: 197 (1981). Such techniques can be used to introduce one or more nucleic acid constructs described herein into the cells.

In some aspects, the nucleic acid construct can be introduced into cancer cells using a viral vector. The precise vector and vector formulation used will depend upon several factors, such as the size of the nucleic acid construct to be transferred and the delivery protocol to be used. The nucleic acid construct can also be introduced as infectious particles, e.g., DNA-ligand conjugates, calcium phosphate precipitates, and liposomes.

In general, viral vectors used are composed of a viral particle derived from a naturally occurring virus, which has been genetically altered to render the virus replication-defective and to deliver a recombinant gene of interest for expression in a target cell. Numerous viral vectors are well known in the art, including, for example, retrovirus, lentivirus, adenovirus, adeno-associated virus, herpes simplex virus (HSV), cytomegalovirus (CMV), vaccinia and poliovirus vectors. The viral vector may be selected according to its preferential infection of the cells targeted.

Where a replication-deficient virus is used as the viral vector, the production of infectious virus particles containing either DNA or RNA corresponding to the nucleic acid construct can be achieved by introducing the viral construct into a recombinant cell line, which provides the missing components essential for viral replication. Transformation of the recombinant cell line with the recombinant viral vector will not result in production or substantial production of replication-competent viruses, e.g., by homologous recombination of the viral sequences of the recombinant cell line into the introduced viral vector. Methods for production of replication-deficient viral particles containing a nucleic acid of interest are well known in the art and are described in, for example, Rosenfeld et al., Science 252:431-434, 1991 and Rosenfeld et al., Cell 68:143-155, 1992 (adenovirus); U.S. Pat. No. 5,139,941 (adeno-associated virus); U.S. Pat. No. 4,861,719 (retrovirus); and U.S. Pat. No. 5,356,806 (vaccinia virus).

In other embodiments, the nucleic acid construct including a nucleic acid encoding a HER2-associated RNA may be introduced into a cell using a non-viral vector. "Non-viral vector" as used herein is meant to include naked RNA (e.g., RNA not contained within a viral particle, and free of a carrier molecules, such as lipids), chemical formulations comprising naked nucleic acid (e.g., a formulation of RNA (and/or DNA) and cationic compounds (e.g., dextran sulfate, cationic lipids)), and naked nucleic acid mixed with an adjuvant, such as a viral particle (e.g., the DNA or RNA of interest is not contained within the viral particle, but the formulation is composed of both naked DNA and viral particles (e.g., adenovirus particles) (see, e.g., Curiel et al. 1992 Am. J. Respir. Cell Mol. Biol. 6:247-52). Thus, "non-viral vector" can include vectors composed of nucleic acid plus viral particles where the viral particles do not contain the nucleic acid construct within the viral genome.

In some aspects, a liposome non-viral vector can be used to introduce the nucleic acid encoding the HER2-associated RNA into the cell. Liposomes for use in the method described herein can include a mixture of lipids, which bind to the nucleic acid construct and facilitate delivery of the construct into the cell. Examples of liposomes that can be used include DOPE (dioleyl phosphatidyl ethanol amine), CUDMEDA (N-(5-cholestrum-3-β-ol 3-urethanyl)-N1,N1-dimethylethylene diamine).

The nucleic acid encoding the HER2-associated RNA or vector thereof can be incorporated into pharmaceutical compositions suitable for administration to a subject. In some particular embodiments, the pharmaceutical composition comprises the vectors described herein and a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol and the like, as well as combinations thereof. In many cases, it can be preferable to include isotonic agents, for example, sugars, polyalcohols such as mannitol, sorbitol, or sodium chloride in the composition. Pharmaceutically acceptable carriers can further comprise minor amounts of auxiliary substances, such as wetting or emulsifying agents, preservatives or buffers, which enhance the shelf life or effectiveness of the vector or pharmaceutical composition.

The compositions described herein may be in a variety of forms. These include, for example, liquid, semi-solid and solid dosage forms, such as liquid solutions (e.g., injectable and infusible solutions), dispersions or suspensions, tablets, pills, powders, liposomes and suppositories. The form used depends on the intended mode of administration and therapeutic application. Typical compositions are in the form of injectable or infusible solutions.

Therapeutic compositions typically must be sterile and stable under the conditions of manufacture and storage. The composition can be formulated as a solution, microemulsion, dispersion, liposome, or other ordered structure suitable to high drug concentration. Sterile injectable solutions can be prepared by incorporating the vector in the required amount in an appropriate solvent with one or a combination of ingredients enumerated above, as required, followed by filtered sterilization.

Generally, dispersions are prepared by incorporating the vector into a sterile vehicle that contains a basic dispersion medium and the required other ingredients from those enumerated above. In the case of sterile lyophilized powders for the preparation of sterile injectable solutions, the methods of preparation can include vacuum drying and spray-drying that yields a powder of the active ingredient plus any additional desired ingredient from a previously sterile-filtered solution thereof. The proper fluidity of a solution can be maintained, for example, by the use of a coating, such as lecithin, by the maintenance of the required particle size in the case of dispersion and by the use of surfactants. Prolonged absorption of injectable compositions can be achieved by including an agent in the composition that delays absorption, for example, monostearate salts and gelatin.

The vectors described herein can be administered by a variety of methods known in the art. As will be appreciated by the skilled artisan, the route and/or mode of administration will vary depending upon the desired results. In certain embodiments, the vector may be prepared with a carrier that will protect the vector against rapid release, such as a controlled release formulation, including implants, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are generally known to those skilled in the art.

In some embodiments, one or more agents that decrease the level of HER2-associated RNA that is upregulated in the cancer cells and/or agents that increase the level of HER2-associated RNA that is downregulated in the cancer cells can be administered to cancer cells of the subject at an amount effective to modulate the level of HER2-associated RNA in the breast cancer cells of the subject and treat breast cancer. In some embodiments, the breast cancer is primary breast cancer.

Other embodiments described herein relate to compositions and methods for measuring the levels of HER2-associated RNA described herein to analyze tissue of a subject having or suspected of having breast cancer, predict whether a subject has breast cancer or an increased risk of breast cancer, determine breast cancer prognosis in a subject, and/or monitor a subject's response to a treatment regimen for breast cancer. For example, a biological sample (e.g., a tumor sample or blood sample) can be obtained from a subject and the level of at least one HER2-associated RNA selected from the group consisting of RRM2, TOP2A, CCNE2, EXO1, ANLN, DLGAP5, CDKN3, NUSAP1, CCNB2, FAM11B, HISH1H2BG, BUB1B, CDC6, MAL2, SQLE, KIF23, CCNB1, PRC1, CKS2, GINS1, HIST1H2BO, ECT2, ATAD2, GGCT, HISST2H2BE, NME1, GALNT7, MCM4, DHCR24, RAD21, TMEM97, HMGCS1, MSM01, LMNB2, MERTK, linc-STRAD6-2, linc-GJA1-2, linc-SLC39A10-10, and combinations thereof can be determined or measured from the sample of tissue to generate a HER2-associated RNA expression profile. The expression profile from the sample is then compared to an expression profile of a control or standard. A decrease in the expression of the at least one HER2-associated RNA selected from the group consisting of MERTK, linc-GJA1-2, Linc-SLC39A10-10 and combinations thereof and/or increase in the expression of the at least one HER2-associated RNA selected from the group consisting of RRM2, TOP2A, CCNE2, EXO1, ANLN, DLGAP5, CDKN3, NUSAP1, CCNB2, FAM11B, HISH1H2BG, BUB1B, CDC6, MAL2, SQLE, KIF23, CCNB1, PRC1, CKS2, GINS1, HIST1H2BO, ECT2, ATAD2, GGCT, HISST2H2BE, NME1, GALNT7, MCM4, DHCR24, RAD21, TMEM97, HMGCS1, MSM01, lMNB2, linc-STRAD6-2, and combinations thereof is indicative of the subject having cancer or an increased risk of cancer.

Measuring methods include any method of nucleic acid or protein detection, for example in situ hybridization for HER2-associated RNA using antisense DNA or RNA oligonucleotide probes, ultra-high throughput sequencing, Nanostring technology, microarrays, rolling circle amplification, proximity-mediated ligation, PCR, qRT-PCR ChIP, ChIP-qPCR or antibodies, or protein or nucleic acid measurements. Comparatively high levels of HER2-associated RNA compared to control levels in normal cells can indicate metastasis or poor cancer prognosis. Similarly, comparatively low levels of HER2-associated RNA compared to control levels in normal cells may indicate cancer progression.

In some embodiments, the level of secreted or transmembrane proteins of HER2-associated RNA, such as MAL2, ATAD2, GGCT, GALNT7, TMEM97, HMGCS1, and MSM01, can be measured in a bodily fluid (e.g., blood) of a subject to determine a subject having or suspected of having breast cancer, predict whether the subject has breast cancer or an increased risk of breast cancer, determine breast cancer prognosis in a subject, and/or monitor a subject's response to a treatment regimen for breast cancer.

Information on levels of a given set of HER2-associated RNA or protein thereof obtained using biological samples from individuals afflicted with or at risk of breast cancer may be grouped to form an expression profile map. The expression profile map can result from the study of a large number of individuals with the same cancer or cancer sub-type. In certain embodiments, a cancer expression profile map is established using samples from individuals with matched age, sex, and body index. Each expression profile map provides a template for comparison to HER2-associated RNA expression patterns generated from unknown biological samples. HER2-associated RNA expression profile maps may be presented as a graphical representation (e.g., on paper or a computer screen), a physical representation (e.g., a gel or array) or a digital representation stored in a computer-readable medium.

As will be appreciated by those of ordinary skill in the art, sets of biomarkers whose expression profiles correlate with breast cancer may be used to identify, study, or characterize unknown biological samples. Accordingly, in one aspect, methods for characterizing or analyzing biological samples obtained from a subject suspected of having breast cancer, for diagnosing breast cancer in a subject, and for assessing the responsiveness of breast cancer in a subject to treatment are contemplated. In such methods the HER2-associated RNA expression levels determined for a biological sample, obtained from the subject, are compared to the levels in one or more control samples. The control samples may be obtained from a healthy individual (or a group of healthy individuals), and/or from an individual (or group of individuals) afflicted with breast cancer. As mentioned above, the control expression levels of the HER2-associated RNA of interest are preferably determined from a significant number of individuals, and an average or mean is obtained. In certain aspects, the levels determined for the biological sample under investigation are compared to at least one expression profile map for cancer, as described above.

The methods described herein may be applied to the study of any type of biological samples allowing one or more inventive HER2-associated RNA to be assayed. Examples of biological samples include, but are not limited to, blood, blood products (e.g., blood plasma), and tissue. In a particular aspect of the present invention, the biological sample is tissue or biopsy obtained from the subject.

The biological samples used in the practice of the inventive methods may be fresh or frozen samples collected from a subject, or archival samples with known diagnosis, treatment and/or outcome history. Biological samples may be collected by any non-invasive means. Preferably, there is enough of the biological sample to accurately and reliably determine the abundance of the set of HER2-associated RNA of interest. Multiple biological samples may be taken from the subject in order to obtain a representative sampling from the subject.

In some embodiments, the HER2-associated RNA are extracted from the biological sample before analysis. Methods of RNA extraction are well known in the art (see, for example, J. Sambrook et al., "Molecular Cloning: A Laboratory Manual", 1989, 2nd Ed., Cold Spring Harbor Laboratory Press: Cold Spring Harbor, N.Y.). Most methods of RNA isolation from bodily fluids or tissues are based on the disruption of the tissue in the presence of protein denaturants to quickly and effectively inactivate RNAses. Isolated total RNA may then be further purified from the protein contaminants and concentrated by selective ethanol precipitations, phenol/chloroform extractions followed by isopropanol precipitation or cesium chloride, lithium chloride or cesium trifluoroacetate gradient centrifugations. Kits are also available to extract RNA (i.e., total RNA or mRNA) from bodily fluids or tissues and are commercially available from, for example, Ambion, Inc. (Austin, Tex.), Amersham Biosciences (Piscataway, N.J.), BD Biosciences Clontech (Palo Alto, Calif.), BioRad Laboratories (Hercules, Calif.), GIBCO BRL (Gaithersburg, Md.), and Qiagen, Inc. (Valencia, Calif.).

In certain aspects, after extraction, lincRNA, or mRNA is amplified, and transcribed into cDNA, which can then serve as template for multiple rounds of transcription by the appropriate RNA polymerase Amplification methods are well known in the art (see, for example, A. R. Kimmel and S. L. Berger, Methods Enzymol. 1987, 152: 307-316; J. Sambrook et al., “Molecular Cloning: A Laboratory Manual”, 1989, 2nd Ed., Cold Spring Harbour Laboratory Press: New York; “Short Protocols in Molecular Biology”, F. M. Ausubel (Ed.), 2002, 5th Ed., John Wiley & Sons; U.S. Pat. Nos. 4,683,195; 4,683,202 and 4,800,159). Reverse transcription reactions may be carried out using non-specific primers, such as an anchored oligo-dT primer, or random sequence primers, or using a target-specific primer complementary to the RNA for each probe being monitored, or using thermostable DNApolymerases (such as avian myeloblastosis virus reverse transcriptase or Moloney murine leukemia virus reverse transcriptase).

The diagnostic methods described herein generally involve the determination of the abundance levels of a plurality (i.e., one or more, e.g., at least 2, at least 3, at least 4, at least 5, at least 6, at least 7, at least 8, at least 9, at least 10 or more) of HER2-associated RNA in a biological sample obtained from a subject.

It will be appreciated that the diagnostic methods may involve determination of the expression levels of a set of HER2-associated RNA using any suitable method, including, but not limited to, polymerase chain reaction (PCR) (see, for example, U.S. Pat. Nos. 4,683,195; 4,683,202, and 6,040,166; “PCR Protocols: A Guide to Methods and Applications”, Innis et al. (Eds.), 1990, Academic Press: New York), reverse transcriptase PCR(RT-PCT), anchored PCR, competitive PCR (see, for example, U.S. Pat. No. 5,747, 251), rapid amplification of cDNA ends (RACE) (see, for example, “Gene Cloning and Analysis: Current Innovations, 1997, pp. 99-115); ligase chain reaction (LCR) (see, for example, EP 01 320308), one-sided PCR (Ohara et al., Proc. Natl. Acad. Sci., 1989, 86: 5673-5677), in situ hybridization, Taqman based assays (Holland et al., Proc. Natl. Acad. Sci., 1991, 88:7276-7280), differential display (see, for example, Liang et al., Nucl. Acid. Res., 1993, 21: 3269-3275) and other RNA fingerprinting techniques, nucleic acid sequence based amplification (NASBA) and other transcription based amplification systems (see, for example, U.S. Pat. Nos. 5,409,818 and 5,554,527), Qbeta Replicase, Strand Displacement Amplification (SDA), Repair Chain Reaction (RCR), nuclease protection assays, subtraction-based methods, Rapid-Scan™, and the like.

Nucleic acid probes for use in the detection of HER2-associated RNA in biological samples may be constructed using conventional methods known in the art. Suitable probes may be based on nucleic acid sequences encoding at least 5 sequential amino acids from regions of nucleic acids encoding a protein marker, and preferably comprise about 15 to about 50 nucleotides. A nucleic acid probe may be labeled with a detectable moiety, as mentioned above in the case of binding agents. The association between the nucleic acid probe and detectable moiety can be covalent or non-covalent. Detectable moieties can be attached directly to nucleic acid probes or indirectly through a linker (E. S. Mansfield et al., Mol. Cell. Probes, 1995, 9: 145-156). Methods for labeling nucleic acid molecules are well-known in the art (for a review of labeling protocols, label detection techniques and recent developments in the field, see, for example, L. J. Kricka, Ann. Clin. Biochem. 2002, 39: 114-129; R. P. van Gijlswijk et al., Expert Rev. Mol. Diagn. 2001, 1: 81-91; and S. Joos et al., J. Biotechnol. 1994, 35:135-153).

Nucleic acid probes may be used in hybridization techniques to detect HER2-associated RNA. The technique generally involves contacting an incubating nucleic acid molecules in a biological sample obtained from a subject with the nucleic acid probes under conditions such that specific hybridization takes place between the nucleic acid probes and the complementary sequences in the nucleic acid molecules. After incubation, the non-hybridized nucleic acids are removed, and the presence and amount of nucleic acids that have hybridized to the probes are detected and quantified.

Detection of HER2-associated RNA may involve amplification of specific polynucleotide sequences using an amplification method such as PCR, followed by analysis of the amplified molecules using techniques known in the art. Suitable primers can be routinely designed by one skilled in the art. In order to maximize hybridization under assay conditions, primers and probes employed in the methods of the invention generally have at least 60%, preferably at least 75% and more preferably at least 90% identity to a portion of nucleic acids encoding a protein marker.

Hybridization and amplification techniques described herein may be used to assay qualitative and quantitative aspects of expression of nucleic acid molecules comprising polynucleotide sequences coding for the inventive protein markers.

Alternatively, oligonucleotides or longer fragments derived from HER2-associated RNA may be used as targets in a microarray. A number of different array configurations and methods of their production are known to those skilled in the art (see, for example, U.S. Pat. Nos. 5,445,934; 5,532,128; 5,556,752; 5,242,974; 5,384, 261; 5,405,783; 5,412,087; 5,424,186; 5,429,807; 5,436,327; 5,472,672; 5,527,681; 5,529,756; 5,545,531; 5,554, 501; 5,561,071; 5,571,639; 5,593,839; 5,599,695; 5,624, 711; 5,658,734; and 5,700,637). Microarray technology allows for the measurement of the steady-state level of large numbers of polynucleotide sequences simultaneously. Microarrays currently in wide use include cDNA arrays and oligonucleotide arrays. Analyses using microarrays are generally based on measurements of the intensity of the signal received from a labeled probe used to detect a cDNA sequence from the sample that hybridizes to a nucleic acid probe immobilized at a known location on the microarray (see, for example, U.S. Pat. Nos. 6,004,755; 6,218,114; 6,218,122; and 6,271,002). Array-based gene expression methods are known in the art and have been described in numerous scientific publications as well as in patents (see, for example, M. Schena et al., Science, 1995, 270: 467-470; M. Schena et al., *Proc. Natl. Acad. Sci*. USA 1996, 93: 10614-10619; Chen et al., *Genom-*

*ics,* 1998, 51: 313324; U.S. Pat. Nos. 5,143,854; 5,445,934; 5,807,522; 5,837, 832; 6,040,138; 6,045,996; 6,284,460; and 6,607,885).

Once the levels of the HER2-associated RNA of interest have been determined for the biological sample being analyzed, they are compared to the levels in one or more control samples or to at least one expression profile map for breast cancer described herein. Comparison of levels according to methods of the present invention is preferably performed after the levels obtained have been corrected for both differences in the amount of sample assayed and variability in the quality of the sample used. Correction may be carried out by normalizing the levels against reference genes (e.g., housekeeping genes) in the same sample. Alternatively or additionally, normalization can be based on the mean or median signal (e.g., Ct in the case of RT-PCR) of all assayed genes or a large subset thereof (global normalization approach).

For a given set of HER2-associated RNA, comparison of an expression pattern obtained for a biological sample against an expression profile map established for breast cancer may comprise comparison of the normalized levels on a biomarker-by-biomarker (HER2-associated RNA-by-HER2-associated RNA) basis and/or comparison of ratios of levels within the set of biomarkers.

Using methods described herein, skilled physicians may select and prescribe treatments adapted to each individual subject based on the diagnosis of breast cancer provided to the subject through determination of the levels of the inventive HER2-associated RNA. In particular, the present invention provides physicians with a non-subjective means to diagnose cancer, which will allow for early treatment, when intervention is likely to have its greatest effect. Selection of an appropriate therapeutic regimen for a given patient may be made based solely on the diagnosis provided by the inventive methods. Alternatively, the physician may also consider other clinical or pathological parameters used in existing methods to diagnose cancer and assess its advancement.

In certain embodiments, the assays, methods and systems described herein relate to identifying a subject with breast cancer or a need for treatment for breast cancer. Certain embodiments are related to assays, methods and systems for identifying the severity of breast cancer in a sample, e.g., a biopsy sample, obtained from a subject. In some embodiments, where the level of HER2-associated RNA in the biological sample is at least about 2-fold, at least about 4-fold, at least about 8-fold, or at least about 10-fold increased (e.g., RRM2, TOP2A, CCNE2, EXO1, ANLN, DLGAP5, CDKN3, NUSAP1, CCNB2, FAM11B, HISH1H2BG, BUB1B, CDC6, MAL2, SQLE, KIF23, CCNB1, PRC1, CKS2, GINS1, HIST1H2BO, ECT2, ATAD2, GGCT, HISST2H2BE, NME1, GALNT7, MCM4, DHCR24, RAD21, TMEM97, HMGCS1, MSM01, LMNB2, or linc-STRAD6-2) as compared to a reference HER2-associated RNA level, the subject is identified as likely to have breast cancer, and/or metastatic breast cancer. In other embodiments, where the level of HER2-associated RNA in the biological sample is at least about 2-fold, at least about 4-fold, at least about 8-fold, or at least about 10-fold decreased (e.g., MERTK, linc-GJA1-2, or linc-SLC39A10-10) as compared to a reference HER2-associated RNA level, the subject is identified as likely to have breast cancer, and/or metastatic breast cancer. In such instances, a subject identified as likely to have breast cancer, and/or metastatic breast cancer can be treated with a more aggressive anti-cancer treatment regimen.

In some embodiments, where the level of HER2-associated RNA in the biological sample is at least about 2-fold, at least about 4-fold, at least about 8-fold, or at least about 10-fold increased (e.g., RRM2, TOP2A, CCNE2, EXO1, ANLN, DLGAP5, CDKN3, NUSAP1, CCNB2, FAM11B, HISH1H2BG, BUB1B, CDC6, MAL2, SQLE, KIF23, CCNB1, PRC1, CKS2, GINS1, HIST1H2BO, ECT2, ATAD2, GGCT, HISST2H2BE, NME1, GALNT7, MCM4, DHCR24, RAD21, TMEM97, HMGCS1, MSM01, LMNB2, or linc-STRAD6-2) as compared to a reference HER2-associated RNA level, the subject is predicted to have a poor outcome and low metastasis free survival, or a decreased survival chance as compared to a subject who has a HER2-associated RNA levels not statistically significant different or similar to reference HER2-associated RNA levels. In other embodiments, where the level of HER2-associated RNA in the biological sample is at least about 2-fold, at least about 4-fold, at least about 8-fold, or at least about 10-fold decreased (e.g., MERTK, linc-GJA1-2, or linc-SLC39A10-10) as compared to a reference HER2-associated RNA level, the subject is predicted to have a poor outcome and low metastasis free survival, or a decreased survival chance as compared to a subject who has a HER2-associated RNA levels not statistically significant different or similar to reference HER2-associated RNA levels. In such instances, a subject identified with a poor outcome and low metastasis free survival, or a decreased survival chance can be treated with a more aggressive anti-cancer treatment regimen.

In certain embodiments, the subject may be exhibiting a sign or symptom of breast cancer. In certain embodiments, the subject may be asymptomatic or not exhibit a sign or symptom of breast cancer, but can be at risk of developing breast cancer due to certain risk factors as described herein.

In some embodiments, the methods and assays described herein include (a) transforming the HER2-associated RNA into a detectable gene target; (b) measuring the amount of the detectable gene target; and (c) comparing the amount of the detectable gene target to an amount of a reference, wherein if the amount of the detectable gene target (e.g., HER2-associated RNA) is statistically different from that of the amount of the reference level for the gene target (e.g., HER2-associated RNA), the subject is identified as having cancer or is in need of a treatment for breast cancer.

In some embodiments, the reference can be a level of HER2-associated RNA in a normal healthy subject with no symptoms or signs of breast cancer or metastasis. For example, a normal healthy subject who does not have breast cancer. In some embodiments, the reference can also be a level of expression of HER2-associated RNA in a control sample, a pooled sample of control individuals or a numeric value or range of values based on the same. In some embodiments, the reference can also be a level of the biomarker in a tissue sample taken from non-cancerous tissue of the subject. In certain embodiments, wherein the progression of breast cancer in a subject is to be monitored over time, the reference can also be a level of HER2-associated RNA in a tissue sample taken from the tissue of the subject at an earlier date.

In certain embodiments, a HER2-associated RNA, such as RRM2, TOP2A, CCNE2, EXO1, ANLN, DLGAP5, CDKN3, NUSAP1, CCNB2, FAM11B, HISH1H2BG, BUB1B, CDC6, MAL2, SQLE, KIF23, CCNB1, PRC1, CKS2, GINS1, HIST1H2BO, ECT2, ATAD2, GGCT, HISST2H2BE, NME1, GALNT7, MCM4, DHCR24, RAD21, TMEM97, HMGCS1, MSM01, LMNB2, or linc-STRAD6-2, is upregulated in a biological sample, e.g., a biopsy sample from a subject with breast cancer. If the level of HER2-associated RNA is higher than a reference level of that biomarker, the subject is more likely to have cancer or to be in need of a treatment for breast cancer. The level of a HER2-associated RNA, which is higher than a reference level for that HER2-associated RNA, by at least about 10% than the reference amount, at least about 20%, at least about 30%, at least about 40%, at least about 50%, at least about 80%, at least about 100%, at least about 200%, at least about 300%, at least about 500% or at least about 1000% or more, is indicative that the subject has breast cancer.

In other embodiments, a HER2-associated RNA, such as MERTK, linc-GJA1-2, or linc-SLC39A10-10, is downregulated in a biological sample, e.g., a biopsy sample from a subject with breast cancer. If the level of HER2-associated RNA is lower than a reference level of that biomarker, the subject is more likely to have cancer or to be in need of a treatment for cancer. The level of a HER2-associated RNA which is lower than a reference level for that HER2-associated RNA by at least about 10% than the reference amount, at least about 20%, at least about 30%, at least about 40%, at least about 50%, at least about 80%, at least about 100%, at least about 200%, at least about 300%, at least about 500% or at least about 1000% or more, is indicative that the subject has breast cancer.

In another embodiment, the assays can include a system for transforming and measuring the amount levels of HER2-associated RNA as described herein and comparing them to reference expression levels. If the comparison system, which can be a computer implemented system, indicates that the amount of the measured expression product is statistically different from that of the reference amount, the subject from which the sample is collected can be identified as having an increased risk for having cancer or for a subject in need of a treatment for cancer or metastasis.

Systems (and computer readable media for causing computer systems) for performing the methods can include (a) at least one memory containing at least one computer program adapted to control the operation of the computer system to implement a method that includes (i) a determination module configured to identify and detect at the level of HER2-associated RNA in a biological sample obtained from a subject; (ii) a storage module configured to store output data from the determination module; (iii) a computing module adapted to identify from the output data whether the level of HER2-associated RNA measured in the biological sample obtained from a subject varies by a statistically significant amount from the HER2-associated RNA level found in a reference sample and (iv) a display module for displaying whether the level of HER2-associated RNA or other markers measured has a statistically significant variation in level in the biological sample obtained from a subject as compared to the reference HER2-associated RNA level and/or displaying the relative expression levels of the biomarkers, e.g., HER2-associated RNA levels and (b) at least one processor for executing the computer program.

Embodiments of the invention can be described through functional modules, which are defined by computer executable instructions recorded on computer readable media and which cause a computer to perform method steps when executed. The modules are segregated by function for the sake of clarity. However, it should be understood that the modules/systems need not correspond to discreet blocks of code and the described functions can be carried out by the execution of various code portions stored on various media and executed at various times. Furthermore, it should be appreciated that the modules can perform other functions, thus the modules are not limited to having any particular functions or set of functions.

The computer readable storage media can be any available tangible media that can be accessed by a computer. Computer readable storage media includes volatile and nonvolatile, removable and non-removable tangible media implemented in any method or technology for storage of information such as computer readable instructions, data structures, program modules or other data. Computer readable storage media includes, but is not limited to, RAM (random access memory), ROM (read only memory), EPROM (erasable programmable read only memory), EEPROM (electrically erasable programmable read only memory), flash memory or other memory technology, CD-ROM (compact disc read only memory), DVDs (digital versatile disks) or other optical storage media, magnetic cassettes, magnetic tape, magnetic disk storage or other magnetic storage media, other types of volatile and non-volatile memory, and any other tangible medium which can be used to store the desired information and which can accessed by a computer including and any suitable combination of the foregoing.

Computer-readable data embodied on one or more computer-readable media may define instructions, for example, as part of one or more programs that, as a result of being executed by a computer, instruct the computer to perform one or more of the functions described herein, and/or various embodiments, variations and combinations thereof. Such instructions may be written in any of a plurality of programming languages, for example, Java, J#, Visual Basic, C, C#, C++, Fortran, Pascal, Eiffel, Basic, COBOL assembly language, and the like, or any of a variety of combinations thereof. The computer-readable media on which such instructions are embodied may reside on one or more of the components of either of a system, or a computer readable storage medium described herein, may be distributed across one or more of such components.

The computer-readable media may be transportable such that the instructions stored thereon can be loaded onto any computer resource to implement the aspects discussed herein. In addition, it should be appreciated that the instructions stored on the computer-readable medium, described above, are not limited to instructions embodied as part of an application program running on a host computer. Rather, the instructions may be embodied as any type of computer code (e.g., software or microcode) that can be employed to program a computer to implement aspects of the present invention. The computer executable instructions may be written in a suitable computer language or combination of several languages. Basic computational biology methods are known to those of ordinary skill in the art and are described in, for example, Setubal and Meidanis et al., Introduction to Computational Biology Methods (PWS Publishing Company, Boston, 1997); Salzberg, Searles, Kasif, (Ed.), Computational Methods in Molecular Biology, (Elsevier, Amsterdam, 1998); Rashidi and Buehler, Bioinformatics Basics: Application in Biological Science and Medicine (CRC Press, London, 2000) and Ouelette and Bzevanis Bioinformatics: A Practical Guide for Analysis of Gene and Proteins (Wiley & Sons, Inc., 2nd ed., 2001).

The functional modules of certain embodiments of the invention include at minimum a determination module, a storage module, a computing module, and a display module. The functional modules can be executed on one, or multiple, computers, or by using one, or multiple, computer networks.

The determination module has computer executable instructions to provide e.g., levels of expression products etc in computer readable form.

The determination module can comprise any system for detecting a signal elicited from the HER2-associated RNA described herein in a biological sample. In some embodiments, such systems can include an instrument, e.g., StepOnePlus Real-Time PCR systems (Applied Biosystems) as described herein for quantitative RT-PCR. In another embodiment, the determination module can comprise multiple units for different functions, such as amplification and hybridization. In one embodiment, the determination module can be configured to perform the quantitative RT-PCR methods described in the Examples, including amplification, detection, and analysis.

The information determined in the determination system can be read by the storage module. As used herein the "storage module" is intended to include any suitable computing or processing apparatus or other device configured or adapted for storing data or information. Examples of electronic apparatus suitable for use with the present invention include stand-alone computing apparatus, data telecommunications networks, including local area networks (LAN), wide area networks (WAN), Internet, Intranet, and Extranet, and local and distributed computer processing systems. Storage modules also include, but are not limited to: magnetic storage media, such as floppy discs, hard disc storage media, magnetic tape, optical storage media such as CD-ROM, DVD, electronic storage media such as RAM, ROM, EPROM, EEPROM and the like, general hard disks and hybrids of these categories such as magnetic/optical storage media. The storage module is adapted or configured for having recorded thereon, for example, sample name, alleleic variants, and frequency of each alleleic variant. Such information may be provided in digital form that can be transmitted and read electronically, e.g., via the Internet, on diskette, via USB (universal serial bus) or via any other suitable mode of communication.

As used herein, "stored" refers to a process for encoding information on the storage module. Those skilled in the art can readily adopt any of the presently known methods for recording information on known media to generate manufactures comprising expression level information.

The "computing module" can use a variety of available software programs and formats for computing the relative expression level of the HER2-associated RNA described herein. Such algorithms are well established in the art. A skilled artisan is readily able to determine the appropriate algorithms based on the size and quality of the sample and type of data. By way of an example, when the level of HER2-associated RNA in a biological sample obtained from a subject is measured, a comparison module can compare or match the output data—with a reference HER2-associated RNA level in a reference sample. In certain embodiments, the reference expression level can have been pre-stored in the storage module. During the comparison or matching process, the comparison module can determine whether the expression level in the tissue sample obtained from a subject is lower than the reference expression level to a statistically significant degree. In various embodiments, the comparison module can be configured using existing commercially-available or freely-available software for comparison purpose, and may be optimized for particular data comparisons that are conducted.

The computing and/or comparison module, or any other module of the invention, can include an operating system (e.g., UNIX) on which runs a relational database management system, a World Wide Web application, and a World Wide Web server. World Wide Web application includes the executable code necessary for generation of database language statements (e.g., Structured Query Language (SQL) statements). Generally, the executables will include embedded SQL statements. In addition, the World Wide Web application may include a configuration file, which contains pointers and addresses to the various software entities that comprise the server as well as the various external and internal databases which must be accessed to service user requests. The Configuration file also directs requests for server resources to the appropriate hardware—as may be necessary should the server be distributed over two or more separate computers. In one embodiment, the World Wide Web server supports a TCP/IP protocol. Local networks such as this are sometimes referred to as "Intranets." An advantage of such Intranets is that they allow easy communication with public domain databases residing on the World Wide Web (e.g., the GenBank or Swiss Pro World Wide Web site). Thus, in a particular preferred embodiment of the present invention, users can directly access data (via Hypertext links for example) residing on Internet databases using a HTML interface provided by Web browsers and Web servers.

The computing and/or comparison module provides a computer readable comparison result that can be processed in computer readable form by predefined criteria, or criteria defined by a user, to provide content based in part on the comparison result that may be stored and output as requested by a user using an output module, e.g., a display module.

In certain embodiments, the content displayed on the display module can indicate whether the HER2-associated RNA measured have a statistically significant variation in expression (e.g., increase or decrease) between the biological sample obtained from a subject as compared to a reference expression level. In certain embodiments, the content displayed on the display module can indicate the degree to which the HER2-associated RNA were found to have a statistically significant variation in expression between the biological sample obtained from a subject as compared to a reference expression level. In certain embodiments, the content displayed on the display module can indicate whether the subject has an increased risk of having cancer, and/or the severity of the cancer. In certain embodiments, the content displayed on the display module can indicate whether the subject is in need of a treatment for cancer. In certain embodiments, the content displayed on the display module can indicate whether the subject has an increased risk of having a more severe case of cancer or metastasis. In some embodiments, the content displayed on the display module can be a numerical value indicating one of these risk or probabilities. In such embodiments, the probability can be expressed in percentages or a fraction.

Example 1

We postulated that identifying the key genes (both coding and non-coding) that become deregulated in response to HER2 amplification could provide important insights into how HER2 amplification affects cell proliferation. Furthermore, identifying novel non-coding genes, such as lincRNAs, that become deregulated when HER2 becomes amplified may potentially provide clues into global changes in gene expression patterns observed in HER2+ breast cancer.

To further our understanding of the effects of HER2 signaling on gene expression of both mRNAs as well as novel non-coding genes such as lincRNAs, we utilized a combined in vitro and in vivo transcriptomic approach to pinpoint critical downstream genes. The expression of these identified mRNAs and lincRNAs were subsequently examined in RNA-seq data sets obtained from The Cancer Genome Atlas (TCGA) project to further refine our top candidates. Our results led to the identification of potentially key mRNAs and lincRNAs that may contribute to HER2+ breast cancer.

Materials and Methods

Next Generation RNA-Sequencing Files: All Raw Files have been Deposited in GEO: GSE60182

Clinical Trial Information: Institute: Brown University Oncology Group (Brown University, Yale University, Cedar-Sinae Center), PI: William Sikov MD; Correlative Science PI: Lyndsay Harris MD; BrUOG Study ID: BR-211B; Clinical Trials.gov ID NCT00617942.

RNA Isolation and Next Generation RNA Sequencing (RNA-Seq) from Tumor Samples (Clinical Trial)

Frozen biopsied cores were processed for RNA isolation using AllPrep (Qiagen), and the Ovation RNA-seq System (NuGen) was used for RNA amplification. Library preparation was performed using TruSeq v3 (Illumina) and then sequenced on an Illumina HiSeq2500. The sequenced reads were aligned to the human genome version hg19 using GSNAP (Wu and Nacu, 2010). The uniquely aligned reads were further analyzed using Cufflinks V2.0.2 and aligned to human mRNAs and lincRNA databases (Cabili et al., 2011). Expression values were calculated as FPKM (fragment per kilobase of exon per million of mapped fragments) and were used to determine expression of lincRNAs and mRNAs in pre- and post-treatment samples. Transcripts were called expressed if FPKM values across either all pre-treatment samples or all post-treatment samples were ≥1.0 or ≥0.25, for mRNAs and lincRNAs, respectively. The mean expression level was calculated and differences in expression between pre- and post-treatment samples were assessed for the 11 patients that achieved a pathological complete response (pCR) using the non-parametric Wilcoxon test for paired samples. Additionally, fold change (post/pre) were calculated to identify differentially expressed transcripts. Transcripts were deemed differentially expressed if the fold change was ≥2.0 or ≤0.5. Heatmaps were generated in R using heatmap.2, and Z-scores were scaled by row using standard Z-score calculation of log fold change.

Cell Culture of Breast Cancer Cell Lines

Human breast cancer cell lines were grown in Hybri-Care Medium (ATCC® 46-X™) supplemented with 10% fetal bovine serum (FBS) (Bioexpress) and 100 units/ml of Penicillin and 100 μg/ml Streptomycin (Life Technologies) at 37° C. with 5% $CO_2$.

RNA isolation from cell lines: RNA from BT474 cells was isolated using RNeasy® Mini Kit (Qiagen) according to the manufacturer's protocol. An added DNase (Qiagen) treatment step was included after the first wash to remove DNA contamination of RNA preps.

siRNA Transfections

The knockdown of HER2 was achieved through the transfection of HER2-specific siRNAs (Life Technologies, Catalogue #4390824, s611 and s613) at a final concentration of 15 nM with Lipofectamine RNAiMax (Life Technologies) at 7.5 μL/well of 6-well plate. Negative control siRNA #1 and #2 (Ambion Cat. # AM4611 and AM4613) were used as negative controls.

Western Blot Analyses

Protein lysates were prepared with Laemmli Sample Buffer (BioRad) and separated on a gradient 4-20% SDS-PAGE Mini-Protean® TGX™ Gels (BioRad). The gel was transferred to a nitrocellulose membrane (Thermo Scientific) and probed with primary antibodies overnight. Anti-β-actin (Ambion, AM4302, 3.1 mg/ml) was used as a loading control at a dilution of 1:1000, and anti-HER2/Erb2 (Cell Signaling, 2242S) was used to detect HER2 at a dilution of 1:500. Anti-mouse HRP (Thermo Scientific, 32230) and anti-rabbit HRP (Abcam, ab6721) were used as secondary antibodies. HRP was activated using SuperSignal® West Pico Chemiluminescent Substrate (Thermo Scientific) for autoradiography.

Next Generation RNA Sequencing of BT474 Cells

After RNA was isolated from BT474 samples, we assessed the quality of RNA using BioRad Experion. RNA samples with RNA integrity number (RIN) larger than 8 (max is 10) were considered high quality and suitable for RNA-seq. Library preparation was performed using Script-seg™ Complete Gold (Human/Mouse/Rat) (Illumina) and sequenced on Illumina Hi-Seq2500. Six samples were run on a single flow cell. We generated 100 bp paired-end strand-specific sequences, which were mapped to human genome release hg19 using TopHat with 2 mismatches allowed for full-length reads. The raw reads were mapped to human genes annotated in RefSeq database and lincRNAs annotated in Cabili et al. using Cufflinks V2.0.2, and subsequently used for differential gene expression analysis after normalizing the values to the total mapped reads in each sample, see supporting file 14. Expression values were calculated as FPKM (fragment per kilobase of exon per million of mapped fragments) and were used to determine expression of both lincRNAs and mRNAs in HER2 knock down (KD) and negative control (NC) siRNA samples. Transcripts were considered expressed if FPKM values across either all BT474 HER2 KD samples or all NC samples were ≥1.0 for mRNAs and ≥0.25 for lincRNAs. The mean expression level was calculated, and from this statistically significant differences in expression between HER2 KD samples and NC samples was determined using a paired t-test in R. Additionally, fold changes (HER2 KD/NC) were calculated to identify differentially expressed transcripts. Transcripts were deemed differentially expressed if the fold change was ≥2.0 or ≤0.5. Heatmaps were generated in R using heatmap.2, and Z-scores were scaled by row using standard Z-score calculation of log fold change.

Real Time Quantitative PCR (RT-qPCR)

Real time quantitative PCR (RT-qPCR): RNA was converted to cDNA using RNA to cDNA EcoDry™ Premix Random Hexamers (Clontech). Primers pairs were designed using primer3 software, and most primers used were designed to span exon-exon boundaries. A complete list of all primers is included. Maxima SyBr Green/ROX qPCR Master Mix (Thermo Scientific) was used for qRT-PCR. A comparative $C_T$ quantitation was performed with a hold stage of 50° C. for 2 min and 95° C. for 10 min followed by 40× cycle of 95° C. for 15 s and 60° C. for 1 min and finally melt curve at 95° C. for 15 s, 60° C. for 1 min, and a ramp to 95° C. at 0.3° C. increments. Analysis was done using the $2^{-\Delta\Delta C_T}$ method with GAPDH as the reference gene.

Analysis of Next Generation RNA Sequencing from the Cancer Genome Atlas (TCGA)

RNA sequencing (RNA-seq) fastq files from 12 tumor and 12 adjacent matched normal breast cancer pairs were obtained through The Cancer Genome Atlas (TCGA) consortium via the Cancer Genomics Hub (https://cghub.ucsc.edu) (Supporting file 9). Sequences were aligned to UCSC hg19 with default parameters in TopHat v2.0.11 specifying an unstranded library strategy. Aligned sequences were then assembled into both mRNA and lincRNA transcripts using default parameters in Cufflinks v2.1.1. Relative transcript abundance was reported from Cufflinks as Fragments Per Kilobase of exon per Million fragments mapped (FPKM). Transcripts were deemed as expressed if FPKM values across either all tumor samples or all matched normal samples were ≥1.0 for mRNAs and ≥0.25 for lincRNAs. The non-parametric Wilcoxon test for paired samples was used to test for statistical significance ($p<0.05$) using the statistical software R [R Development Core Team. (2011) R: a language and environment for statistical computing. R Foundation for Statistical Computing, Vienna, Austria]. Fold changes were calculated as tumor/normal, and transcripts with greater than a 2-fold change were selected as differentially expressed. Over enrichment analysis of differentially expressed mRNAs using NCBI cancer pathways was also performed in R using fisher's exact test. P values were corrected for multiple testing using the Bonferroni correction. Heatmaps were generated in R using heatmap.2, and Z-scores were scaled by row using standard Z-score calculation of log fold change.

Results

Inhibition of HER2 by Trastuzumab In Vivo Affects the Expression of Both mRNAs and lincRNAs Previous studies have shown that HER2 inhibition in cell culture models of HER2+ breast cancer leads to dramatic changes in the expression of mRNAs. However, it is not currently known which of these mRNAs are affected as a result of HER2 inhibition in tumors in vivo, as well as the effects of HER2 inhibition on regulatory non-coding RNAs such as lincRNAs. To identify the mRNAs and lincRNAs that become affected by HER2 inhibition in vivo, we analyzed RNA-seq data from a clinical trial that we originally designed to predict benefit from the HER2 inhibitor, trastuzumab (Herceptin®) (Clinical Trials.gov ID NCT00617942, also see methods). Trastuzumab is a monoclonal antibody drug designed to target the HER2 receptor by potentially inhibiting its heterodimerization. The clinical trial accrued 80 patients of which 50 pairs of tumors could be biopsied pre-trastuzumab and post-trastuzumab (post one dose, ~10-14 days). All patients continued receiving a combination of chemotherapy and trastuzumab for 4 months, and a subset of thirteen tumor pairs representing the extremes of response to treatment, was subjected to total RNA isolation and RNA-seq analysis. Eleven out of these thirteen patients were identified as responders to trastuzumab as measured by pathological complete response (pCR). We reasoned that since trastuzumab was an effective therapeutic drug in these eleven HER2+ breast cancer patients, changes in gene expression pre- and post-one dose of trastuzumab would reflect mRNAs and lincRNAs regulated through HER2. Therefore, we identified differentially expressed mRNAs and lincRNAs pre-vs post-one dose of trastuzumab treatment in our RNA-seq data set of these eleven patients that were responsive to treatment as measured by pCR.

We calculated FPKM (fragments per kilobase of exon per million fragments mapped) values of each known mRNA and lincRNA in the human genome in each RNA-seq sample (2.2 total: 11 pre-vs 11 post-trastuzumab). We calculated an average FPKM of each mRNA and lincRNA in pre-vs post-trastuzumab, and subsequently calculated a fold change of Post/Pre for each mRNA and lincRNA. We identified 228 mRNAs and 28 lincRNAs to be differentially expressed (FIGS. 1A-B). We also performed pathway analysis on differentially expressed mRNAs and identified five cancer-related pathways to be significantly affected ($p<0.05$, p-values ranged from 0.006-0.00004) (FIG. 1C). In summary, we identified a set of mRNAs and lincRNAs that become affected when HER2 signaling is inhibited in vivo. However, because of genetic and environmental differences of these 11 patients, we observed heterogeneity in the level of differential expression of both mRNAs and lincRNAs. Thus, to further refine our list of key mRNAs and lincRNAs that are critical components of the HER2 pathway, we decided to modulate HER2 in a cell culture model.

HER2 Signaling Affects the Expression of mRNAs as Well as lincRNAs in Cell Culture Model of HER2+ Breast Cancer We began our studies in BT474 cells, which are HER2+ breast cancer cells that have been utilized extensively as a cell culture model to study HER2+ breast cancer. To identify mRNAs and lincRNAs that are downstream of HER2 signaling in BT474 cells, we utilized a loss-of-function approach in which we depleted HER2 using validated siRNAs and examined changes in gene expression using RNA-seq. We transfected BT474 cells with siRNAs targeting HER2, and simultaneously transfected the same number of cells with negative control siRNAs. We initially examined HER2 mRNA levels using RT-qPCR at 48 and 72 hours. At these time points, we found that the siRNAs were effective at knocking down HER2 by 80 and 87 percent, respectively (FIG. 2A). Subsequently, we performed a new round of transfections at 24, 48 and 72 hours, and examined HER2 protein levels by western blot analysis. At 24 hours there was a modest reduction in HER2 protein levels, however, a significant reduction in HER2 protein levels in comparison to cells transfected with negative control siRNAs was achieved 48 hours post-transfection (FIG. 2B). Based on these gene expression analyses of HER2 knock down with siRNAs, the 48 hour post-transfection time point was chosen as optimal to sufficiently deplete HER2 at both the mRNA and protein levels, while still capturing some of the early changes in mRNAs and lincRNAs expression due to loss of HER2. To that end, equal numbers of BT474 cells were transfected with either HER2 siRNAs or negative control siRNAs in three biological replicates, and at 48 hours post-transfection total RNA was isolated, quantified, and subjected to RNA-seq.

We found 1,015 mRNAs (303 up-regulated and 712 down-regulated) and 167 lincRNAs (139 up-regulated and 28 down-regulated) to be differentially expressed by ≥2-fold in the HER2-depleted BT474 cells in comparison to cells transfected with negative control siRNAs (FIGS. 2C-D). To place our findings into context, we identified a previous study that utilized mRNA microarrays to examine the effects of HER2 inhibition by trastuzumab on mRNAs in BT474 and SKBR3 cells. This study reported sixteen mRNA genes that are significantly down-regulated in response to HER2 inhibition by trastuzumab. We found that eight of these sixteen mRNA genes were also significantly down-regulated in our current study. We designed primers for those mRNA genes, and confirmed in an independent set of knockdown experiments that their expression is altered in response to HER2 depletion in BT474 breast tumor cells by RT-qPCR (FIG. 2E). Furthermore, pathway analysis of differentially expressed mRNAs revealed numerous affected pathways post HER2 depletion in BT474 cells.

Since no previous studies of lincRNAs modulated in response to HER2 depletion or inhibition are available, we selected five lincRNAs from our RNA-seq data for validation by qPCR in an independent knockdown experiment in BT474 cells. We selected these lincRNAs based on fold changes and p-values and we included both up- and down-regulated lincRNAs in response to HER2 depletion. Four out of the five lincRNAs showed statistically significant up- or down-regulation in response to HER2 depletion by RTqPCR similar to what we observed by RNA-seq analysis (FIG. 2F). To further confirm that these lincRNAs are downstream of the HER2 pathway, and that changes in their expression are not due to off-target effects of siRNAs, we utilized a second independent siRNA against HER2. First, we confirmed that this second siRNA is effective at knocking down HER2 protein levels by western blot analysis (FIG. 3A). Next, we performed qPCR analysis on the same 5 lincRNAs (see FIG. 2F), and found that four out of the five lincRNAs show a similar response to knocking down HER2 with the second siRNA, but only three lincRNAs pass a p-value of <0.05 (FIG. 3B). Also, the expression of lincMCl1-1, which was not affected with first siRNA, was responsive to the second siRNA, similar to what we observed by RNA-seq. These experiments demonstrate that HER2 depletion in BT474 cells affect the expression of both mRNAs and lincRNAs, however, some variability is observed due to off-targets effects of siRNA-mediated depletion. Thus, to overcome these limitations we identified mRNAs and lincRNAs that are affected by both HER2 inhibition by trastuzumab in vivo and HER2 depletion in BT474 cells by siRNAs.

To identify mRNAs and lincRNAs that are affected by both HER2 inhibition by trastuzumab in tumors and HER2 depletion in cell culture, we intersected differentially expressed mRNAs and lincRNAs that we identified post HER2 knockdown in BT474 cells with differentially expressed mRNAs and lincRNAs that we identified in response to HER2 inhibition by trastuzumab in vivo. We found 44 mRNAs and 3 lincRNAs to be common between the two data sets (FIGS. 4A-B, and Supporting file 7 and 8). Some of the 44 mRNA genes identified are key components of the PLK1 signaling pathway and E2F transcription factor network (FIG. 4C), which are key pathways affected in HER2+ tumors. In summary, we have identified a small set of mRNAs and lincRNAs that are affected in response to HER2 inhibition/depletion in vivo and in cell culture suggesting an important role of not only mRNAs but also lincRNAs in HER2+ breast cancer. To gain further insights into the potential role of these genes in HER2+ breast cancer, we next examined their expression in a cohort of HER2+ breast tumors and their matched normal control tissue in the Cancer Genome Atlas (TCGA) database.

Thousands of mRNAs and Hundreds of lincRNAs are Differentially Expressed in HER2+ Breast Cancer Tumors By using transcriptomic analyses pre-vs post-HER2 knockdown in cell culture and pre-vs post-HER2 inhibition in tumors, we are able to identify a small set of lincRNAs and mRNAs that are putative members of the HER2 regulatory network. To further validate our observations, we turned to RNA-seq data from The Cancer Genome Atlas (TCGA) project to determine the expression patterns of these mRNAs and lincRNAs in HER2 tumors vs matched normal tissue. The TCGA represents one of the most comprehensive studies of RNA expression in thousands of cancers including breast cancer. We mined the TCGA RNA-seq data for HER2+ breast tumors with matched normal tissue. In total, we identified 12 patients (24 RNA-seq samples: from 12 tumors and 12 matched normal tissue). Within this TCGA cohort, we identified 2,521 mRNAs and 283 lincRNAs to be differentially expressed between these tumors and their matched normal pairs (FIGS. 5A-B). We performed pathway analysis of differentially expressed mRNAs in the TCGA data set, and as expected, cancer-related pathways were highly enriched (FIG. 5C).

Figure 6:
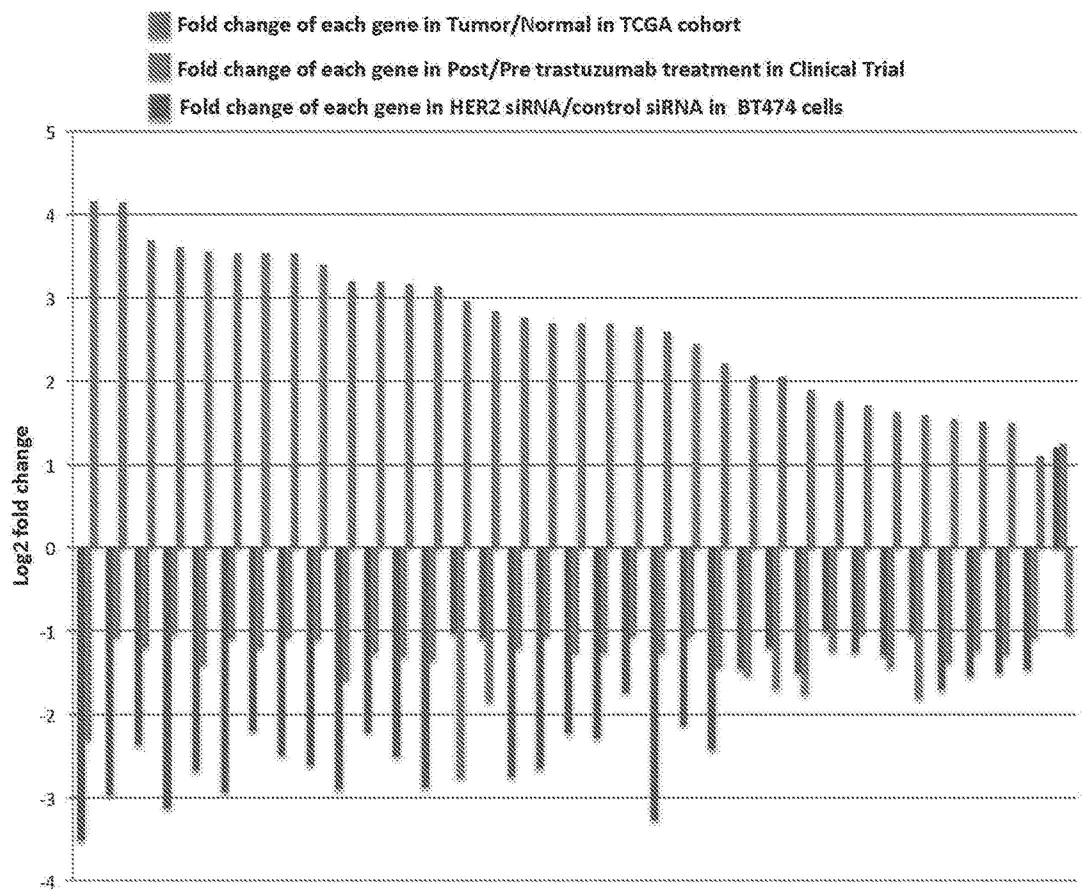
FIG. 6 illustrates identification of 35 mRNAs that are affected in all three data sets with the expected directionality of expression. Of the 44 mRNAs that are affected by both HER2 inhibition in tumors by trastuzumab and HER2 knock down in BT474 cells, 35 of these mRNAs were also deregulated in HER2+ tumors vs normal tissues (TCGA). These 35 mRNA transcripts are found in to be dysregulated in all three data sets: TCGA HER2+ (Tumor/Normal), Trastuzumab clinical trial samples (Post-/Pre-trastuzumab treatment), and in BT474 cells (HER2 siRNA/control siRNA). We graphed the expression values of these 35 mRNAs in all three data sets, and strikingly each mRNA shows similar directionality in HER2 knockdown in BT474 cells and in HER2 inhibition in vivo, and as expected, negatively correlated in the TCGA cohort (tumor/normal)

To determine the expression patterns of the 44 mRNAs and 3 lincRNAs that are affected in response to both HER2 knockdown (in BT474 cells) and HER2 inhibition (in tumors in vivo), we examined their expression in the TCGA RNA-seq data. Of the 44 mRNAs identified, 35 mRNAs are also dysregulated in the TCGA cohort. We graphed the expression values of each of these 35 mRNAs in all three data sets: HER2 inhibition in vivo (Post-trastuzumab/Pre-trastuzumab), HER2 knockdown in BT474 cells (siHER2/siControl), and TCGA cohort (Tumor/Normal). Strikingly, each mRNA shows a similar directionality in HER2 knockdown in BT474 cells and in HER2 inhibition in tumors in vivo, and as expected, negatively correlated in the TCGA cohort (tumor/normal) (FIG. 6).

We also examined the expression of the three intersected lincRNAs in our analysis of TCGA RNA-seq data. In this analysis, it was expected that a lincRNA that is up-regulated in response to HER2 depletion and inhibition to be down-regulated in tumor samples in comparison to matched normal tissue, and vice versa. Linc-STARD6-2, which we found to be down-regulated when HER2 was knocked-down or inhibited, is up-regulated in 8/12 tumors in comparison to their matched normal tissue (FIG. 7A). Linc-GJA1-2 and linc-SLC39A10-10, which become up-regulated in response to HER2 knockdown or inhibition, are down-regulated in 10/11 and 9/12 tumors in comparison to their matched normal tissue, respectively (FIGS. 7B-C).

From the above description of the invention, those skilled in the art will perceive improvements, changes and modifications. Such improvements, changes and modifications within the skill of the art are intended to be covered by the appended claims. All references, publications, and patents cited in the present application are herein incorporated by reference in their entirety.

Having described the invention, we claim:

1. A method for treating HER2 positive breast cancer in a subject in need thereof, the method comprising:

administering to cancer cells of the subject an RNA inhibitor agent effective to decrease the level of HER2-associated RNA that is over expressed in the breast cancer cells of the subject, wherein the at least one HER2-associated RNA is linc-STRAD6-2.

2. The method of claim 1 wherein the agent is selected from the group consisting of siRNA, miRNA, stRNA, snRNA, and antisense nucleic acid to the HER2-associated RNA.

* * * * *